US005166347A

United States Patent [19]

[11] Patent Number: 5,166,347

[45] Date of Patent: Nov. 24, 1992

Izawa et al.

[54] CARBOXIMIDAMIDE DERIVATIVES

[75] Inventors: Toshio Izawa; Tomoko Kashiwabara; Shohachi Nakajima; Nobuyuki Ogawa, all of Maebashi, Japan

[73] Assignee: Kirin Beer Kabushiki Kaisha, Tokyo, Japan

[21] Appl. No.: 455,973

[22] Filed: Dec. 22, 1989

[30] Foreign Application Priority Data

| | | | |
|---|---|---|---|
| Dec. 27, 1988 | [JP] | Japan | 330336 |
| Aug. 7, 1989 | [JP] | Japan | 204176 |
| Nov. 17, 1989 | [JP] | Japan | 298950 |

[51] Int. Cl.$^5$ .................. C07D 241/00; C07D 215/12; C07D 333/22; C07D 255/00

[52] U.S. Cl. .................................... 544/336; 546/176; 546/330; 549/77; 549/491; 558/408; 558/409

[58] Field of Search ................ 546/330, 176; 514/357, 514/314, 444, 461, 345, 351; 549/77, 491; 544/336; 558/408, 409

[56] References Cited

U.S. PATENT DOCUMENTS

| | | | |
|---|---|---|---|
| 3,793,451 | 2/1974 | Dixon | 514/357 |
| 3,910,928 | 10/1975 | McCall et al. | 558/408 |
| 4,407,816 | 10/1983 | Tomiyama | 514/438 |
| 4,806,553 | 2/1989 | Shiokawa et al. | 514/351 |

FOREIGN PATENT DOCUMENTS

| | | |
|---|---|---|
| 0233745 | 2/1987 | European Pat. Off. . |
| 3005786 | 8/1980 | Fed. Rep. of Germany . |
| 2906489 | 9/1980 | Fed. Rep. of Germany . |

OTHER PUBLICATIONS

Chem. Abstracts vol. 112, 35645X.

Lwoski, W. "Convenient Preparation of Alkyl N-Cyanoimidates" *Synthesis*, p. 263 (1971).

Cautier, J-A, et al., "Preparation and Synthetic uses of amidines" *The Chemistry of Amidines and Imidates*, pp. 283-348, (John Wiley and Sons, 1975).

Watthey, J. W. H., et al., *J. Med. Chem.* 23:690-692 (1980).

Eloy, F., et al., *Bull. Soc. Chim.* Belges 78:41-46 (1969).

*Primary Examiner*—Thurman M. Page
*Assistant Examiner*—Peter F. Kulkosky
*Attorney, Agent, or Firm*—Ladas & Parry

[57] ABSTRACT

Novel carboximidamide derivatives represented by the following formula (A) and acid adduct salts thereof are disclosed:

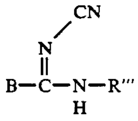

(A)

wherein all the substituents have the same meanings as defined above.

N-cyano-pyridinecarboximidate compounds represented by the following formula (II) which are the intermediates for preparing of N-cyano-N'-substituted-pyridinecarboximidamide derivatives wherein the substituent B in the above described formula (A) is pyridine is also disclosed:

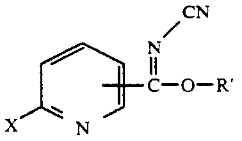

(II)

wherein all the substitutents have the same meanings as defined above.

The process for preparing the compounds, the pharmaceutical agents comprising the compound having vasodilating effect, and the therapeutic method of dosing the compound on patients for therapy are also disclosed.

12 Claims, 3 Drawing Sheets

CARBOXIMIDAMIDE DERIVATIVES

TECHNICAL FIELD

The present invention relates to novel carboximidamide derivatives having vasodilating effect, more particularly N-cyano-N'-substituted pyridinecarboximidamide derivatives and N-cyano-N'-substituted carboximidamide derivatives in which N'-position is substituted by an alkyl substituent, or acid adduct salts thereof, intermediates for preparing them and a process for preparing them.

The present invention also relates to potassium channel activating agents, hypotensors, therapeutic agents of ischemic heart disease, ameliorants of peripheral circulation, ameliorants of cerebral circulation, therapeutic agents of thrombosis and antasthmatics which contain as an active ingredient the above-described N-cyano-N'-substituted pyridinecarboximidamide derivative or an acid adduct salt thereof, and hypotensors which contain as an active ingredient the N-cyano-N'-substituted carboximidamide derivative wherein the N'-position is substituted by an alkyl group or an acid adduct salt thereof. The present invention further relates to the therapeutic methods for patients who need the treatments of potassium channel activation, the treatments of hypertension, the treatment of ischemic heart disease, the treatment of peripheral circulatory failure, the treatment of cerebral circulatory failure, the treatment of thrombosis and the asthma using the aforementioned N-cyano-N'-substituted pyridinecarboximidamide derivative or an acid adduct salt thereof, or the therapeutic method for patients who need hypotensive treatment using the N-cyano-N'-substituted carboximidamide derivative in which N'-position is substituted by an alkyl group or an acid adduct salt thereof.

BACKGROUND ART

As the well-known compounds among the N-cyanopyridinecarboximidamide compounds in relation to the present invention, there are mentioned N-cyano-3-pyridinecarboximidamide [see Journal of Medicinal Chemistry 23, 690–692 (1980)], N-cyano-4-(2-ethylpyridine)carboximidamide (see Leprosy Review, 23–30, 1983) and N-cyano-4-pyridinecarboximidamide (see Bulletin des Societes Chimiques Belges, 78, 41–46, 1969). However, all of these compounds are the ones which have no substituent in N'-position and are reported only as the intermediates for producing of diuretics or as the agents for the treatment of Hansen's disease. There is no report of other utility. The syntheses of carboximidamides have been investigated from various aspects, and various synthetic methods mainly of benzenecarboximidamide compounds or alkylcarboximidamides are investigated (see, for example, "The Chemistry of amidines and imidates", Edited by Saul Patai, John Wiley and Sons, 1975). For example, in the case of an N-cyano-N'-substituted benzenecarboximidamide, a synthetic method which comprises converting cyanobenzene into an alkyl benzeneimidate, further reacting cyanamide ($NH_2CN$) with the alkyl benzeneimidate in pH 6.5–7.0 to form an alkyl N-cyanobenzeneimidate and reacting an amine compound 25 with the aforementioned imidate has been proposed (see Synthesis, 263, 1971; Synthesis, 673–675, 1978; Journal of Organic Chemistry, 44, 1562–1563 (1979); Synthesis, 123–124, 1980; Synthesis, 402–404, 1983).

However, according to the conventional synthetic methods, particularly the synthesis within the above-described pH range, analkyl N-cyanopyridinecarboximidate is not produced, and thus an N-cyano-N'-substituted pyridinecarboximidamide compound could not be produced.

On the other hand, as regards antihypertensive agents, a variety of pharmaceutical agents have been proposed, but, so far as the present inventor knows, none of these agents have satisfactory effects on the pathologies and patients of all kinds of hypertensions such as essential hypertension, secondary hypertension or the like. Also as regards the treatment of angina pectoris, calcium antagonists or β-blockers and the like have hitherto been used, but the attack of angina pectoris is not completely suppressed by the use of these agents. There are reported no therapeutics having satisfactory cardioprotective effect after the reperfusion of coronary vessel when the pathology develops into myocardial infarction. New types of cardiovascular therapeutics with consideration for these points are continuously desired.

For instance, as a cardiovascular therapeutic based on a new function mechanism, a compound having a potassium channel activating effect has recently been proposed.

The potassium channel activating effect is an effect that potassium channel on cell membrane is opened and the permeability of potassium is enhanced so that hyperpolarization is caused and the contraction of smooth muscle or myocardium is suppressed. As compounds having potassium channel activating effect, there are known, for example, nicorandil, pinacidil and chromakalim (see Trends in Pharmacological Sciences, 8, 283, 1987). These exhibit vasodilating effect, antihypertensive effect, coronary blood flow increasing effect, cerebral vasodilative effect and bronchodilatative effect in animal experiments [see European Journal of Pharmacology, 152, 331 (1988); The Journal of Pharmacology and Experimental Therapeutics, 232, 369 (1985); Journal of Cardiovascular Pharmacology, 8, 798 (1986); Japan Heart Journal, 20, 881 (1979); European Journal of Pharmacology, 99, 219 (1984); British Journal of Pharmacology, 95, 763 (1988)]. Furthermore, these agents clinically exhibit utilities as an antihypertensive drug [see Clinical Physiology, 1, 375 (1981); Journal of Hypertension, 4, S166 (1986)] or as an antianginal drug [see RINSHO YAKURI, 13, 311 (1982)].

As the well-known carboximidamide compounds except the N-cyano-pyridinecarboximidamide compounds relating to the present invention, there are mentioned N-cyano-5-nitro-2-furamidine (Japanese Patent Publication No. 20453/68 and British Patent No. 1133950); N-cyano-2-thiophenecarboximidamide and N-cyano-3-thiophenecarboximidamide [Journal of Medicinal Chemistry, 23, 690–692 (1980)]; and N-(N-cyanoimidoyl)-sulfoximides [Chemisch Berichte, 121, 383–386 (1988)]. However, these compounds have been reported only as the intermediates in the production of anti-bacterial agents or diuretics and the intermediates in the production of thiatriazines, respectively, without descriptions of the vasodilating effect and hypotensive effect. Also, no carboximidamide compounds relating to the present invention which have an alkyl substituent in N'-position have hitherto been reported.

SUMMARY OF THE INVENTION

Summary

The present invention has been done for the purpose of providing a new compound having vasodilating effect. The present inventor has discovered that N-cyano-N'-substituted pyridinecarboximidamide derivatives and N-cyano-N'-substituted carboximidamide derivatives in which the N'-position is substituted with an alkyl substituent have the aforementioned effect and find out from these novel carboximidamide derivatives the ones which are effective as a potassium channel activating agent, a hypotensor, a therapeutic for the treatment of ischemic heart disease, a therapeutic for the treatment of peripheral circulatory failure, an ameliorants of cerebral circulation, a therapeutic for the treatment of thrombosis and an antasthmatic. The present invention has been accomplished on the basis of these discoveries.

In other words, the carboximidamide derivatives according to the present invention are represented by the following formula (A):

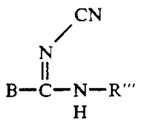
(A)

wherein when B is

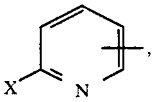

wherein X represents a hydrogen atom or a chlorine atom, R''' represents —$R^1$ or

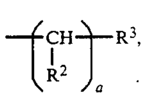

wherein $R^1$ represents an alkyl group,

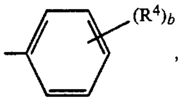
,
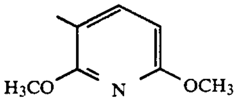

or an alkyl group having a nitroxyl group, wherein $R^4$ represents an alkyl group or an alkoxyl group and b denotes an integer of 0 or 1, and $R^2$ represents one or more members selected from the group consisting of an alkyl group, an aryl group, a nitroxyl group, an arylalkoxyl group, a hydroxyl group and a hydrogen atom and a denotes an integer of 1-3, provided that when a is an integer of 2 or more, two or more $R^2$'s may be the same or different members in the aforementioned group, and $R^3$ represents

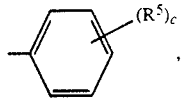
,
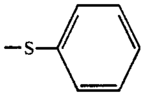
or
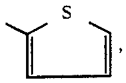

wherein $R^5$ represents one or more members selected from the group consisting of an alkyl group, an alkoxyl group, an arylalkoxyl group, a nitro group, an amino group, an alkylamino group, an arylalkylamino group, an alkylthio group, a perfluoroalkyl group or a halogen atom, and c denotes an integer of 0–5, provided that when c denotes an integer of 2 or more, two or more $R^5$'s may be the same or different members in the aforementioned group; and

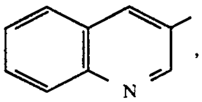
,
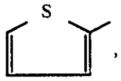
,
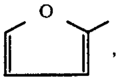
,
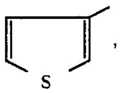
,
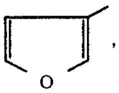
,
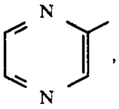
,
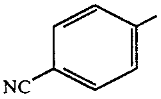
or $H_3C—S—$, R''' represents

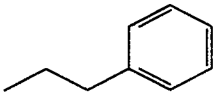
or
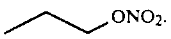

The present invention also relates to acid adduct salts thereof.

The compound according to the present invention includes the compound which has pyridine as the substituent B in the formula (A) and the compound having no pyridine.

The compound having pyridine as the substituent B is the pyridinecarboximidamide derivative represented by the following formula (I):

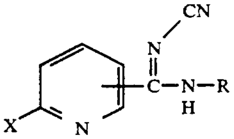
(I)

wherein

X represents a hydrogen atom or a chlorine atom; R represents —$R^1$ or

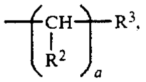

wherein $R^1$ represents an alkyl group,

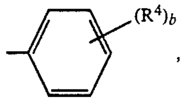, 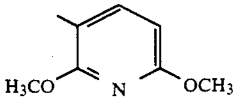

or an alkyl group having a nitroxyl group, wherein $R^4$ represents an alkyl group or an alkoxy group and b denotes an integer of 0–1, $R^2$ represents one or more members selected from the group consisting of an alkyl group, an aryl group, a nitroxyl group, an arylalkoxyl group, a hydroxyl group and a hydrogen atom, and a denotes an integer of 1–3, provided that when a is an integer of 2 or more, two or more $R^2$'s may be the same or different members in the aforementioned group, $R^3$ represents

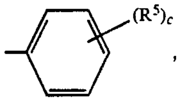, 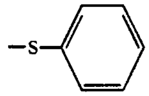 or 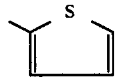, wherein $R^5$ represents one or more members selected from the group consisting of an alkyl group, an alkoxyl group, an arylalkoxyl group, a nitro group, an amino group, an alkylamino group, an arylalkylamino group, an alkylthio group, a perfluoroalkyl group or a halogen atom, c denotes an integer of 0–5, provided that when c denotes an integer of 2or more, two or more $R^5$'s may be the same or different members in the aforementioned group; or an acid adduct salt thereof.

The compound according to the present invention which has no pyridine as the substituent B is the carboximidamide derivative represented by the following formula (I'):

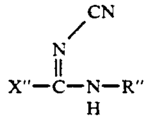 (I')

wherein X'' represents

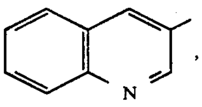, 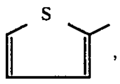, 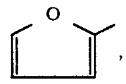,

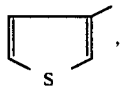, 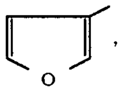, 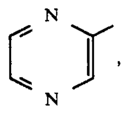,

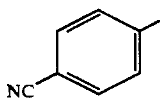 or $H_3C—S—$, and R'' represents

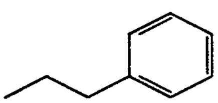 or 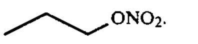.

The present invention also relates to the intermediate obtained in the course of the production of the compound represented by the formula (I). The N-cyanopyuridinecarboximidate compound which is the intermediate obtained in the course of the production of the compound of the present invention is represented by the following formula (II):

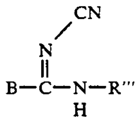 (A)

wherein X represents a hydrogen atom or a chlorine atom, and R' represents an alkyl group.

Furthermore, the present invention relates to the process for producing the compound represented by the formula (I).

That is to say, the process for producing the pyridinecarboximidamide derivative represented by the formula (I) set forth above is characterized in that a cyanopyridine compound represented by the following formula (III) is reacted with an alcohol and sodium hydride or a sodium alkoxide to form a compound represented by the following formula (IV), which is reacted with cyanamide in a buffer solution having a pH in the range of 5.0–6.0 to form an N-cyanopyridinecarboximidate compound represented by the above-described formula (II), which is further reacted with an amine compound represented by the formula $NH_2—R$, wherein R has the same meaning as defined above:

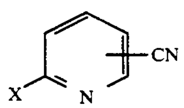 (III)

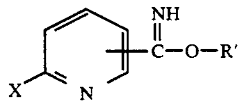 (IV)

wherein X represents a hydrogen atom or a chlorine atom, and R' represents an alkyl group.

The present invention also relates to the use of the carboximidamide derivatives represented by the above-described formula (A). In other words, the present invention relates to potassium channel activating agents, hypotensor, therapeutic agents of ischemic heat disease, therapeutic agents of peripheral circulatory failure, ameliorants of cerebral circulation, therapeutic agents of thrombosis and antasthmatics which contain the pyridinecarboximidamide derivative represented by the formula (I) or an acid adduct salt thereof as an effective ingredient, and hypotensors which contain as an active ingredient, and hypotensors which contain as an active ingredient the N-cyano-N'-substituted carboximidamide derivative wherein the N'-position is substituted by an alkyl group of an acid adduct salt thereof, and relates to the therapeutic methods for patients who need the treatments of potassium channel activation, the treatment of hypertension, the treatment of ischemic heart disease, the treatment of peripheral circulatory failure, the treatment of cerebral circulatory failure, the treatment of thrombosis and the asthma using the aforementioned N-cyano-N'-substituted pyridinecarboximidamide derivative or an acid adduct salt thereof, and the therapeutic method for patients who need hypotensive treatment using the N-cyano-N'-substituted carboximidamide derivative in which N'-position is substituted by an alkyl group or an acid adduct salts thereof.

Effect of the Invention

The carboximidamide derivatives according to the present invention have vasodilating effect and hypotensive effect, and the carboximidamide derivatives having a pyridine substituent have further potassium channel activating effect.

The carboximidamide derivatives according to the present invention have vasodilative effect and hypotensive effect, and the pyridinecarboximidamide derivatives have further potassium channel activating effect as described above. They also have coronary vasodilative effect, cardioprotective effect, peripheral blood vessel resistance decreasing effect, cerebral vasodilative effect, platelet aggregation inhibiting effect and bronchodilatative effect.

It should be extraordinary that the carboximidamide derivative according to the present invention has various physiological effects set forth above.

DETAILED DESCRIPTION OF THE INVENTION

The carboximidamide derivatives according to the present invention are represented by the formula (A) set forth above and include the N-cyano-N'-substituted pyridinecarboximidamide derivatives having pyridine as the substituent B and the N-cyano-N'-substituted carboximidamide derivatives having no pyridine, wherein respective substituents have the same meanings as defined above.

[I]N-cyano-N'-substituted-pyridinecarboximidamide derivatives

The pyridinecarboximidamide derivative according to the present invention is the N-cyano-N'-substituted-pyridinecarboximidamide derivative represented by the formula (I) set forth above (wherein respective substituents have the same meanings as defined above).

In the formula (I), the alkyl group of $R^1$ has preferably 1-10 carbon atoms, particularly 5-8 carbon atoms. It may be the alkyl group in a straight chain or a branched chain, preferably in a branched chain. The alkyl group having a nitroxyl group of $R^1$ is preferably the one having 1-5 carbon atoms, particularly 1-3 carbon atoms. In this case, one or more, preferably one or two, nitroxyl groups may be contained. The nitroxyl group may be bonded to either one of primary, secondary or tertiary carbon atoms, and particularly the nitroxyl group is desirably bonded to a primary carbon atom.

The alkyl group of $R^2$ has preferably 1-5 carbon atoms, particularly 1-3 carbon atoms. The aryl group is preferably a tolyl group, a xylyl group or a phenyl group, more preferably a phenyl group. The arylalkoxyl group is preferably a phenethyloxy group, a 3-phenylpropyloxy group or a benzyloxy group, more preferably a benzyloxy group.

When two or more $R^2$'s are simultaneously contained, these plural $R^2$'s may be the same or different members in the aforementioned group consisting of the groups and the atom set forth above. When $R^4$ is an alkyl group or an alkoxyl group, the alkyl or alkoxyl group preferably contains 1-5 carbon atoms, particularly 1-3 carbon atoms. $R^5$ represents one or more members selected from the aforementioned group as defined above. When two or more $R^5$'s are simultaneously contained, the $R^5$'s may be the same or different members in the group. When $R^5$ is an alkyl group or an alkoxyl group, the alkyl or alkoxyl group preferably contains 1-5 carbon atoms, particularly 1-3 carbon atoms. When $R^5$ is an arylalkoxyl group, the arylalkoxyl group is preferably a phenethyloxy group, a 3-phenylpropyloxy group or a benzyloxy group, particularly a benzyloxy group. The alkylamino group preferably contains 1-5 carbon atoms, preferably 1-3 carbon atoms. The arylalkylamino group is preferably a phenethylamino group, a 3-phenylpropylamino group or a benzylamino group, more preferably a benzylamino group. When $R^5$ is an alkylthio group or a perfluoroalkyl group, each of these groups preferably contains 1-5 carbon atoms, particularly 1-3 carbon atoms.

The halogen atom may be any of halogen atoms, and it is preferably fluorine, chlorine or bromine.

The aforementioned N-cyano-N'-substituted pyridinecarboximidamide derivative according to the present invention has a basic nitrogen atom and thus forms an acid adduct salt. Acids with which an acid adduct salt is formed include, for example, inorganic acids such as hydrochloric acid, sulfuric acid, nitric acid, phosphoric acid or the like; or organic acids such as acetic acid, propionic acid, maleic acid, oleic acid, palmitic acid, citric acid, succinic acid, tartaric acid, fumaric acid, glutamic acid, pantothenic acid, laurylsulfonic acid or the like. It is needless to say that when an acid adduct salt is used as a medicine, the acid must be the one which is pharmaceutically acceptable.

As the representative examples of the N-cyano-N'-substituted-pyridinecarboximidamide derivative according to the present invention represented by the formula (I), there are mentioned the following compound [compound Nos. (1)-(53)]:

| Compound No. | Name of Compound |
|---|---|
| (1) | N-cyano-N'-(2-nitroxyethyl)-2-pyridinecarboximidamide |
| (2) | N-cyano-N'-(2,2-dimethylpropyl)-2-pyridinecarboximidamide |
| (3) | N-cyano-N'-(1,2,2-trimethylpropyl)-2-pyridinecarboximidamide |
| (4) | N-cyano-N'-phenyl-2-pyridinecarboximidamide |
| (5) | N-cyano-N'-(4-methoxyphenyl)-2-pyridinecarboximidamide |
| (6) | N-cyano-N'-(4-methylbenzyl)-2-pyridinecarboximidamide |
| (7) | N-cyano-N'-(4-chlorobenzyl)-2-pyridinecarboximidamide |
| (8) | N-cyano-N'-[4-(trifluoromethyl)benzyl]-2-pyridinecarboximidamide |
| (9) | N-cyano-N'-[2-(4-methylphenyl)ethyl]-2-pyridinecarboximidamide |
| (10) | N-cyano-N'-[2-(4-chlorophenyl)ethyl]-2-pyridinecarboximidamide |
| (11) | N-cyano-N'-(2-hydroxy-1-methyl-2-phenylethyl)-2-pyridinecarboximidamide |
| (12) | N-cyano-N'-(2-thienylmethyl)-2-pyridinecarboximidamide |
| (13) | N-cyano-N'-(2-nitroxyethyl)-3-pyridinecarboximidamide |
| (14) | N-cyano-N'-(3-nitroxypropyl)-3-pyridinecarboximidamide |
| (15) | N-cyano-N'-(3,3-dimethylbutyl)-3-pyridinecarboximidamide |
| (16) | N-cyano-N'-(4-methylphenyl)-3-pyridinecarboximidamide |
| (17) | N-cyano-N'-benzyl-3-pyridinecarboximidamide |
| (18) | N-cyano-N'-(4-methylbenzyl)-3-pyridinecarboximidamide |
| (19) | N-cyano-N'-(4-methoxybenzyl)-3-pyridinecarboximidamide |
| (20) | N-cyano-N'-(4-dimethylaminobenzyl)-3-pyridinecarboximidamide |
| (21) | N-cyano-N'-[4-(trifluoromethyl)benzyl]-3- |

-continued

| Compound No. | Name of Compound |
|---|---|
| | pyridinecarboximidamide |
| (22) | N-cyano-N'-(4-chlorobenzyl)-3-pyridinecarboximidamide |
| (23) | N-cyano-N'-(4-nitrobenzyl)-3-pyridinecarboximidamide |
| (24) | N-cyano-N'-(3,4-dichlorbenzyl)-3-pyridinecarboximidamide |
| (25) | N-cyano-N'-[3,5-bis(trifluoromethyl)benzyl]-3-pyridinecarboximidamide |
| (26) | N-cyano-N'-(3-benzyloxybenzyl)-3-pyridinecarboximidamide |
| (27) | N-cyano-N'-(2-phenylethyl)-3-pyridinecarboximidamide |
| (28) | N-cyano-N'-[2-(2-methoxyphenyl)ethyl]-3-pyridinecarboximidamide |
| (29) | N-cyano-N'-[2-(2-chlorophenyl)ethyl]-3-pyridinecarboximidamide |
| (30) | N-cyano-N'-[2-(4-chlorophenyl)ethyl]-3-pyridinecarboximidamide |
| (31) | N-cyano-N'-[2-(4-benzylaminophenyl)ethyl]-3-pyridinecarboximidamide |
| (32) | N-cyano-N'-[2-(4-nitrophenyl)-2-nitroxyethyl]-3-pyridinecarboximidamide |
| (33) | N-cyano-N'-(3-phenylpropyl)-3-pyridinecarboximidamide |
| (34) | N-cyano-N'-diphenylmethyl-3-pyridinecarboximidamide |
| (35) | N-cyano-N'-(1,2-diphenylethyl)-3-pyridinecarboximidamide |
| (36) | N-cyano-N'-(2,2-diphenylethyl)-3-pyridinecarboximidamide |
| (37) | N-cyano-N'-(3,3-diphenylpropyl)-3-pyridinecarboximidamide |
| (38) | N-cyano-N'-(2-benzyloxy-2-phenylethyl)-3-pyridinecarboximidamide |
| (39) | N-cyano-N'-[2-(3,4-dibenzyloxyphenyl)ethyl]-3-pyridinecarboximidamide |
| (40) | N-cyano-N'-3-(2,6-dimethoxypyridine)-3-pyridinecarboximidamide |
| (41) | N-cyano-N'-(2-nitroxyethyl)-4-pyridinecarboximidamide |
| (42) | N-cyano-N'-(3-nitroxypropyl)-4-pyridinecarboximidamide |
| (43) | N-cyano-N'-phenyl-4-pyridinecarboximidamide |
| (44) | N-cyano-N'-(3,4-dichlorobenzyl)-4-pyridinecarboximidamide |
| (45) | N-cyano-N'-(4-methylthiobenzyl)-4-pyridinecarboximidamide |
| (46) | N-cyano-N'-(3-benzyloxybenzyl)-4-pyridinecarboximidamide |
| (47) | N-cyano-N'-[2-(4-chlorophenyl)ethyl]-4-pyridinecarboximidamide |
| (48) | N-cyano-N'-[2-(2-methoxyphenyl)ethyl]-4-pyridinecarboximidamide |
| (49) | N-cyano-N'-(2-phenylthioethyl)-4-pyridinecarboximidamide |
| (50) | N-cyano-N'-[2-(4-nitrophenyl)-2-nitroxyethyl]-4-pyridinecarboximidamide |
| (51) | N-cyano-N'-[1-methyl-2-(4-nitrophenyl)-2-nitroxyethyl]-4-pyridinecarboximidamide |
| (52) | N-cyano-N'-(2-nitroxyethyl)-3-(6-chloropyridine)carboximidamide |
| (53) | N-cyano-N'-(2-phenylethyl)-3-(6-chloropyridine)carboximidamide |

The substituents R of these compounds have the following structures:

| Compound No. | —R |
|---|---|

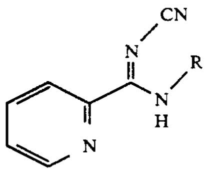

-continued

| Compound No. | —R |
|---|---|
| (1) | 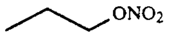 |
| (2) | 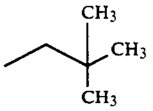 |
| (3) | 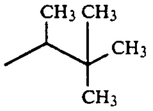 |
| (4) | 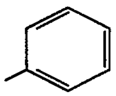 |
| (5) | 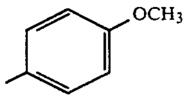 |
| (6) | 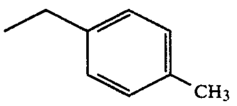 |
| (7) | 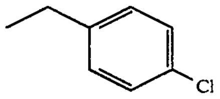 |
| (8) | 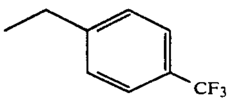 |
| (9) | 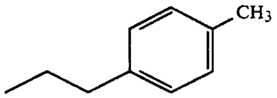 |
| (10) | 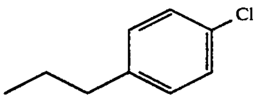 |
| (11) | 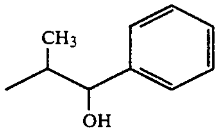 |
| (12) | 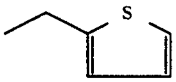 |

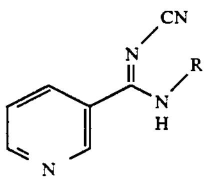

-continued
| Compound No. | —R |
|---|---|
| (13) | 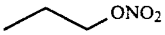 |
| (14) | 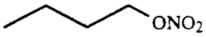 |
| (15) | 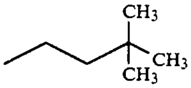 |
| (16) | 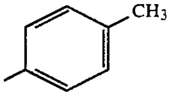 |
| (17) | 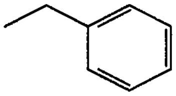 |
| (18) | 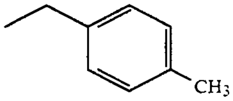 |
| (19) | 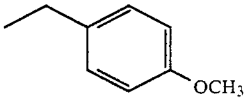 |
| (20) | 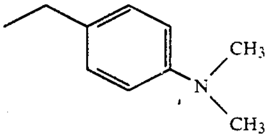 |
| (21) | 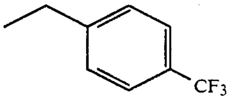 |
| (22) | 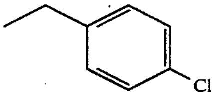 |
| (23) | 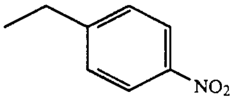 |
| (24) | 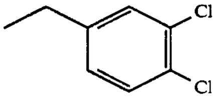 |
| (25) | 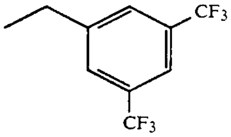 |
-continued
| Compound No. | —R |
|---|---|
| (26) | 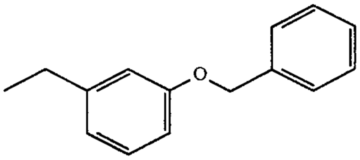 |
| (27) | 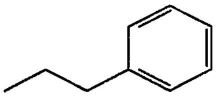 |
| (28) | 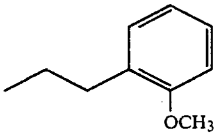 |
| (29) | 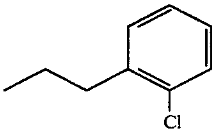 |
| (30) | 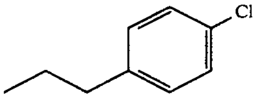 |
| (31) | 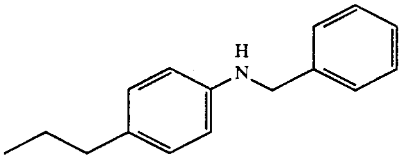 |
| (32) | 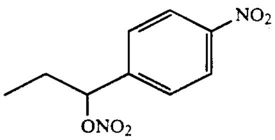 |
| (33) | 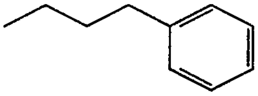 |
| (34) | 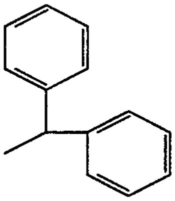 |
| (35) | 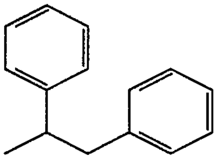 |

-continued

| Compound No. | —R |
|---|---|
| (36) | 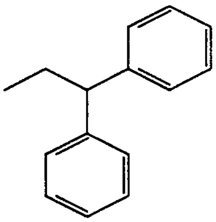 |
| (37) | 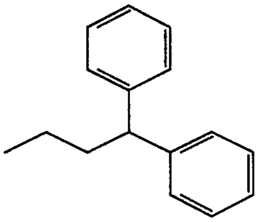 |
| (38) | 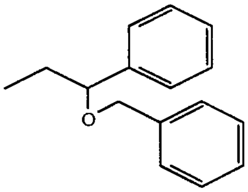 |
| (39) | 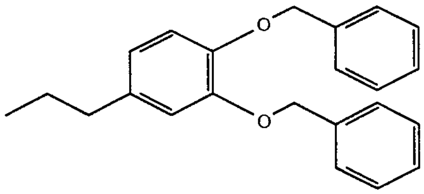 |
| (40) | 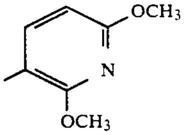 |
| | 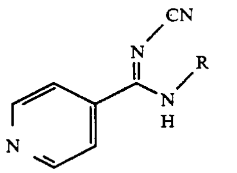 |
| (41) | 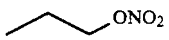 |
| (42) | 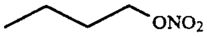 |
| (43) | 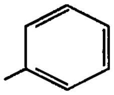 |
| (44) | 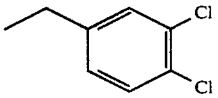 |

-continued

| Compound No. | —R |
|---|---|
| (45) | 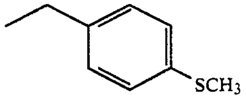 |
| (46) | 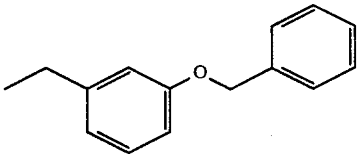 |
| (47) | 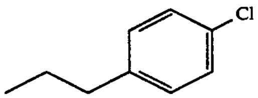 |
| (48) | 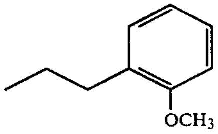 |
| (49) | 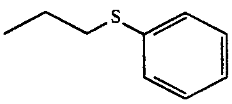 |
| (50) | 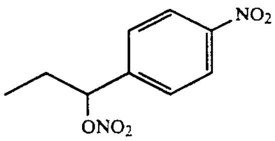 |
| (51) | 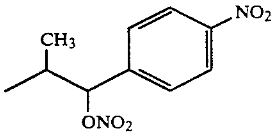 |
| | 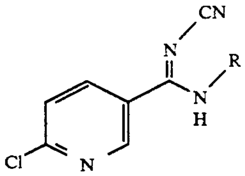 |
| (52) | 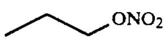 |
| (53) | 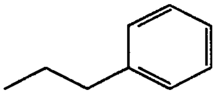 |

[II] N-cyano-pyridinecarboximidate compounds

The N-cyano-pyridinecarboximidate compound is the alkyl N-cyano-pyridinecarboximidate compound represented by the formula (II) set forth above, and it is an intermediate for producing the compound of the present invention represented by the formula (I) or an acid adduct salt thereof (wherein the meanings of respective substituents are defined above).

In the aforementioned formula (II), the alkyl group of R' has preferably 1-8 carbon atoms, more preferably 1-5 carbon atoms, which may be the chain or cycle in form, particularly an isopropyl group.

As the representative examples of the alkyl N-cyanopyridinecarboximidate compounds of the present invention represented by the formula (II), there are mentioned the following compounds [compound Nos. (54)-(58)]:

| Compound No. | Name of Compound |
|---|---|
| (54) | Methyl N-cyano-2-pyridinecarboximidate |
| (55) | Isopropyl N-cyano-2-pyridinecarboximidate |
| (56) | Isopropyl N-cyano-3-pyridinecarboximidate |
| (57) | Isopropyl N-cyano-4-pyridinecarboximidate |
| (58) | Isopropyl N-cyano-3-(6-chloropyridine)-carboximidate |

These compounds have the following structures:

| Compound No. | Structural Formula |
|---|---|
| (54) | 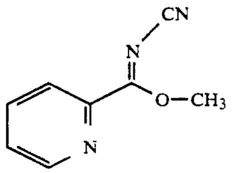 |
| (55) | 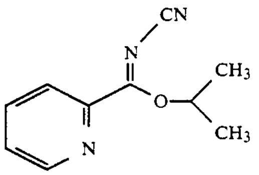 |
| (56) | 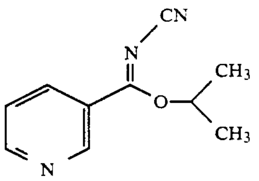 |
| (57) | 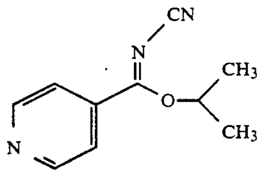 |
| (58) | 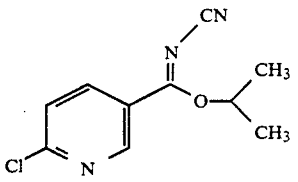 |

[III] Process for producing N-cyano-N'-substituted pyridinecarboximidamide derivatives (1) Summary The N-cyano-N'-substituted-pyridinecarboximidamide derivative according to the present invention can be produced by any methods suitable for the purpose, for example by the following two production methods. These production methods are illustrated by the reaction scheme (i) and the reaction scheme (ii), respectively.

That is to say, there are mentioned a method for producing the object compound, N-cyano-N'-substituted-pyridinecarboximidamide derivative represented by the formula (I), as is illustrated in the reaction scheme (i), by leading the cyanopyridine compound represented by the formula (III) to the N-cyano-pyridinecarboximidate compound represented by the formula (II), which is further reacted with any of various amine compounds (method i), and a method for producing the object compound, as is illustrated in the reaction scheme (ii), by converting the amide compound represented by the formula (V) which is prepared by a well-known method to the thioamide compound represented by the formula (VI), which is reacted with cyanamide ($NH_2CN$) in the presence of phosphorus oxychloride and a tertiary amine (method ii).

However, a compound containing a nitroxyl group in R cannot be produced by the method (ii).

These methods (i) and (ii) are described in detail below.

Reaction scheme (i):

(III)

(IV)

(II)

(I)

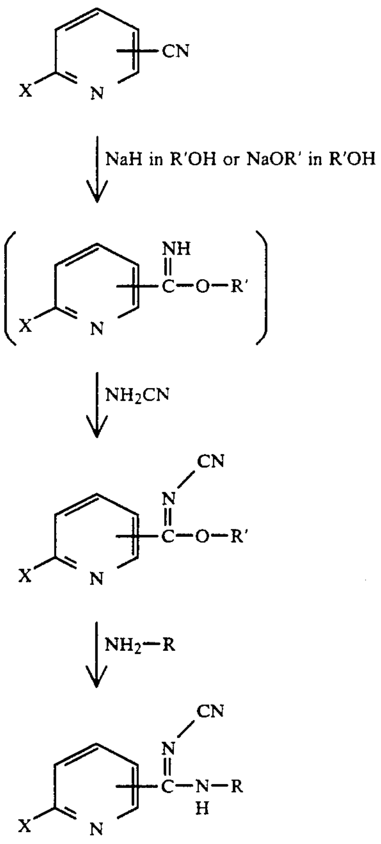

Wherein R, R' and X have the same meanings as defined above.

Reaction scheme (ii):

(V)

(VI)

(I)

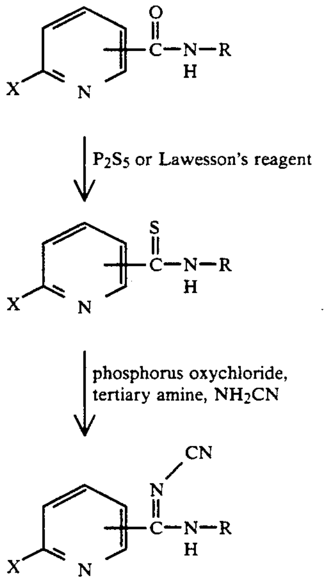

Wherein R and X have the same meanings as defined above.

(2) Method (i)

The method (i) is, as described above, a method for producing the object compound according to the reaction scheme (i).

(a) Compound (III)→Compound (IV)

The cyanopyridine compound represented by the formula (III) is reacted with sodium hydride or R'ONa corresponding to R'OH used, i.e. sodium alkoxide, in R'OH, i.e. an alcohol to form an imidate compound represented by the formula (IV). The amount of sodium hydride or R'ONa used in the reaction is a catalytic amount, and the reaction is generally carried out by using sodium hydride or R'ONa preferably in an amount of 0.01–0.5 mole, more preferably 0.02–0.2 mole in proportion to 1 mole of the cyanopyridine.

Alcohols (R'OH) which can be used in the reaction include chain and cyclic alcohols such as methanol, ethanol, n-propanol, isopropanol, n-butanol, isobutanol, t-butanol, cyclopentanol, cyclohexanol, n-octanol and the like.

The alcohol can be used also as a reaction solvent and can be used as only a reagent in the presence of other solvents. When the alcohol is used as a reaction solvent, it is generally used in an amount of 10–50 moles in proportion to 1 mole of the cyanopyridine. When the alcohol is used in the presence of other solvents, it is preferably used in an amount of 1–5 moles in proportion to 1 mole of the cyanopyridine. The solvents which can be used in the reaction desirably include aprotic solvents such as hexane, benzene, toluene, diethyl ether, petroleum ether, tetrahydrofuran, N,N-dimethylformamide and the like. The reaction temperature is preferably in the range of 0°–50° C., particularly around room temperature.

Under the aforementioned reaction conditions, the reaction can be completed in 3–24 hours.

The resulting imidate compound represented by the formula (IV) can immediately be used in the next reaction without purification by isolation.

(b) Compound (IV)→Compound (II)

The imidate compound represented by the formula (IV) is reacted with cyanamide ($NH_2CN$) in a buffer solution, preferably in a phosphate buffer solution to be converted into the N-cyano-pyridinecarboximidate compound represented by the formula (II).

The amount of the cyanamide is preferably at least 1 mole or more, particularly 2–3 moles in proportion to 1 mole of the imidate compound represented by the formula (IV). The reaction is conducted in a buffer solution, preferably in a phosphate buffer solution, and the pH is preferably in the range of 5.0–6.0, more preferably in the range of 5.2–5.6. The concentration of the buffer solution is preferably in the range of 0.5–4 M. When a phosphate buffer solution is used, each of the components of the buffer solution, $Na_2HPO_4$ and $NaH_2PO_4$, is preferably used in an amount of at least 1 mole or more to 1 mole of the imidate compound represented by the formula (IV) in order to maintain sufficient bufferizing ability. The reaction temperature is preferably in the range of 0°–50° C., particularly around room temperature.

Under such reaction conditions as above, the imidate compound represented by the formula (IV) is generally converted into the N-cyano-pyridinecarboximidate compound represented by the formula (II) in 2–12 hours.

As the method for purification by isolation of the N-cyano-pyridinecarboximidate compound represented by the formula (II) thus obtained, there can be used purification methods which are well known in the art of organic synthetic chemistry such as a crystallization method, a distillation method, a column chromatography method with a carrier of silica gel and the like. (c) Compound (II)→Compound (I)

The N-cyano-N'-substituted-pyridinecarboximidamide compound represented by the formula (I) can be produced by reacting the N-cyano-pyridinecarboximidate compound represented by the formula (II) with any of various amine compounds.

The amine compound is preferably used in an amount of at least 1 mole or more, more preferably in the range of 1–2 moles to 1 mole of the N-cyanopyridinecarboximidate compound represented by the formula (II). The reaction is usually conducted in a solvent. As the solvents which can be used in the reaction, there can be mentioned, for example, methanol, ethanol, dichloromethane, chloroform, carbon tetrachloride, dioxane, tetrahydrofuran, water and the like, particularly methanol. The reaction temperature is in the range from 0° C. to the boiling point of the solvent, preferably around room temperature.

Under such reaction conditions as above, the reaction can be completed in 5 minutes–24 hours.

The methods for purification by isolation of the compound represented by the formula (I) from the reaction mixture obtained in the aforementioned reaction are the same as those set forth in the stage of the purification by isolation of the N-cyano-pyridinecarboximidate compound represented by the formula (II).

The compound of the present invention represented by the formula (I) can be converted into an acid adduct salt thereof according to a method which is well-known per se. The acids which can be converted into acid adduct salts are the same as defined above.

(3) Method (ii)

(a) Compound (V)→Compound (VI)

The amide compound represented by the formula (V) which is prepared by a well-known method is converted into the thioamide compound represented by the formula (VI) with a well-known thiocarbonylation reagent such as $P_2S_5$ or a Lawesson's reagent in a well-known method [see Tetrahedron, 35, 2433 (1979)].

(b) Compound (VI)→Compound (I)

The thioamide compound represented by the formula (VI) can be reacted with cyanamide ($NH_2CN$) in the presence of phosphorus oxychloride and a tertiary amine to prepare the N-cyano-N'-substituted-pyridinecarboximidamide compound represented by the formula (I). In the reaction, cyanamide ($NH_2CN$) can be used in an amount of at least 1 mole or more, preferably 3 moles or more, more preferably in the range of 5–15 moles in proportion to 1 mole of the thioamide compound represented by the formula (VI).

While the reaction is, as described above, conducted in the presence of phosphorus oxychloride, the reaction can be performed in the same manner not only with phosphorus oxychloride but also with phosphorus pentoxide, phosphorus pentachloride, thionyl chloride, sulfuryl chloride or the like. Such an reagent is desirably used in an amount of at least 1 mole or more, preferably in the range of 1–2 moles in proportion to 1 mole of the thioamide compound represented by the formula (VI). The reaction is also conducted in the coexistence of a tertiary amine. As the tertiary amine, triethylamine, diisopropylethylamine or the like is suitable. The tertiary amine is preferably used in an amount of 1–2 moles to 1 mole of the thioamide compound represented by the formula (VI).

The reaction is usually carried out in a solvent, and the solvents which can be used include acetonitrile, benzene, hexane, toluene, dichloromethane, chloroform, carbon tetrachloride, dioxane, tetrahydrofuran, N,N-dimethylformamide and the like, and acetonitrile is particularly preferred.

The reaction temperature is preferably in the range from room temperature to the boiling temperature of the solvent used, particularly in the range of 80°–110° C.

Under such reaction conditions, the reaction can be completed in 6–24 hours.

The method of purifying the N-cyano-N'-substituted pyridinecarboximidamide compound as the object compound from the reaction mixture thus obtained and the method of forming an acid adduct salt are the same as those set forth in the description of the method (i).

[IV] -Use of the Compound [Pyridinecarboximidamide Derivative Represented by the Formula (I)]

(1) Potassium Channel Activating Agent

The compound of the present invention represented by the formula (I) has, as shown in the result of Referential Example 1)-2 below, potassium channel activating effect and thus is useful as a potassium channel activating agent.

(2) Hypotensor

The compound of the present invention exhibited, as shown in the results of Referential Examples 1)-3 and 1)-4, strong hypotensive effect in either of the intravenous or oral administration of the compound in spontaneous hypertensive rats. Moreover, the compound decreased in the blood pressure even at a low dose to a dog, as shown in Referential Example 1)-5. Thus, the compound of the present invention is useful as a hypotensor.

(3) Therapeutic agent for the treatment of ischemic heart disease

The compound of the present invention significantly increased coronary blood flow in a heart isolated from a rat as compared with nicorandil as shown in Referential Example 1)-6. The compound of the present invention exhibited hypotensive effect and continuous coronary blood flow increasing effect by far stronger than nicorandil as shown in Referential Example 1)-7. Moreover, these effects were continuously observed on intraduodenally administering the compound in Referential Example 1)-8.

The compound represented by the formula (I) exhibited strong inhibitory effect on a rhythmic contraction induced by 3,4-DAP as a model of pseudoangina pectoris in Referential Example 1)-9, and it was also more effective than nicorandil in an angina pectoris model of rat, as shown in Referential Example 1)-10. Moreover, it was recognized from the result of Referential Example 1)-11 that the compound represented by the formula (I) also exhibited the cardioprotective effect after ischemia-reperfusion.

As apparent from the above-described results, the compound of the present invention represented by the formula (I) is useful as a therapeutic agent for the treatment of ischemic heart diseases such as angina pectoris, myocardiac infarction or the like.

(4) Therapeutic Agent for Ameliorant of Peripheral Circulation

The compound represented by the formula (I) decreased the total peripheral resistance by intraduodenal administration, as shown in Referential Example 1)-8. As apparent from the result, the compound of the present invention represented by the formula (I) is useful as an ameliorant of peripheral circulation.

(5) Therapeutic Agent for Ameliorant of Cerebral Circulation

The compound represented by the formula (I) was found to exhibit cerebral vasodilatative effect from the result of Referential Example 1)-12 and the effect of prolonging the survival time in hypoxia from the result of Referential Example 1)-13. As apparent from these results, the compound of the present invention represented by the formula (I) is useful as an ameliorant of cerebral circulation.

(6) Therapeutic Agent of Thrombosis

The compound represented by the formula (I) inhibited the aggregation of platelets and promoted the dissociation thereof as shown in Referential Example 1)-14. As apparent from the result, the compound of the present invention represented by the formula (I) is useful as a therapeutic agent for the treatment of thrombosis.

(7) Antasthmatic

The compound represented by the formula (I) dilated not only the smooth muscle of blood vessel but also the smooth muscle of trachea as shown in Referential Example 1)-15. As apparent from the result, the compound of the present invention represented by the formula (I) is useful as an antasthmatic.

When the compound represented by the formula (I) is administered as a hypotensor, a therapeutic agent for the treatment of ischemic heart diseases, an ameliorant of peripheral circulation, an ameliorant of cerebral circulation, a therapeutic agent for the treatment of thrombosis or an antasthmatic, it can be administered orally, parenterally (intramuscularly, intravenously, subcutaneously or percutaneously), or in the form of a sublingual tablet or a suppository.

It is needless to say that the dose and the dosing way of the compound represented by the formula (I) vary depending on the states of a patient such as body weight, sex, sensitivity, dosage time, drugs to be used in combination, patients or the seriousness of the patients. The suitable dose and dosage times under a certain condition must be determined on the basis of the above-described principles by the suitable dose determining test by medical specialists. The dose is generally in the range of about 0.1-200 mg, preferably 0.1-100 mg, particularly 0.5-30 mg per day for an adult patient.

When the compound represented by the formula (I) is administered orally as a drug, it is administered in the form of tablets, granules, powder or capsules. When it is administered parenterally, it is administered in the form of injections or suspensions. In order to produce these pharmaceutical preparations, excipients, binding agents, disintegrating agents, lubricants, stabilizers and the like can be added. If necessary, other drugs can be mixed.

The excipients include, for example, lactose, starch, crystalline cellulose, mannitol, maltose, calcium hydrogen phosphate, light anhydrous silicic acid, calcium carbonate and the like; binding agents include, for example, starch, polyvinylpyrrolidone, hdroxypropylcellulose, ethylcellulose, carboxymethylcellulose, gum arabic and the like; disintegrating agents include, for example, starch, calcium carboxymethylcellulose and the like; lubricants include, for example, magnesium stearate, talc, hardened oils and the like; and stabilizing agents include, for example, lactose, mannitol, maltose, Polysorbates, Macrogols, polyoxyethylene hardened castor oil or the like.

The pharmaceutical preparations can be produced in the dosage forms of tablets, granules, capsules, injections or the like with these ingredients.

[IV] N-Cyano-N'-Substituted-Carboximidamide Derivatives

The carboximidamide derivative of the present invention which having no pyridine as the substituent B in the formula (A) set forth above is, as described above, the N-cyano-N'-substituted-carboximidamide derivative represented by the following formula (I') as described above:

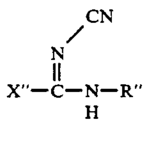

(I')

wherein X" represents

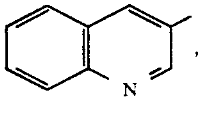
,
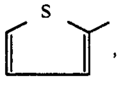
,
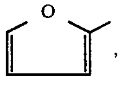
,

-continued

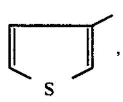
,
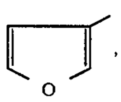
,
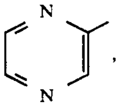
,

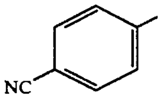
or $H_3C$—S—, and R" represents

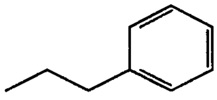
or
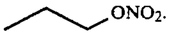
.

When X" is
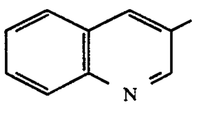
or
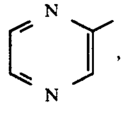
, the compound represented by the formula (I') can form its acid adduct salts. The acids with which acid adduct salts are formed include the same acids as in the case of the N-cyano-N'-substituted-pyridinecarboximidamide derivatives. In this connection, it is needless to say that when the acid adduct salt is used as a drug, the acid must be the one which is pharmaceutically acceptable.

Representative examples of the N-cyano-N'-substituted-carboximidamide derivative of the present invention represented by the formula (I') include the following representative compounds [compound Nos. (59)-(70)]:

| Compound No. | Name of Compound |
|---|---|
| (59) | N-cyano-N'-(2-nitroxyethyl)-3-quinolinecarboximidamide |
| (60) | N-cyano-N'-(2-phenylethyl)-3-quinolinecarboximidamide |
| (61) | N-cyano-N'-(2-nitroxyethyl)pyrazinecarboximidamide |
| (62) | N-cyano-N'-(2-nitroxyethyl)-2-furfancarboximidamide |
| (63) | N-cyano-N'-(2-phenylethyl)-2-furancarboximidamide |
| (64) | N-cyano-N'-(2-nitroxyethyl)-3-furancarboximidamide |
| (65) | N-cyano-N'-(2-phenylethyl)-3-furancarboximidamide |
| (66) | N-cyano-N'-(2-nitroxyethyl)-2-thiophenecarboximidamide |
| (67) | N-cyano-N'-(2-phenylethyl)-2-thiophenecarboximidamide |
| (68) | N-cyano-N'-(2-phenylethyl)-3-thiophenecarboximidamide |
| (69) | N-cyano-N'-(2-phenylethyl)-4-cyanobenzenecarboximidamide |
| (70) | 3-Cyano-2-methyl-1-(2-nitroxyethyl)-isothiourea |

These compounds have the following structures, respectively.

| Compound No. | Structure |
|---|---|
| (59) | 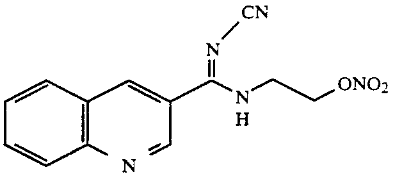 |
| (60) | 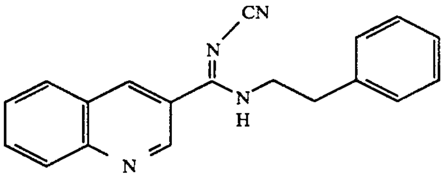 |
| (61) | 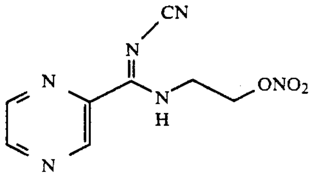 |
| (62) | 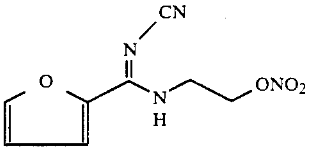 |
| (63) | 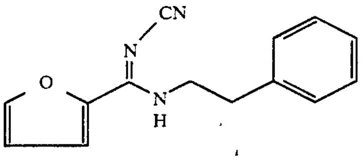 |
| (64) | 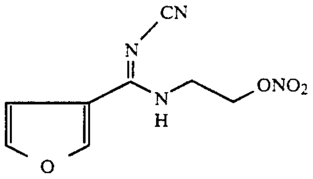 |
| (65) | 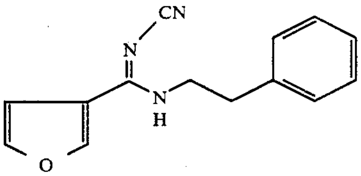 |
| (66) | 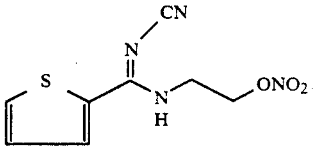 |
| (67) | 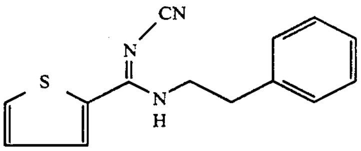 |

-continued

| Compound No. | Structure |
|---|---|
| (68) | 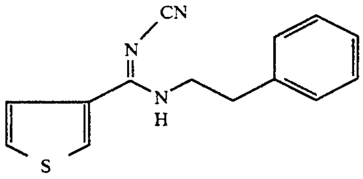 |
| (69) | 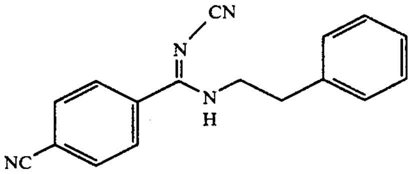 |
| (70) | 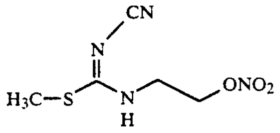 |

[V] Process for Producing N-cyano-N'-Substituted-Carboximidamide Derivatives

The N-cyano-N'-substituted-carboximidamide derivatives according to the present invention represented by the formula (I') can be prepared by any methods suitable for the purpose such as the methods (i') and (ii') described below.

(1) Method (i')

The carboximidamide derivatives of the present invention represented by the formula (I') except those in which X'' is $H_3C—S—$ such as 3-cyano-2-methyl-1-(2-nitroxyethyl)isothiourea can be obtained, as illustrated by the reaction scheme (i'), by converting the nitrile represented by the formula (II') into the cyanoimidate compound represented by the formula (IV'), which is then reacted with an amine compound. Thus, the N-cyano-N'-substituted-carboximidamide derivative represented by the formula (I') as the object compound can be obtained.

Reaction scheme (i'):

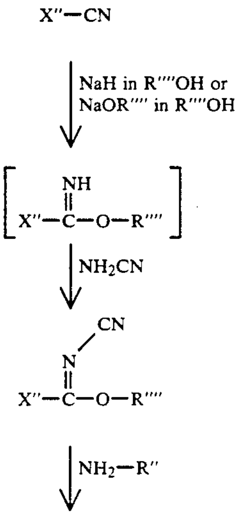

(II')

(III')

(IV')

-continued

Reaction scheme (i'):

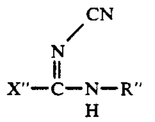

(I')

wherein R'''' represents an alkyl group, and X'' and R'' have the same meanings as defined above.

The production method is further described in detail below referring to the reaction scheme (i').

(a) Compound (II')→Compound (III')

The nitrile compound represented by the formula (II') is reacted with sodium hydride or R''''ONa corresponding to R''''OH used, i.e. sodium alkoxide, in R''''OH, i.e. an alcohol to form the imidate compound represented by the formula (III'). The amount of sodium hydride or R''''ONa used in the reaction is a catalytic amount, and the reaction is generally carried out by using sodium hydride or R''''ONa preferably in an amount of 0.01–0.5 mole, more preferably 0.02–0.2 mole in proportion to 1 mole of the nitrile.

Alcohols (R''''OH) which can be used in the reaction include either chain or cyclic alcohols such as methanol, ethanol, n-propanol, isopropanol, n-butanol, isobutanol, t-butanol, cyclopentanol, cyclohexanol, n-octanol and the like. The alcohol can be used also as a reaction solvent and can be used as only a reagent in the coexistence of other solvents. When the alcohol is used as a reaction solvent, it is generally used in an amount of 10–50 moles in proportion to 1 mole of the nitrile. When the alcohol is used in the presence of other solvents, it is preferably used in an amount of 1–5 moles in proportion to 1 mole of the nitrile. The solvents which can be used desirably include aprotic solvents such as hexane, benzene, toluene, diethyl ether, petroleum ether, tetrahydrofuran and the like. The reaction temperature is preferably in the range of 0°–50° C., particularly around room temperature.

Under the aforementioned reaction conditions, the reaction can be completed usually in 0.5–28 hours.

The resulting imidate compound represented by the formula (III') can be immediately used in the next reaction without purification by isolation.

(b) Compound (III')→Compound (IV')

The imidate compound represented by the formula (III') is reacted with cyanamide ($NH_2CN$) in a buffer solution, preferably in a phosphate buffer solution to be converted into the cyanoimidate compound represented by the formula (IV').

The amount of the cyanamide is preferably at least 1 mole or more, particularly 2–3 moles in proportion to 1 mole of the imidate compound. The reaction is conducted in a buffer solution, preferably in a phosphate buffer solution, and the pH is preferably in the range of 5.0–6.5, more preferably in the range of 5.2–6.2. The concentration of the buffer solution is preferably in the range of 0.5–4 M, particularly 1–3 M. When a phosphate buffer solution is used, each of the components of the buffer solution, for example, $Na_2HPO_4$ and $NaH_2PO_4$, is preferably used in an amount of at least 1 mole or more to 1 mole of the imidate compound in order to maintain sufficient bufferizing ability. The reaction temperature is preferably in the range of 0°–50° C., particularly around room temperature.

Under such reaction conditions as above, the imidate compound represented by the formula (III') is generally converted into the cyanoimidate compound represented by the formula (IV') in 2–75 hours.

As the method for purification by isolation of the cyanoimidate compound represented by the formula (IV') thus obtained, there can be used purification methods which are well-known in the art of organic synthetic chemistry such as a crystallization method, a distillation method, a column chromatography method with a carrier of silica gel and the like.

(c) Compound (IV')→Compound (I')

The N-cyano-N'-substituted-carboximidamide derivative represented by the formula (I') can be produced by reacting the cyanoimidate compound represented by the formula (IV') with one of various amine compounds.

The amine compound is preferably used in an amount of at least 1 mole or more, more preferably in the range of 1–2 moles to 1 mole of the cyanoimidate compound represented by the formula (IV'). The reaction is usually conducted in a solvent. As the solvents which can be used in the reaction, there can be mentioned, for example, methanol, ethanol, dichloromethane, chloroform, carbon tetrachloride, dioxane, tetrahydrofuran and the like, particularly methanol. The reaction temperature is in the range from 0° to the boiling point of the solvent, preferably around room temperature.

Under such reaction conditions as above, the reaction generally can be completed in 5 minutes–50 hours.

The methods for purification by isolation of the e compound represented by the formula (I') from the reaction mixture obtained in the aforementioned reaction are the same as those set forth in the stage of the purification by isolation of the cyanoimidate compound represented by the formula (IV').

(2) Method (ii')

Among the compound of the present invention, 3-cyano-2-methyl-1-(2-nitroxyethyl)isothiourea can be prepared by reacting the dimethyl N-cyanodithioiminocarbonate represented by the formula (V') with 2-nitroxyethylamine, as shown in the following reaction scheme (ii').

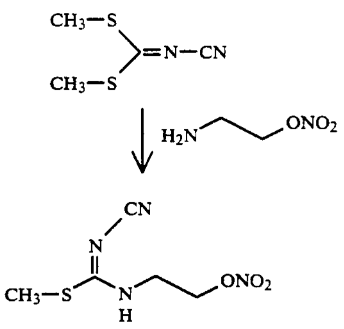

(V')

The amount of 2-nitroxyethylamine which is used in the reaction is preferably at least 1 mole or more, particularly 1–2 moles per mole of dimethyl N-cyanodithioiminocarbonate represented by the formula (V'). The reaction is usually conducted in a solvent, and the solvents which can be used in the reaction preferably include alcohols such as methanol, ethanol, isopropanol and the like, and aprotic solvents such as chloroform, dichloromethane, tetrahydrofuran, benzene, toluene and the like. The reaction temperature is preferably in the range from the solidifying point of the solvent to 50° C., preferably around room temperature. Under such reaction conditions set forth above, the reaction can be completed in 1-30 hours.

The methods for purification by isolation of 3-cyano-2-methyl-1-(2-nitroxyethyl)isothiourea from the reaction mixture obtained in the aforementioned reaction are the same as those set forth in the stage of the purification by isolation of the cyanoimidate compound represented by the formula (IV'), and purification methods well-known in the art of organic synthetic chemistry such as a crystallization method, a distillation method, a chromatographical method with a carrier of silica gel can be used.

Among the compounds of the present invention represented by the formula (I'), the compound which has basic nitrogen atom can be converted into its acid adduct salt by a method which is well-known per se. The acids with which the acid adduct salts can be formed are the same as described above.

[VI] Use of the Compounds [Carboximidamide Derivatives Represented by the Formula (I')]

The compound of the present invention represented by the formula (I') has, as shown in the results of Referential Examples 2)-1 and 2)-2 below, vasodilative effect and hypotensive effect and thus is useful as a vasodilative agent and a hypotensor.

When the compound represented by the formula (I') is administered as a vasodilator or a hypotensor, it can be administered orally, parenterally (intramuscularly, intravenously, subcutaneously or percutaneously), or in the form of a sublingual tablet or a suppository.

It is needless to say that the dose and the dosing route of the compound represented by the formula (I') vary depending on the states of a patient such as body weight, sex, sensitivity, dosage time, drugs to be used in combination, patients or the seriousness of the patients. The suitable dose and dosage times under a certain condition must be determined on the basis of the above-described principles by the suitable dose determining test by medical specialists. The dose is generally in the range of about 0.1-200 mg, preferably 0.5-100 mg per day for an adult patient.

When the compound represented by the formula (I') is administered orally as a drug, it is administered in the form of tablets, granules, powder or capsules. When it is administered parenterally, it is administered in the form of injections or suspensions. In order to produce these pharmaceutical preparations, excipients, binding agents, disintegrating agents, lubricants, stabilizers and the like which are described in the explanation of the compound represented by the formula (I) can be added. If necessary, other drugs can be mixed.

[VII] Experimental Examples

The present invention is further described in detail with reference to the following Referential Examples and Examples, which are given for the purpose of merely illustrating the invention without limiting it.

1) Compounds Represented by the Formula (I)

Referential Example 1)-1

Vasorelaxing Effect on the Isolated Rat Aortae

(1) Method

The compounds of the present invention were tested for their physiological activities by measuring the tension of isolated rat aortae isometrically.

Thoracic aortae obtained from male Wistar rats (weighing 250-350 g) were cut into ring segments about 3 mm long. The ring preparation was placed in an organ bath filled with 10 ml of Krebs-Ringer solution that was maintained at 37° C. and gassed with 95% $O_2$-5% $CO_2$.

The preparation in the organ bath was allowed to equilibrate under resting tension of 1 g. After equilibration period, the solution in the organ bath was replaced with an isotonic solution containing 40 mM KCl to contract the preparation.

After the contraction induced by KCl had reached plateau, the concentration-response relationship for the test compound was determined by means of cumulative addition.

The relaxation response of the test compounds was expressed as the percent inhibition of the contraction induced by KCl, and the $IC_{50}$ value, which is a concentration required for inhibiting the contraction induced by KCl to an extent of 50%, was calculated by the Probit method from the concentration-response curve.

(2) Results

The $IC_{50}$ values of the test compounds and the control compounds are shown in the following table.

| Test Compound No. | $IC_{50}$ Value (M) |
|---|---|
| (1) | $4.6 \times 10^{-6}$ |
| (2) | $6.0 \times 10^{-5}$ |
| (3) | $4.9 \times 10^{-5}$ |
| (4) | $3.1 \times 10^{-5}$ |
| (5) | $6.5 \times 10^{-5}$ |
| (6) | $5.1 \times 10^{-5}$ |
| (7) | $2.3 \times 10^{-5}$ |
| (8) | $5.7 \times 10^{-5}$ |
| (9) | $7.2 \times 10^{-5}$ |
| (10) | $4.0 \times 10^{-5}$ |
| (11) | $1.2 \times 10^{-5}$ |
| (12) | $2.4 \times 10^{-5}$ |
| (13) | $5.1 \times 10^{-6}$ |
| (14) | $2.0 \times 10^{-5}$ |
| (15) | $9.5 \times 10^{-5}$ |
| (16) | $1.7 \times 10^{-5}$ |
| (17) | $6.6 \times 10^{-5}$ |
| (18) | $2.2 \times 10^{-5}$ |
| (19) | $3.7 \times 10^{-5}$ |
| (20) | $7.8 \times 10^{-5}$ |
| (21) | $7.0 \times 10^{-5}$ |
| (22) | $2.2 \times 10^{-5}$ |
| (23) | $9.8 \times 10^{-5}$ |
| (24) | $2.1 \times 10^{-5}$ |
| (25) | $2.4 \times 10^{-5}$ |
| (26) | $2.3 \times 10^{-5}$ |
| (27) | $4.0 \times 10^{-5}$ |
| (28) | $7.0 \times 10^{-5}$ |
| (29) | $3.8 \times 10^{-5}$ |
| (30) | $4.3 \times 10^{-5}$ |
| (31) | $1.6 \times 10^{-5}$ |
| (32) | $7.8 \times 10^{-5}$ |
| (33) | $9.5 \times 10^{-5}$ |
| (34) | $3.8 \times 10^{-5}$ |
| (35) | $1.8 \times 10^{-5}$ |
| (36) | $1.6 \times 10^{-5}$ |
| (37) | $2.8 \times 10^{-5}$ |
| (38) | $6.8 \times 10^{-5}$ |
| (39) | $4.8 \times 10^{-5}$ |

-continued

| | |
|---|---|
| (40) | $4.0 \times 10^{-5}$ |
| (41) | $1.2 \times 10^{-5}$ |
| (42) | $2.0 \times 10^{-5}$ |
| (43) | $5.2 \times 10^{-5}$ |
| (44) | $1.9 \times 10^{-5}$ |
| (45) | $4.9 \times 10^{-5}$ |
| (46) | $3.0 \times 10^{-5}$ |
| (47) | $4.0 \times 10^{-5}$ |
| (48) | $7.3 \times 10^{-5}$ |
| (49) | $6.2 \times 10^{-5}$ |
| (50) | $1.4 \times 10^{-5}$ |
| (51) | $1.3 \times 10^{-5}$ |
| (52) | $1.1 \times 10^{-5}$ |
| (53) | $7.7 \times 10^{-5}$ |
| Control Compounds | $IC_{50}$ Value (M) |
| 1. N-cyano-3-pyridine-carboxyimidamide | $4.0 \times 10^{-2}$ |
| 2. N-cyano-4-pyridine-carboxyimidamide | $1.8 \times 10^{-4}$ |

Referential Example 1)-2

Potassium Channel Activating Effect (1) Method

The compounds of the present invention (N-cyano-N'-(2-nitroxyethyl)-3-pyridinecarboximidamide (compound (13)), N-cyano-N'-benzyl-3-pyridinecarboximidamide (compound (17)), N-cyano-N'-(2-phenylethyl)-3-pyridinecarboximidamide (compound (27)) and N-cyano-N'-(2-nitroxyethyl)-4-pyridinecarboximidamide (compound (41)) were tested for the potassium channel activating effect by using the $^{86}$rubidium (referred to hereinafter as $^{86}$Rb) which is a radioisotope as a marker of potassium [See Journal of Physiology, 316, 33 (1981)].

Male Wistar rats (weighing 250–350 g) were dehematized to death, and thoracic aortae were rapidly isolated. The aorta was opened along the longitudinal axis to prepare a flat sheet. The preparation was loaded with $^{86}$Rb in the Krebs-Ringer solution which contained $^{86}$Rb in the concentration of 10 μCi/ml and was gassed with 95% $O_2$–5% $CO_2$ at 37° C. for 2 hours. The preparation was then transferred to a Krebs-Ringer solution not containing $^{86}$Rb, and washed to remove excess radioactivity for 18 minutes by refreshing the solution every 2 minutes. Finally the preparation was placed into a Krebs-Ringer solution containing each compound ($10^{-4}$ M) for 8 minutes.

The amount of $^{86}$Rb efflux from the preparation in each period was determined with a γ-counter.

The increment in efflux rate during the application of the compound was expressed as percent of the efflux before the application of the compound.

(2) Results

The increment in $^{86}$Rb efflux ratio (%) during the application of the test compounds are shown in the following table.

| Compound No. | Increment of Efflux (%) |
|---|---|
| (13) | 213.53 |
| (17) | 135.41 |
| (27) | 206.61 |
| (41) | 126.88 |

Referential Example 1)-3

Hypotensive effect on spontaneous hypertensive rats (intravenously)

(1) Method

The hypotensive effects of the compounds of the present invention [test compounds: N-cyano-N'-(2-nitroxyethyl)-2-pyridinecarboximidamide (compound (1)), N-cyano-N'-(2-nitroxyethyl)-3-pyridinecarboximidamide (compound (13)), N-cyano-N'-benzyl-3-pyridinecarboximidamide (compound (17)), N-cyano-N'-(2-phenylethyl)-3-pyridinecarboximidamide (compound (27)), pyridinecarboximidamide (compound (29)) and N-cyano-N'-(2-nitroxyethyl)-4-pyridinecarboximidamide (compound (41))] were observed in male spontaneous hypertensive rats (SHR).

Rats were anesthetized with urethane-α-chloralose (1 g/kg–25 mg/kg; intraperitoneally). Mean blood pressure was measured by a pressure transducer through a cannula inserted into the carotid artery. The compound was cumulatively administered every 30 minutes through the cannula inserted into the jagular vein. The change in blood pressure was expressed as percent of the blood pressure before the administration of the compound. And the $ED_{20}$ value, which was the dose required for descending blood pressure to an extent of 20%, was calculated from the dose-response curve.

(2) Results

The $ED_{20}$ values of the test compounds are shown in the following table.

| Compound No. | $ED_{20}$ (mg/kg, i.v.) |
|---|---|
| (1) | 0.037 |
| (13) | 0.010 |
| (17) | 0.250 |
| (27) | 0.074 |
| (29) | 0.013 |
| (41) | 0.130 |

Referential Example 1)-4

Hypotensive Effect on Spontaneous Hypertensive Rats (Orally)

(1) Method

The hypotensive effect by oral administration of the compound of the present invention [test compound: N-cyano-N'-(2-nitroxyethyl)-3-pyridinecarboximidamide (compound (13))] was observed in male spontaneous hypertensive rats (SHR).

Systolic pressure of the rats fasted for 24 hour was measured by using the tail cuff method before and 2 hours after administration of the compound. The compound was dissolved in a mixed solvent of polyethylene glycol 200:physiological saline=1:1. The control group was administered the solvent alone. The change in blood pressure was expressed as percent of the blood pressure before the administration of the compound in respective groups.

(2) Results

The decreasing rates (%) of the blood pressure by the test compound are shown in the following table.

| Dose (mg/kg, p.o.) | | Decreasing Rate of Blood Pressure (%) |
|---|---|---|
| Compound (13) | 0.3 | 6.76 ± 1.53 |
| | 0.5 | 9.12 ± 2.41 |
| | 1.0 | 27.31 ± 2.32 |
| | 3.0 | 49.99 ± 2.48 |
| Control Group | | −2.11 ± 3.21 |

(mean ± S.E.M.)

Referential Example 1)-5

Hypotensive Effect on Beagles (Intravenously)

(1) Method

The hypotensive effect of the compound of the present invention [test compound: N-cyano-N'-(2-nitroxyethyl)-3-pyridinecarboximidamide (compound (13))] was observed in beagles of either sex anesthetized with intravenous injection of sodium pentobarbital (35 mg/kg).

Mean blood pressure was measured by means of a pressure transducer through a cannula inserted into the femoral artery. The compound was administered into the femoral vein through the cannula. The change in blood pressure was expressed as percent changes from the pretreatment values.

(2) Results

The decreasing rates (%) of blood pressure by the test compound are illustrated in FIG. 1.

Referential Example 1)-6

Effect on Isolated Rat Heart

(1) Method

The effect of the compound of the present invention on heart of rats was examined by using the Langendorff's method [test compound: N-cyano-N'-(2-nitroxyethyl)-3-pyridinecarboximidamide (compound (13))]. Hearts were excised from male rats (weighing 250–350 g) and perfused at 80 $cmH_2O$ in a Langendorff fashion. Krebs-Hensaleit bicarbonate solution (pH 7.4, 37° C.) containing an 11 mM glucose which was oxygenated with 95% $O_2$–5% $CO_2$ gas mixture was used as a perfusate. The left ventricular pressure was recorded by inserting a latex baloon into the left ventricle, and heart rate was determined from the pulse of it. Coronary perfusate flow was also measured with an electromagnetic flowmeter. The experiments were carried out by perfusing a perfusate containing the compound (13) for 10 minutes after an initial equilibration period for 30 minutes. As the control compound, nicorandil which has an effect opening potassium channel and is similar to the test compound in structure was used. The changes in the coronary perfusate flow and the cardiac function (heart rate x left ventricular pressure) caused by these compounds were expressed as percent changes from the preperfusion values of the compound (13) or nicorandil.

(2) Results

The effects of these compounds on coronary perfusate flow and cardiac function are shown in the following table.

| | Concentration (mol/min) | The Number of Experiments | Coronary Perfusate Flow (% change) | Cardiac Function |
|---|---|---|---|---|
| Nicorandil | $1 \times 10^{-8}$ | 3 | 3.3 ± 5.6 | 3.7 ± 6.7 |
| Compound (13) | $1 \times 10^{-8}$ | 3 | 51.3 ± 3.2** | 13.3 ± 6.5 |

(mean ± S.D.)
**$p < 0.01$ as compared with nicorandil (Student's t-test)

Referential Example 1)-7

Hemodynamic Profile of the Compound of the Present Invention in Beagles (Intravenously)

(1) Method

Hemodynamic profile of the compound of the present invention was investigated in beagles anesthetized with pentobarbital (30 mg/kg, intravenously) [test compound: N-cyano-N'-(2-nitroxyethyl)-3-pyridinecarboximidamide (compound (13))]. The thorax was opened under artificial respiration. After administering heparin in an amount of 500 units/kg, a Moravitz's cannula was introduced into the coronary sinus via the right atrium. The coronary sinus outflow was returned to the right external jagular vein. The coronary sinus outflow was measured by an electromagnetic flowmeter (MFU-2100, manufactured by Nihon Kohden) connected to the Moravitz's cannula. A cannula was inserted into the aortic arch through the subclavian artery to measure aortic blood pressure. The aortic blood pressure was measured with a pressure transducer (Nihon Kohden, TP-200T). Heart rate was monitored with a heart rate counter with R waves of electrocardiogram. All parameters were recorded on a thermosensitive recorder (WT-685G, manufactured by Nihon Kohden).

The compound was administered through the cannula inserted into the right femoral vein. Nicorandil was used as a control. As for respective measurement items, peak changes were expressed as percent change from the pretreatment values of the compound (13) or nicorandil.

(2) Results

The results obtained by the compound (13) and nicorandil are shown in the following table.

| | Dose (μg/kg) | Mean Aortic Blood Pressure | Heart Rate | Coronary Blood Flow |
|---|---|---|---|---|
| Compound (13) | 3.0 | −15.3 ± 2.5 | 1.3 ± 1.4 | 16.4 ± 1.8 |
| | 10.0 | −38.5 ± 3.1 | −5.9 ± 2.8 | 96.0 ± 17.6 |
| | 30.0 | −50.7 ± 2.1 | −16.2 ± 3.3 | 134.1 ± 9.2 |
| Nicorandil | 100.0 | −21.3 ± 1.9 | 0.2 ± 2.1 | 20.3 ± 5.1 |
| | 300.0 | −43.1 ± 5.4 | −20.7 ± 1.9 | 84.9 ± 10.8 |

mean ± S.E.M. (N = 5)

Reference Example 1)-8

Hemodynamic Profile of the Compound of the Present Invention in Beagles (Intraduodenally)

(1) Method

The aortic blood pressure, the heart rate and the coronary blood flow of the beagles anesthetized with pentobarbital were determined in the same manner as in the aforementioned Example 1)-7, and the aortic blood flow was measured with an electromagnetic flowmeter (MFV-3100, manufactured by Nihon Kohden) by attaching a probe at the origin of the aorta [test compound: N-cyano-N'-(2-nitroxyethyl)-3-pyridinecarboximidamide (compound (13))]. A nelaton's tube was inserted into the duodenum via a small abdominal incision for administration of the compound (13) (100 μg/kg). Time course changes in respective measurement items were expressed as percent changes from the pretreatment values. Total peripheral resistance was calculated by dividing the mean aortic blood pressure with the sum of the coronary blood flow and the aortic blood flow.

(2) Results

Time course of the changes after intraduodenal administration of the compound (13) (100 μg/kg) are shown in the following table.

| | Time after dosage (min) | | | | | | | | |
|---|---|---|---|---|---|---|---|---|---|
| | 1 | 2 | 3 | 5 | 7.5 | 10 | 20 | 30 | 60 |
| Mean Aortic Blood Pressure (3) | −9.8 ± 1.0 | −14.3 ± 1.3 | −21.2 ± 1.2 | −35.0 ± 2.0 | −37.0 ± 2.9 | −42.0 ± 2.9 | −49.4 ± 3.1 | −49.0 ± 3.7 | −36.5 ± 7.3 |
| Heart Rate (3) | 0 | 1.6 ± 1.6 | 0 | −12.1 ± 5.1 | −17.5 ± 4.1 | −21.1 ± 4.4 | −26.1 ± 5.5 | −26.5 ± 4.6 | −10.0 ± 1.4 |
| Coronary Blood Flow (3) | 1.8 ± 1.8 | 14.4 ± 2.1 | 38.4 ± 9.1 | 121.5 ± 22.0 | 142.3 ± 6.5 | 112.8 ± 10.6 | 64.2 ± 15.4 | 60.1 ± 15.1 | 28.0 ± 11.6 |
| Aortic Blood Flow (2) | 10.0 | 12.2 | 15.1 | 27.0 | 25.5 | 15.0 | 10.7 | 8.3 | 0.5 |
| Total Peripheral Resistance (2) | −17.8 | −24.1 | −33.7 | −49.5 | −50.3 | −51.1 | −55.3 | −55.8 | −44.3 |

mean ± SEM; Numbers in parentheses denote sample numbers.

Referential Example 1)-9

Effect on 3,4-Diaminopyridine-Induced Rhythmic Contractions in Dog Coronary Artery (1) Method It is known that the attack of pseudoangina pectoris often appears and the spasms of the coronary artery occurs during the attack. It is considered that when 3,4-diaminopyridine (referred to hereinafter as 3,4-DAP) is administered to act on coronary artery in vitro, rhythmic contraction occurs, and this period of the contraction well accords with that of the attack of pseudoangina pectoris [see MYAKKAN-GAKU (Angiology), 24, 133 (1984)]. The effect of the compound of the present invention on the rhythmic contraction caused by 3,4-DAP was tested in coronary arteries isolated from beagles [test compound: N-cyano-N'-(2-nitroxyethyl)-3-pyridinecarboximidamide (compound (13))].

Beagles were anesthetized with pentobarbital and the heart was excised. The coronary arteries were dissected from the myocardium and cut into 3 mm long rings in the oxygenated Krebs-Ringer solution. The ring was suspended into an organ bath filled with the Krebs-Ringer solution that was maintained at 37° C. and gassed with 95% $O_2$-5% $CO_2$. Isometric contraction was recorded on a pen-writing recorder (FBR-252A, manufactured by TOA Denpa) through a FD pick-up (TB-611T, manufactured by Nihon Kohden) and a carrier amplifier (AP-621G, manufactured by Nihon Kohden). After equilibration period under 1 g resting tension, 3,4-DAP ($10^{-2}$ M) was added to the organ bath. When the frequency and the amplitude of the oscillation became constant, the compound was added cumulatively to the bath.

(2) Results

Inhibitory effect of the compound (13) on the rhythmic contraction induced by 3,4-DAP in the coronary arteries of beagles is illustrated in FIG. 2.

Referential Example 1)-10

Effect of the Compound of the Present Invention on the Experimental Model of Angina Pectoris Induced by Vasopressin in Rats (1) Method It is known that when vasopressin is administered intravenously to a rat, myocardial ischemia accompanied with the depression of ST segment in the electrocardiogram can be induced. This phenomenon is very similar to the attack of pseudoangina pectoris which is observed clinically [see Japanese Journal of Pharmacology, 20, 313 (1970); OYO-YAKURI (Applied Pharmacology), 19, 311 (1980)]. The effect of the compound of the present invention on this model on the pseudoangina pectoris was examined [Test Compound: N-cyano-N'-(2-nitroxyethyl)-3-pyridinecarboximidamide (compound (13))].

Male Donryu rats, weighing 200-500 g, were anesthetized with urethane-α-chloralose (1g/kg-25 mg/kg; intraperitoneally). Vasopressin at the dose of 1.0 IU/kg was administered 2 minutes after the administration of the test compound (100 μg/kg). Vasopressin and test compound were intravenously administered into the femoral vein. The changes in the ST segment in Lead II electrocardiogram were observed after the administration of vasopressin. Nicorandil was used as a control.

(2) Results

The effect of the compound of the present invention on a vasopressin-induced angina pectoris model is shown in FIG. 3.

Referential Example 1)-11

Effect of the Compound of the present invention on the myocardiac injury inducted by re-perfusion after ischemia (1) Method The cardiac muscle protecting effect of the compound of the present invention was tested by using the isolated heat of rats [test compound: N-cyano-N'-(2-nitroxyethyl)- 3-pyridinecarboximidamide (compound (13))]. The Langendorff's method was used in the same manner as in the aforementioned Referential Example 1)-6. The isolated heart was perfused with a perfusate for 30 minutes and then with a perfusate containing the test compound for 10 minutes, and perfusion was stopped so that the heart was in the so-called "ischemic state". Pacing was performed during the ischemia. After 25 minutes, perfusion was stated again with the original perfusate which did not contain the test compound. Parameters of cardiac function after the onset of re-perfusion was monitored for 30 minutes, and the heart was quickly freezed. The amount of ATP in the heart muscle was extracted with perchloric acid and determined by HPLC. Nicorandil was used as a control.

The recovery rate of the cardiac function (heart rate×left ventricular pressure) after onset of reperfusion was calculated based on the cardiac function prior to the perfusion of the compound (13) and nicorandil as 100%. The amount of ATP in the heart muscle was also determined.

(2) Results

Recovery rates of the cardiac function and amounts of ATP in the heart muscle are shown in the following table.

| | Concentration (mole/min) | Recovery rate of cardiac function (%) | Amount of ATP in the heart muscle (μmole/g of dry weight) |
|---|---|---|---|
| Physiological saline | | 0.5 ± 0.5 (11) | 5.76 ± 0.83 (5) |
| Nicorandil | $1 \times 10^{-6}$ | 12.7 ± 8.2 (4) | 5.93 ± 0.49 (4) |
| Compound (13) | $1 \times 10^{-7}$ | 67.5 ± 6.0 (3)** | 11.12 ± 1.12 (6) |

(mean ± SD);
Numbers within parentheses denote specimen numbers.
**p < 0.01 (comparison with the physiological saline group) (Student's t-test)

Referential Example 1)-12

Effect of the Compound of the Present Invention on the Isolated Beagle Basilar Artery (1) Method A beagle was anesthetized with pentobarbital and dehematized from common carotid artery to death. The basilar artery was isolated rapidly. The artery was removed fat and connective tissue carefully and was cut into ring segments about 3.5 mm long in the Krebs-Ringer solution under oxygen. The ring preparation was suspended into an organ bath filled with the Krebs-Ringer solution which was maintained at 37° C. and gassed with 95% $O_2$–5% $CO_2$. The preparation in the organ bath was allowed to equilibrate under resting tension of 0.5 g. After equilibration period, U-46619 (thromboxane $A_2$ derivative, $10^{-7}$ M) was added to the organ bath in order to contract the preparation. After the contraction induced by U-46619 had reached plateau, the compound of the present invention was cumulatively added to the organ bath to relax the preparation [test compound: N-cyano-N'-(2-nitroxyethyl)-3-pyridinecarboximidamide (compound (13))].

The relaxation response was expressed as the percent inhibition of the contraction induced by U-46619.

(2) Results

The concentration-response curve for the relaxing action of the compound (13) is illustrated in FIG. 4.

Referential Example 1)-13

Effect of the Compound of the Present Invention on Hypoxia (1) Method

The effect of the compound of the present invention [test compound: N-cyano-N'-(2-nitroxyethyl)-3-pyridinecarboximidamide (compound (13))] on hypoxia was examined in male ddY mice (4 week old). Mice were exposed to a gas mixture of 96% $N_2$–4% Oz that was streamed in a flow rate of 5 l/min.

The time from the onset of the gas stream till the stop of respiration [survival time (sec)] was measured.

The test compound was orally administered in the dosage form of a 2% suspension in gum arabic 30 minutes before the onset of the gas streaming. The control group was administered a gum arabic suspension only.

(2) Results

Survival times of the control and the compound administered groups are shown in the following table.

| | Dose (mg/kg) | Number of Mice | Survival Time (sec) mean ± S.E.M. |
|---|---|---|---|
| Control group | | 15 | 129.47 ± 8.51 |
| Compound (13) | 0.3 | 15 | 130.27 ± 9.32 |
| | 1.0 | 14 | 201.00 ± 13.40*** |
| | 3.0 | 13 | 523.15 ± 48.57*** |

***p < 0.001 (Student's t-test)

Referential Example 1)-14

Inhibitory Effect of the Compound of the Present Invention on the Platelet Aggregation (1) Method Using platelets of a beagle, the inhibitory effect of the compound of the present invention on the platelet aggregation was examined [test compound: N-cyano-N'-(2-nitroxyethyl)-3-pyridinecarboximidamide (compound (13))]. Blood was collected from the cephalic vein of a beagle (blood: 3.8% citric acid =9:1) and centrifuged at 1050 rpm for 10 minutes. The supernatant was collected as platelet-rich plasma (PRP). Platelet poor plasma (PPP) was obtained by further centrifugation of the residue at 3000 rpm for 15 minutes. Platelets were adjusted to $3 \times 10^8$ platelets/ml by diluting PRP with PPP.

Adenosin diphosphate (ADP) was used as an aggregating agent. After preincubation stirred with or without the compound (13) for 2 minutes at 37° C, PRP was mixed with ADP. Platelet aggregation was measured photometrically in volume of 750 μl of PRP by means of an aggregometer (CAF-100, manufactured by Japan Spectroscopic).

(2) Results

The inhibiting effect of the compound (13) on platelet aggregation was illustrated in FIG. 5. Vertical vibration state in this figure are diagrammatically illustrated.

Referential Example 1)-15

Relaxing Effect of the Compound of the Present Invention on the Isolated Guinea Pig Trachea (1) Method The relaxing effect of the compound of the present invention on the smooth muscle of trachea obtained from quinea pig was examined [test compound: N-cyano-N'-(2-nitroxyethyl)-3-pyridinecarboximidamide (compound (13))]. A male Hartley guinea pig (weighing 250 g) was dehematized to death. The trachea was isolated and cut into a spiral strip in the Krebs-Ringer solution. The preparation was placed in an organ bath filled with the Krebs-Ringer solution which was maintained at 37° C. and gassed with 95% $O_2$-5% $CO_2$. The preparation in the organ bath was allowed to equilibrate under resting tension of 0.5 g. After equilibration period, the solution in the organ bath was replaced with an isotonic solution containing 40 mM KCl to contract the trachea preparation.

After the contraction induced by KCl had reached plateau, the compound (13) was cumulatively added to the organ bath to relax the preparation.

The relaxation response was expressed as the percent inhibition of the contraction induced by KCl.

(2) Results

The concentration-response curve for the relaxing effect of the compound (13) is illustrated in FIG. 6.

Referential Example 1)-16

Acute Toxicity (1) Method

Using male ddY mice (4 week old), acute toxicity on the oral administration of the compound of the present invention was examined [test compound: N-cyano-N'-(2-nitroxyethyl)-3-pyridinecarboximidamide (compound (13))]. As a result, $LD_{50}$ was about 400 mg/kg.

Example 1)-1

Preparation of N-cyano-N'-(2-nitroxyethyl)-2-pyridinecarboximidamide (Method i)

a) 2-cyanopyridine (10.0 g, 96.1 mmol) was dissolved in methanol (50 ml). Sodium methoxide (0.26 g, 4.8 mmol) was added to the solution, and reaction was conducted for 6 hours at room temperature. After the reaction was completed, acetic acid (0.32 g, 5.3 mmol) was added to neutralize the reaction solution, and the solution was concentrated under reduced pressure. Diethyl ether (50 ml) was added to the concentrated residue, and diethyl ether insoluble products were removed by filtration. The filtrate was concentrated under reduced pressure to give the crude product of methyl 2-pyridinecarboximidate as a pale yellow oil in a yield of 7.5 g.

Next, cyanamide (4.64 g, 110 mmol) and a phosphate buffer (pH 5.4) (70 ml) of $Na_2HPO_4$ (7.81 g, 55 mmol) and $NaH_2PO_4.2H_2O$ (34.3 g, 220 mmol) were added to the oil, and the mixture was stirred vigorously at room temperature for 4 hours. After the reaction was completed, extraction was carried out with dichloromethane (100 ml×3), and the dichloromethane layer was dried over anhydrous sodium sulfate and then concentrated under reduced pressure. The concentrated residue thus obtained was subjected to chromatography on a silica gel column (WAKO GEL C-200, 40 g) by eluting with hexane : diethyl ether (1:2). The product obtained was further crystallized from dichloromethane-diethyl ether to give methyl N-cyano-2-pyridinecarboximidate (8.81 g, 54.7 mmol, yield: 57%) as colorless needles.

Physico-chemical properties of methyl N-cyano-2-pyridinecarboximidate

MP: 81.0°-81.5° C.;

IR spectrum: ($cm^{-1}$, KBr) 2220, 1640, 1570, 1340;

NMR spectrum: (100 MHz, $CDCl_3$—$CD_3OD$) δ (ppm) 8.83 (1H, ddd, J=2.4, 3.4, 9.4Hz), , 7.98 (1H, dd, J=2.4, 7.3Hz), 7.94 (1H, d, J=3.4Hz), : 7.63 (1H, dd, J=7.3, 9.4Hz), 4.16 (3H, s).

b) Methyl N-cyano-2-pyridinecarboximidate (0.50 g, 3.1 mmol) was dissolved in methanol (5 ml), 2-nitroxyethylamine nitrate (0.57 g, 3.4 mmol) was added, and sodium methoxide (0.18 g, 3.4 mmol) was further added gradually. The mixture was stirred at room temperature for 10 minutes. After the reaction was completed, the reaction solution was concentrated under reduced pressure, and the residue thus obtained was extracted with dichloromethane (50 ml×3). The dichloromethane layer was dried over anhydrous sodium sulfate and concentrated under reduced pressure. The concentrated residue was crystallized from dichloromethane-diethyl ether to give the title compound (0.44 g, 0.20 mmol, yield: 63%) as colorless needles.

Physico-chemical properties of N-cyano-N'-(2-nitroxyethyl)-2-pyridinecarboximidamide

MP: 53.5°-54.0° C.;

IR spectrum: ($cm^{-1}$, KBr) 3280, 2180, 1640, 1630, 1600, 1580, 1560, 1290;

NMR spectrum: (100 MHz, $CD_3OD$) δ (ppm) 8.73 (1H, br d, J=3.4Hz), 8.3-7.9 (2H, m), 7.64 (1H, m), 4.77 (2H, t, J=5.5Hz), 3.92 (2H, t, J=5.5Hz);

| Elementary Analysis: | C | H | N |
|---|---|---|---|
| Calculated: | 45.96 | 3.86 | 29.78 |
| Found: | 45.68 | 3.76 | 30.12 (%) |
| | ($C_9H_9N_5O_3$) | | |

Example 1)-2

Preparation of N-cyano-N'-(2,2-dimethylpropyl)-2-pyridinecarboximidamide (method i)

Methyl N-cyano-2-pyridinecarboximidate (0.50 g, 3.1 mmol) was dissolved in methanol (10 ml), 2,2-dimethylpropylamine (0.30 g, 3.4 mmol) was added, and the resulting mixture was stirred at room temperature for 30 minutes. After the reaction was completed, the reaction solution was concentrated under reduced pressure, and the residue thus obtained was crystallized from dichloromethane-diethyl ether to give the title compound (0.63 g, 2.9 mmol, yield: 94%) as colorless needles.

Physico-chemical properties of N-cyano-N'-(2,2-dimethylpropyl)-2-pyridinecarboximidamide

MP: 109°-109.8° C.;

IR spectrum: ($cm^{-1}$, KBr) 3260, 2970, 2190, 1600, 1580, 1560;

NMR spectrum: (100 MHz, $CDCl_3$) δ (ppm) 8.7-8.5 (3H, m), 8.00-7.80 (1H, m), 7.6-7.4 (1H, m), 3.58 (2H, d, J=6.9Hz), 1.05 (9H, s);

| Elementary Analysis: | C | H | N |
|---|---|---|---|
| Calculated: | 66.64 | 7.46 | 25.90 |
| Found: | 66.41 | 7.58 | 25.72 (%) |
| | ($C_{12}H_{16}N_4$) | | |

Example 1)-3

Preparation of N-cyano-N'-(1,2,2-trimethylpropyl)-2-pyridinecarboximidamide (method i)

Methyl N-cyano-2-pyridinecarboximidate (0.50 g, 3.1 mmol) was dissolved in methanol (10 ml), 1,2,2-trimethylpropylamine (0.34 g, 3.4 mmol) was added, and the resulting mixture was stirred at room temperature for 30 minutes. After the reaction was completed, the reaction solution was concentrated under reduced pressure, and the residue thus obtained was crystallized from dichloromethane-diethyl ether to give the title compound (0.67 g, 2.9 mmol, yield: 92%) as colorless needles.

Physico-chemical properties of N-cyano-N'-(1,2,2-trimethylpropyl)-2-pyridinecarboximidamide

MP: 96.5°-97.0° C.;

IR spectrum: ($cm^{-1}$, KBr) 3230, 3100, 2960, 2180, 1590, 1580, 1560;

NMR spectrum: (100 MHz, $CD_3OD$) δ (ppm) 8.60 (2H, m), 7.92 (1H, m), 7.50 (1H, m), 4.48 (1H, q, J=7.2Hz), 1.28 (3H, d, J=7.2Hz), 1.03 (9H, s);

| Elementary Analysis: | C | H | N |
|---|---|---|---|
| Calculated: | 67.80 | 7.88 | 24.33 |
| Found: | 67.51 | 7.97 | 24.25 (%) |
| | ($C_{13}H_{18}N_4$) | | |

Example 1)-4

Preparation of N-cyano-N'-phenyl-2 -pyridinecarboximidamide (method i)

Methyl N-cyano-2-pyridinecarboximidate (0.50 g, 3.1 mmol) was dissolved in methanol (10 ml), aniline (0.32 g, 3.4 mmol) was added, and the resulting mixture was stirred at room temperature for 40 minutes. After the reaction was completed, the reaction solution was concentrated under reduced pressure, and the residue thus obtained was crystallized from dichloromethane-diethyl ether to give the title compound (0.63 g, 2.8 mmol, yield: 91%) as colorless needles.

Physico-chemical properties of N-cyano-N'-phenyl-2-pyridinecarboximidamide

MP: 103.0°-104.0° C.;

IR spectrum: ($cm^{-1}$, KBr) 2180, 1620, 1610, 1580, 1560;

NMR spectrum: (100 MHz, $CD_3OD$) δ (ppm) 8.80 (1H, br s), 8.4-8.0 (2H, m), 7.9-7.2 (6H, m);

| Elementary Analysis: | C | H | N |
|---|---|---|---|
| Calculated: | 70.26 | 4.54 | 25.21 |
| Found: | 70.09 | 4.57 | 25.14 (%) |
| | ($C_{13}H_{10}N_4$) | | |

Example 1)-5

Preparation of N-cyano-N'-(4-methoxyphenyl)-2-pyridinecarboximidamide (method i)

Methyl N-cyano-2-pyridinecarboximidate (0.50 g, 3.1 mmol) was dissolved in methanol (10 ml), 4-methoxyaniline (0.36 g, 3.4 mmol) was added, and the resulting mixture was stirred at room temperature for 30 minutes. After the reaction was completed, the reaction solution was concentrated under reduced pressure, and the residue thus obtained was crystallized from dichloromethane-diethyl ether to give the title compound (0.74 g, 2.9 mmol, yield: 94%) as colorless needles.

Physico-chemical properties of N-cyano-N'-(4-methoxyphenyl)-2-pyridinecarboximidamide

MP: 116.5°-117.2° C.;

IR spectrum: ($cm^{-1}$, KBr)

NMR spectrum: (100 MHz, $CD_3OD$) δ (ppm) 8.77 (1H, br d, J=5.8Hz), 8.25 (1H, d, J=7.2Hz), 8.06 (1H, t, J=7.2Hz), 7.8-6.9 (3H, m), 6.98 (2H, br d, J=10.3Hz), 3.83 (3H, s);

| Elementary Analysis: | C | H | N |
|---|---|---|---|
| Calculated: | 66.66 | 4.79 | 22.21 |
| Found: | 66.41 | 4.83 | 22.12 (%) |
| | ($C_{14}H_{12}N_4O$) | | |

Example 1)-6

Preparation of N-cyano-N'-(4-methylbenzyl)-2-pyridinecarboximidamide (method i)

Methyl N-cyano-2-pyridinecarboximidate (0.30 g, 1.9 mmol) was dissolved in methanol (10 ml), p-methylbenzylamine (0.25 g, 2.1 mmol) was added, and the resulting mixture was stirred at room temperature for 2 hours. After the reaction was completed, the reaction solution was concentrated under reduced pressure, and the residue thus obtained was crystallized from diethyl ether to give the title compound (0.41 g, 1.6 mmol, yield: 91%) as colorless crystals.

Physico-chemical properties of N-cyano-N'-(4-methylbenzyl)-2-pyridinecarboximidamide

MP: 104.2°-104.8° C.;

IR spectrum: ($cm^{-1}$, KBr) 2180, 1600, 1570;

NMR spectrum: (100 MHz, $CDCl_3$) δ (ppm) 8.8-8.5 (2H), 7.91 (1H, dt, J=2.7, 7.5Hz), 7.49 (1H, dd, J=4.8, 7.5Hz), 7.35-7.15 (4H), 4.84 (2H, d, J=7.3Hz), 2.37 (3H, s);

| Elementary Analysis: | C | H | N |
|---|---|---|---|
| Calculated: | 71.98 | 5.64 | 22.38 |
| Found: | 71.87 | 5.59 | 22.11 (%) |
| | ($C_{15}H_{14}N_4$) | | |

Example 1)-7

Preparation of N-cyano-N'-(4-chlorobenzyl)-2-pyridinecarboximidamide (method i)

Methyl N-cyano-2-pyridinecarboximidate (0.50 g, 3.1 mmol) was dissolved in methanol (10 ml), 4-chlorobenzylamine (0.48 g, 3.4 mmol) was added, and the resulting mixture was stirred at room temperature for 5 hours.

After the reaction was completed, the reaction solution was concentrated under reduced pressure, and the residue thus obtained was crystallized from diethyl ether to give the title compound (0.13 g, 0.5 mmol, yield: 16%) as colorless crystals.

Physico-chemical properties of N-cyano-N'-(4-chlorobenzyl)-2-pyridinecarboximidamide

MP: 93.5°-94.0° C.;

IR spectrum: ($cm^{-1}$, KBr) 2180, 1610, 1560;

NMR spectrum: (100 MHz, $CDCl_3$) δ (ppm) 8.75-8.55 (2H), 7.92 (1H, dt, J=2.4, 7.5Hz), 7.50 (1H, dd, J=5.1, 7.5Hz), 7.36 (4H, s), 4.85 (2H, d, J=6.8Hz);

| Elementary Analysis: | C | H | N |
|---|---|---|---|
| Calculated: | 62.11 | 4.10 | 20.70 |
| Found: | 62.08 | 4.00 | 20.43 (%) |
| | ($C_{14}H_{11}N_4Cl$) | | |

Example 1)-8

Preparation of N-cyano-N'-[4-(trifluoromethyl)benzyl]-2-pyridinecarboximidamide (method i)

Methyl N-cyano-2 pyridinecarboximidate (0.30 g, 1.9 mmol) was dissolved in methanol (10 ml), 4-(trifluoromethyl)benzylamine (0.36 g, 2.1 mmol) was added, and the resulting mixture was stirred at room temperature for 30 minutes. After the reaction was completed, the reaction solution was concentrated under reduced pressure, and the residue thus obtained was crystallized from diethyl ether to give the title compound (0.47 g, 1.5 mmol, yield: 84%) as colorless crystals.

Physico-chemical properties of N cyano-N'-[4-(trifluoromethyl)benzyl]-2-pyridinecarboximidamide

MP: 127.0°-127.2° C.;

IR spectrum: ($cm^{-1}$, KBr) 2180, 1570, 1330;

NMR spectrum: (100 MHz, $CDCl_3$) δ (ppm) 8.80-8.55 (2H), 7.95 (1H, dt, J=2.7, 7.2Hz), 7.70-7.40 (5H), 4.92 (2H, d, J=6.1Hz);

| Elementary Analysis: | C | H | N |
|---|---|---|---|
| Calculated: | 59.21 | 3.64 | 18.41 |
| Found: | 59.15 | .3.63 | 18.25 (%) |
| | ($C_{15}H_{11}N_4F_3$) | | |

Example 1)-9

Preparation of N-cyano-N'-[2-(4-methylphenyl)ethyl]-2-pyridinecarboximidamide (method i)

Methyl N-cyano-2-pyridinecarboximidate (0.50 g, 3.1 mmol) was dissolved in methanol (10 ml), 2-(p-tolyl)ethylamine (0.47 g, 3.5 mmol) was added, and the resulting mixture was stirred at room temperature for 1 hour. After the reaction was completed, the reaction solution was concentrated under reduced pressure, and the residue thus obtained was crystallized from methanol-diethyl ether to give the title compound (0.76 g, 2.9 mmol, yield: 93%) as colorless crystals.

Physico-chemical properties of N cyano-N'-[2-(4-methylphenyl)ethyl]-2-pyridinecarboximidamide

MP: 91.0°-91.5° C.;

IR spectrum: ($cm^{-1}$, KBr) 2180, 1600, 1580, 1560;

NMR spectrum: (500 MHz, $CDCl_3$) δ (ppm) 8.62-8.55 (2H), 8.41 (1H, br s), 7.89 (1H, dt, J=1.8, 7.8Hz), 7.48 (1H, dd, J=5.2, 7.8Hz), 7.15 (4H, dd, J=7.6, 14.0Hz), 3.97 (2H, br s), 2.99 (2H, t, J=7.6Hz);

| Elementary Analysis: | C | H | N |
|---|---|---|---|
| Calculated: | 72.70 | 6.10 | 21.20 |
| Found: | 72.44 | 5.98 | 21.01 (%) |
| | ($C_{16}H_{16}N_4$) | | |

Example 1)-10

Preparation of N-cyano-N'-[2-(4-chlorophenyl)ethyl]-2-pyridinecarboximidamide (method i)

Methyl N-cyano-2-pyridinecarboximidate (0.50 g, 3.1 mmol) was dissolved in methanol (10 ml), 4-chlorophenethylamine (0.53 g, 3.4 mmol) was added, and the resulting mixture was stirred at room temperature for 30 minutes. After the reaction was completed, the reaction solution was concentrated under reduced pressure, and the residue thus obtained was crystallized from dichloromethane-diethyl ether to give the title compound (0.43 g, 1.5 mmol, yield: 49%) as colorless needles.

Physico-chemical properties of N-cyano-N'-[2-(4-chlorophenyl)ethyl]-2-pyridinecarboximidamide

MP: 112.7°-113.0° C.;

IR spectrum: ($cm^{-1}$, KBr) 3280, 2170, 1620, 1550, 1440;

NMR spectrum: (100 MHz, $CDCl_3$) δ (ppm) 8.7-8.3 (3H), 7.90 (1H, m), 7.84 (1H, m), 7.3-7.1 (4H), 3.95 (2H, q, J=6.8Hz), 3.00 (2H, t, J=6.8Hz);

| Elementary Analysis: | C | H | N |
|---|---|---|---|
| Calculated: | 63.27 | 4.60 | 19.68 |
| Found: | 63.17 | 4.71 | 19.70 (%) |
| | ($C_{15}H_{13}N_4Cl$) | | |

Example 1)-11

Preparation of N-cyano-N'-(2-hydroxy-1-methyl-2-phenylethyl)-2-pyridinecarboximidamide (method i)

Methyl N-cyano-2-pyridinecarboximidate (0.24 g, 1.5 mmol) was dissolved in methanol (5 ml), DL-phenylpropanolamine hydrochloride (0.31 g. 1.7 mmol, supplied by Tokyo Chemical Industry Co., Ltd.) and triethylamine (0.17 g, 1.7 mmol) were added, and the resulting mixture was stirred at room temperature for 5 solution was concentrated under reduced pressure, and the residue thus obtained was extracted with ethyl acetate (30 ml×3). The ethyl acetate layer was washed with water (100 ml), dried over anhydrous sodium sulfate and concentrated under reduced pressure. The concentrated residue thus obtained was crystallized from diethyl ether to give the title compound (0.23 g, 0.8 mmol, yield: 54%) as colorless crystals.

Physico-chemical properties of N-cyano-N'-(2-hydroxy-1-methyl-2-phenylethyl)-2-pyridinecarboximidamide

MP: 135.2°-135.5° C.;

IR spectrum: ($cm^{-1}$, KBr) 2180, 1580, 1560;

NMR spectrum: (500 MHz, $CDCl_3$—$CD_3OD$) δ (ppm) 8.68 (1H, d, J=4.8Hz), 8.42 (1H, d, J=8.0Hz), 7.97 (1H, dt, J=2.0, 8.0Hz), 8.57 (1H, dd, J=5.6, 8.0Hz), 7.46 (2H, d, J=7.8Hz), 7.38 (2H, t, J=7.8Hz), 7.29 (1H, t, J=7.8Hz), 5.05 (1H, d, J=3.6Hz), 4.70 (1H, br s), 1.17 (3H, d, J=7.6Hz);

| Elementary Analysis: | C | H | N |
|---|---|---|---|
| Calculated: | 68.55 | 5.75 | 19.99 |
| Found: | 68.56 | 5.66 | 19.72 (%) |
| | ($C_{16}H_{16}N_4O$) | | |

Example 1)-12

Preparation of N-cyano-N'-(2-thienylmethyl)-2-pyridinecarboximidamide (method i)

Methyl N-cyano-2-pyridinecarboximidate (0.50 g, 3.1 mmol) was dissolved in methanol (10 ml), 2-thiophenemethylamine (0.38 g, 3.4 mmol) was added, and the resulting mixture was stirred at room temperature for 40 minutes. After the reaction was completed, the reaction solution was concentrated under reduced pressure, and the residue thus obtained was crystallized from dichloromethane-diethyl ether to give the title compound (0.40 g, 1.7 mmol, yield: 54%) as colorless needles.

Physico-chemical properties of N-cyano-N'-(2-thienylmethyl)-2-pyridinecarboximidamide

MP: 87.0°-88.0° C.;

IR spectrum: ($cm^{-1}$, KBr) 3220, 2160, 1600, 1580, 1560;

NMR spectrum: (500 MHz, CDC13) δ (ppm) 8.72 (1H, br s), 8.60 (1H, d, J=4.0Hz), 8.51 (1H, br s), 7.93 (1H, t, J=8.6Hz), 7.52 (1H, dd, J=5.1, 8.6Hz), 7.31 (1H, d, J=4.9Hz), 7.14 (1H, d, J=3.4Hz), 7.02 (1H, dd, J=3.7, 5.4Hz), 5.05 (2H, s);

| Elementary Analysis: | C | H | N |
|---|---|---|---|
| Calculated: | 59.49 | 4.16 | 23.12 |
| Found: | 59.76 | 4.14 | 23.21 (%) |
| | ($C_{12}H_{10}N_4S$) | | |

Example 1)-13

Preparation of N-cyano-N'-(2-nitroxyethyl)-3-pyridinecarboximidamide (method i)

a) 3-cyanopyridine (10.0 g, 96.1 mmol) was dissolved in isopropanol (50 ml). Sodium hydride (0.23 g, 9.6 mmol) from which oily matters had been removed by washing with ether was added to the solution, and the mixture was stirred at room temperature for 3 hours. After the reaction was completed, acetic acid (0.64 g, 10.7 mmol) was added to neutralize the reaction solution, and the solution was concentrated under reduced pressure. After concentrating the solution, diethyl ether (80 ml) was added to the concentrated residue, and insoluble products were removed by filtration. The filtrate was concentrated under reduced pressure, and hexane (80 ml) was added to the concentrated residue, and depositing unreacted 3-cyanopyridine was removed by filtration. The hexane solution was then concentrated under reduced pressure to give the crude product of isopropyl 3-pyridinecarboximidate as a pale yellow oil in a yield of 5.68 g.

Next, cyanamide (2.91 g, 69.2 mmol) and a phosphate buffer (pH 5.4, 30 ml) of $Na_2HPO_4$ (4.91 g, 34.6 mmol) and $NaH_2PO_4.2H_2O$ (21.59 g, 138.4 mmol) were added to the oil, and the mixture was stirred at room temperature for 6 hours. After the reaction was completed, the reaction solution was extracted with dichloromethane (100 ml×3), and the dichloromethane layer was dried over anhydrous sodium sulfate and then concentrated under reduced pressure. The concentrated residue thus obtained was subjected to chromatography on a silica gel column (WAKO GEL C-200, 250 g) by eluting with hexane : diethyl ether (1:2). The eluted fractions were concentrated to give isopropyl N-cyano-3-pyridinecarboximidate (4.84 g, 25.6 mmol, yield: 26%) as pale yellow oil.

Physico-chemical properties of isopropyl N-cyano-3-pyridinecarboximidate

IR spectrum: ($cm^{-1}$, neat) 3240, 2250, 2180, 1610, 1380, 1310, 1100;

NMR spectrum: (100 MHz, $CDCl_3$) δ (ppm) 9.15 (1H, d, J=2.6Hz), 8.83 (1H, dd, J=1.7, 4.9Hz), 8.48 (1H, ddd, J=1.7, 2.6, 8.1Hz), 7.50 (1H, dd, J=4.9, 8.1Hz), 5.42 (1H, m, J=7.2Hz), 1.48 (6H, d, J=7.2Hz).

b) Isopropyl N-cyano-3-pyridinecarboximidate (0.50 g, 2.6 mmol) was dissolved in methanol (10 ml), and 2-nitroxyethylamine nitrate (0.49 g, 2.9 mmol) and sodium methoxide (0.16 g, 2.9 mmol) were added. The mixture was stirred at room temperature for 10 minutes. After the reaction was completed, the reaction solution was concentrated under reduced pressure, and the residue was extracted with dichloromethane (50 ml×3). The dichloromethane layer was dried over anhydrous sodium sulfate and concentrated under reduced pressure. The concentrated residue was crystallized from dichloromethane-diethyl ether to give the title compound (0.48 g, 2.1 mmol, yield: 79%) as colorless needles.

Physico-chemical properties of N-cyano-N'-(2-nitroxyethyl)-3-pyridinecarboximidamide

MP: 99.5°-100.2° C.;

IR spectrum: ($cm^{-1}$, KBr) 2180, 1640, 1590, 1280;

NMR spectrum: (100 MHz, $CDCl_3$) δ (ppm) 8.73 (1H, d, J=4.9Hz), 8.71 (1H, s), 8.16 (1H, d, J=7.9Hz), 7.51 (1H, dd, J=4.9, 7.9Hz), 4.72 (2H, t, J=4.9Hz), 3.84 (2H, t, J=4.9Hz);

| Elementary Analysis: | C | H | N |
|---|---|---|---|
| Calculated: | 45.96 | 3.86 | 29.78 |
| Found: | 45.77 | 3.78 | 30.01 (%) |
| | ($C_9H_9N_5O_3$) | | |

Example 1)-14

Preparation of N-cyano-N'-(3-nitroxypropyl)-3-pyridinecarboximidamide (method i)

Isopropyl N-cyano-3-pyridinecarboximidate (0.50 g, 2.6 mmol) was dissolved in methanol (10 ml), and 3-nitroxypropylamine nitrate (0.53 g, 2.9 mmol) and sodium methoxide (0.16 g, 2.9 mmol) were added. The mixture was stirred at room temperature for 18 hours. After the reaction was completed, the reaction solution was concentrated under reduced pressure, and the residue was extracted with chloroform (30 ml×3). The chloroform layer was washed with water (100 ml), dried over anhydrous sodium sulfate and concentrated under reduced pressure. The concentrated residue thus obtained was subjected to chromatography on a silica gel column (WAKO GEL C-200, 30 g) eluting with chloroform-methanol (60:1). Eluted fractions were concentrated under reduced pressure and crystallized from methanol-diethyl ether to give the title compound (0.26 g, 1.0 mmol, yield: 39%) as colorless crystals.

Physico-chemical properties of N-cyano-N'-(3-nitroxypropyl)-3-pyridinecarboximidamide

MP: 124.9°-125.8° C.;

IR spectrum: ($cm^{-1}$, KBr) 2180, 1620, 1600, 1560, 1280;

NMR spectrum: (500 MHz, $CDCl_3$-$CD_3OD$) δ (ppm) 8.75-8.70 (2H), 8.10 (1H, dt, J=2.4, 7.8Hz), 7.54 (1H, dd, J=5.2, 7.8Hz), 4.59 (2H, t, J=6.0Hz), 3.61 (2H, t, J=6.0Hz), 2.14 (2H, quint, J=6.0Hz);

| Elementary Analysis: | C | H | N |
|---|---|---|---|
| Calculated: | 48.19 | 4.45 | 28.10 |
| Found: | 48.16 | 4.29 | 27.93 (%) |
| | ($C_{10}H_{11}N_5O_3$) | | |

Example 1)-15

Preparation of N-cyano-N'-(3,3-dimethylbutyl)-3-pyridinecarboximidamide (method i)

Isopropyl N-cyano-3-pyridinecarboximidate (0.60 g, 3.2 mmol) was dissolved in methanol (10 ml), and 3,3-dimethylbutylamine (0.36 g, 3.6 mmol) was added. The mixture was stirred at room temperature for 20 minutes. After the reaction was completed, the reaction solution was concentrated under reduced pressure, and the concentrated residue was crystallized from dichloromethane-diethyl ether to give the title compound (0.46 g, 2.0 mmol, yield: 63%) as colorless needles.

Physico-chemical properties of N-cyano-N'-(3,3-dimethylbutyl)-3-pyridinecarboximidamide

MP: 168.0°-168.2° C.;

IR spectrum: ($cm^{-1}$, KBr) 3250, 2970, 2190, 1590, 1560, 720;

NMR spectrum: (100 MHz, $CDCl_3$) δ (ppm) 10 8.70 (2H, m), 7.96 (1H, d, J=8.6Hz), 7.42 (1H, dd, J=5.5, 8.6Hz), 6.88 (1H, br s), 3.50 (2H, m), 1.58 (2H, m), 1.00 (9H, s);

| Elementary Analysis: | C | H | N |
|---|---|---|---|
| Calculated: | 67.80 | 7.88 | 24.32 |
| Found: | 67.69 | 7.95 | 24.36 (%) |
| | ($C_{13}H_{18}N_4$) | | |

Example 1)-16

Preparation of N-cyano-N'-(4-methylphenyl) 3-pyridinecarboximidamide (method i)

Isopropyl N-cyano-3-pyridinecarboximidate (0.50 g, 2.6 mmol) was dissolved in methanol (10 ml), and 4-methylaniline (0.31 g, 2.9 mmol) was added. The mixture was stirred at room temperature for 30 minutes. After the reaction was completed, the reaction solution was concentrated under reduced pressure, and the concentrated residue thus obtained was crystallized from dichloromethane-diethyl ether to give the title compound (0.56 g, 2.4 mmol, yield: 90%) as colorless needles.

Physico-chemical properties of N-cyano-N'-(4-methylphenyl)-3-pyridinecarboximidamide

MP: 202.5°-203.0° C.;

IR spectrum: ($cm^{-1}$, KBr) 3200, 2180, 1580, 1550, 710;

NMR spectrum: (100 MHz, $CDCl_3$-$CD_3OD$) δ (ppm) 8.86 (1H, s), 8.78 (1H, br s), 8.18 (1H, br s), 7.60 (3H, br s), 7.22 (2H, m), 2.39 (3H, s);

| Elementary Analysis: | C | H | N |
|---|---|---|---|
| Calculated: | 71.17 | 5.12 | 23.71 |
| Found: | 71.06 | 5.15 | 23.65 (%) |
| | ($C_{14}H_{12}N_4$) | | |

Example 1)-17

Preparation of N-cyano-N'-benzyl-3 -pyridinecarboximidamide (method i)

Isopropyl N-cyano-3-pyridinecarboximidate (0.50 g, 2.6 mmol) was dissolved in methanol (10 ml), and benzylamine (0.31 g, 2.9 mmol) was added. The mixture was stirred at room temperature for 30 minutes. After the reaction was completed, the reaction solution was concentrated under reduced pressure, and the concentrated residue thus obtained was crystallized from methanoldiethyl ether to give the title compound (0.44 g, 1.8 mmol, yield: 72%) as colorless needles.

Physico-chemical properties of N-cyano-N'-benzyl-3-pyridinecarboximidamide

MP: 104°-104.5° C.;

IR spectrum: ($cm^{-1}$, KBr) 3230, 3100, 2170, 1580, 1550, 710;

NMR spectrum: (100 MHz, $CDCl_3$-$CD_3OD$) δ (ppm) 8.70 (2H, br s), 8.08 (1H, dt, J=2.9, 7.9Hz), 25 7.50 (1H, dd, J=4.8, 7.9Hz), 7.36 (5H, s), 4.62 (2H, t, J=3.4Hz);

| Elementary Analysis: | C | H | N |
|---|---|---|---|
| Calculated: | 71.17 | 5.12 | 23.71 |
| Found: | 71.00 | 5.16 | 23.62 (%) |
| | ($C_{14}H_{12}N_4$) | | |

Example 1)-18

Preparation of N-cyano-N'-(4-methylbenzyl)-3-pyridinecarboximidamide (method i)

Isopropyl N-cyano-3-pyridinecarboximidate (0.50 g, 2.6 mmol) was dissolved in methanol (5 ml), and 4-methylbenzylamine (0.35 g, 2.9 mmol) was added. The mixture was stirred at room temperature for 30 minutes. After the reaction was completed, the reaction solution was concentrated under reduced pressure, and the concentrated residue thus obtained was crystallized from diethyl ether to give the title compound (0.60 g, 2.4 mmol, yield: 91%) as colorless powder.

Physico-chemical properties of N cyano-N'-(4-methylbenzyl)-3-pyridinecarboximidamide

MP: 150.0°-150.5° C.;

IR spectrum: ($cm^{-1}$, KBr) 3270, 2180, 1580, 1560;

NMR spectrum: (100 MHz, $CDCl_3$—$CD_3OD$) δ (ppm) 8.72 (2H, m), 8.05 (1H, m), 7.57 (1H, dd, J=6.2, 7.5Hz), 7.20 (4H, s), 4.59 (2H, s), 2.30 (3H, s);

| Elementary Analysis: | C | H | N |
|---|---|---|---|
| Calculated: | 71.98 | 5.64 | 22.38 |

-continued

| Elementary Analysis: | C | H | N |
|---|---|---|---|
| Found: | 71.72 | 5.78 | 22.24 (%) |
| | ($C_{15}H_{14}N_4$) | | |

Example 1)-19

Preparation of N-cyano-N'-(4-methoxybenzyl)-3-pyridinecarboximidamide (method i)

Isopropyl N-cyano-3-pyridinecarboximidate (0.50 g, 2.6 mmol) was dissolved in methanol (10 ml), and 4-methoxybenzylamine (0.40 g, 2.9 mmol) was added. The mixture was stirred at room temperature for 40 minutes. After the reaction was completed, the reaction solution was concentrated under reduced pressure, and the concentrated residue thus obtained was crystallized from methanol-diethyl ether to give the title compound (0.50 g, 2.1 mmol, yield: 80%) as colorless powder.

Physico-chemical properties of N-cyano-N'-(4-methoxybenzyl)-3-pyridinecarboximidamide

MP: 160.5°-162.5° C.;

IR spectrum: ($cm^{-1}$, KBr) 3230, 1590, 1550, 1510, 1250;

NMR spectrum: (100 MHz, $CDCl_3$—$CD_3OD$) δ (ppm) 8.73 (2H, m), 8.08 (1H, m), 7.58 (1H, m), 7.32 (2H, d, J=9.2Hz), 6.91 (2H, d, J=9.2Hz), 4.59 (2H, s), 3.78 (3H, s);

| Elementary Analysis: | C | H | N |
|---|---|---|---|
| Calculated: | 67.65 | 5.30 | 21.04 |
| Found: | 67.88 | 5.28 | 21.04 (%) |
| | ($C_{15}H_{14}N_4O$) | | |

Example 1)-20

Preparation of N-cyano-N'-(4-dimethylaminobenzyl)-3-pyridinecarboximidamide (method i)

Isopropyl N-cyano-3-pyridinecarboximidate (0.50 g, 2.6 mmol) was dissolved in methanol (5 ml), and a solution of p-(dimethylamino)benzylamine dihydrochloride (0.65 g, 2.9 mmol) and triethylamine (0.64 g, 6.4 mmol) in methanol (5 ml) were added. The mixture was stirred at room temperature for 6 hours. After the reaction was completed, the reaction solution was concentrated under reduced pressure, and the concentrated residue thus obtained was extracted with ethyl acetate (50 ml×3). The ethyl acetate layer was washed with water (50 ml), dried over anhydrous sodium sulfate and concentrated under reduced pressure. The residual concentrate thus obtained was subjected to chromatography on a silica gel column (WAKO GEL C-200, 30 g) eluting with chloroformmethanol (100:1). The eluted fractions were concentrated under reduced pressure and then crystallized from methanol-diethyl ether to give the title compound (0.63 g, 2.3 mmol, yield: 85%) as colorless powder.

Physico-chemical properties of N-cyano-N'-(4-dimethylaminobenzyl)-3-pyridinecarboximidamide

MP: 148.8°-152.0° C.;

IR spectrum: ($cm^{-1}$, KBr) 2180, 1580, 1550, 1530;

NMR spectrum: (100 MHz, $CDCl_3$-$CD_3OD$) δ (ppm) 8.70 (2H, m), 8.06 (1H, m), 7.57 (1H, dd, J=5.2, 7.5Hz), 7.25 (2H, d, J=9.2Hz), 6.76 (2H, d, J=9.2Hz), 4.53 (2H, s), 2.92 (6H, s);

| Elementary Analysis: | C | H | N |
|---|---|---|---|
| Calculated: | 68.80 | 6.13 | 25.07 |
| Found: | 68.56 | 6.09 | 24.97 (%) |
| | ($C_{16}H_{17}N_5$) | | |

Example 1)-21

Preparation of N-cyano-N'-[4 (trifluoromethyl)benzyl]-3-pyridinecarboximidamide (method i)

Isopropyl N-cyano-3-pyridinecarboximidate (0.50 g, 2.6 mmol) was dissolved in methanol (10 ml), and 4-(trifluoromethyl)benzylamine (0.51 g, 2.9 mmol) was added. The mixture was stirred at room temperature for 1 hour. After the reaction was completed, the reaction solution was concentrated under reduced pressure, and the concentrated residue thus obtained was crystallized from diethyl ether to give the title compound (0.53 g, 1.7 mmol, yield: 66%) as colorless crystals.

Physico-chemical properties of N-cyano-N'-[4-(trifluoromethyl)benzyl]-3-pyridinecarboximidamide

MP: 201.0°-201.5° C.;

IR spectrum: ($cm^{-1}$, KBr) 2170, 1590, 1580, 1550, 1330;

NMR spectrum: (100 MHz, $CDCl_3$—$CD_3OD$) δ (ppm) 8.80-8.70 (2H), 8.11 (1H, d, J=7.8Hz), 7.75-7.40 (5H), 4.70 (2H, s);

| Elementary Analysis: | C | H | N |
|---|---|---|---|
| Calculated: | 59.21 | 3.64 | 18.41 |
| Found: | 59.14 | 3.62 | 18.17 (%) |
| | ($C_{15}H_{11}N_4F_3$) | | |

Example 1)-22

Preparation of N-cyano-N'-(4-chlorobenzyl)-3-pyridinecarboximidamide (method i)

Isopropyl N-cyano-3-pyridinecarboximidate (0.50 g, 2.6 mmol) was dissolved in methanol (10 ml), and 4-chlorobenzylamine (0.41 g, 2.9 mmol) was added. The mixture was stirred at room temperature for 1.5 hours. After the reaction was completed, the reaction solution was concentrated under reduced pressure, and the concentrated residue thus obtained was crystallized from methanol-diethyl ether to give the title compound (0.65 g, 2.4 mmol, yield: 91%) as colorless powder.

Physico-chemical properties of N-cyano-N'-(4-chlorobenzyl)-3-pyridinecarboximidamide

MP: 163.5°-166.0° C.;

IR spectrum: ($cm^{-1}$, KBr) 3250, 2180, 1580, 1550;

NMR spectrum (100 MHz, $CDCl_3$-$CD_3OD$) δ (ppm) 8.75 (2H, m), 8.10 (1H, m), 7.59 (1H, dd, J=5.5, 7.9Hz), 7.40 (4H, s), 4.54 (2H, s);

| Elementary Analysis: | C | H | N |
|---|---|---|---|
| Calculated: | 62.11 | 4.10 | 20.70 |
| Found: | 61.94 | 4.11 | 20.65 (%) |
| | ($C_{14}H_{11}N_4Cl$) | | |

Example 1)-23

Preparation of N-cyano-N'-(4-nitrobenzyl)-3-pyridinecarboximidamide (method i)

Isopropyl N-cyano-3-pyridinecarboximidate (0.50 g, 2.6 mmol) was dissolved in methanol (5 ml), and a solution of p-nitrobenzylamine hydrochloride (0.55 g, 2.9 mmol) and triethylamine (0.32 g, 3.2 mmol) in methanol (5ml) was added. The mixture was stirred at room temperature for 2 hours. After the reaction was completed, the reaction solution was concentrated under reduced pressure, and the concentrated residue thus obtained was crystallized from methanol-diethyl ether to give the title compound (0.70 g, 2.5 mmol, yield: 95%) as colorless powder.

Physico-chemical properties of N-cyano-N'-(4-nitrobenzyl)-3-pyridinecarboximidamide

MP: 206.2°-207.5° C.;

IR spectrum: ($cm^{-1}$, KBr) 2180, 1580, 1550, 1520, 1350, 1340;

NMR spectrum: (100 MHz, $CDCl_3$—$CD_3OD$) δ (ppm) 8.83 (2H, m), 8.4-8.0 (3H), 7.8-7.5 (3H), 4.75 (2H, d, J=6.2Hz);

| Elementary Analysis: | C | H | N |
|---|---|---|---|
| Calculated: | 59.78 | 3.94 | 24.90 |
| Found: | 59.50 | 4.06 | 24.88 (%) |
| | ($C_{14}H_{11}N_5O_2$) | | |

Example 1)-24

Preparation of N-cyano-N'-(3,4-dichlorobenzyl)-3-pyridinecarboximidamide (method i)

Isopropyl N-cyano-3-pyridinecarboximidate (0.50 g, 2.6 mmol) was dissolved in methanol (10 ml), and 3,4-dichlorobenzylamine (0.51 g, 2.9 mmol) was added. The mixture was stirred at room temperature for 3 hours. After the reaction was completed, the reaction solution was concentrated under reduced pressure, and the concentrated residue thus obtained was crystallized from diethyl ether to give the title compound (0.42 g, 1.4 mmol, yield: 52%) as colorless crystals.

Physico-chemical properties of N-cyano-N'-(3,4-dichlorobenzyl)-3-pyridinecarboximidamide

MP: 149.5°-150.0° C.;

IR spectrum: ($cm^{-1}$, KBr) 2170, 1590, 1550;

NMR spectrum: (500 MHz, $CDCl_3$-$CD_3OD$) δ (ppm) 8.75-8.72 (2H), 8.11 (1H, dt, J=2.0, 8.2Hz), 7.54 (1H, dd, J=5.2, 8.2Hz), 7.48 (1H, d, J=2.0Hz), 7.46 (1H, d, J=8.4Hz), 7.25 (1H, dd, J=2.0, 8.4Hz), 4 60 (2H, s);

| Elementary Analysis: | C | H | N |
|---|---|---|---|
| Calculated: | 55.10 | 3.30 | 18.36 |
| Found: | 54.99 | 3.01 | 18.09 (%) |
| | ($C_{14}H_{10}N_4Cl_2$) | | |

Example 1)-25

Preparation of N-cyano-N'-[3,5-bis(trifluoromethyl)benzyl]-3-pyridinecarboximidamide (method i)

Isopropyl N-cyano-3-pyridinecarboximidate (0.50 g, 2.6 mmol) was dissolved in methanol (10 ml), and 3,5-bis(trifluoromethyl)benzylamine (0.71 g, 2.9 mmol) was added. The mixture was stirred at room temperature for 1 hour. After the reaction was completed, the reaction solution was concentrated under reduced pressure, and the concentrated residue thus obtained was crystallized from diethyl ether to give the title compound (0.34 g, 0.91 mmol, yield: 35%) as colorless crystals.

Physico-chemical properties of N-cyano-N'-[3,5-bis(-trifluoromethyl)benzyl]-3-pyridinecarboximidamide

MP: 172.0°-172.1° C.;

IR spectrum: ($cm^{-1}$, KBr) 2180, 1580, 1280, 1180, 1120;

NMR spectrum: (500 MHz, $CDCl_3$—$CD_3OD$) δ (ppm) 8.76-8.72 (2H), 8.12 (1H, dt, J=2.0, 8.2Hz), 7.90-7.83 (3H), 7.54 (1H, dd, J=5.0, 8.2Hz),

| Elementary Analysis: | C | H | N |
|---|---|---|---|
| Calculated: | 51.64 | 2.71 | 15.05 |
| Found: | 51.49 | 2.56 | 14.95 (%) |
| | ($C_{16}H_{10}N_4F_6$) | | |

Example 1)-26

Preparation of N-cyano-N'-(3-benzyloxybenzyl)-3-pyridinecarboximidamide (method i)

Isopropyl N-cyano-3-pyridinecarboximidate (0.30 g, 1.6 mmol) was dissolved in methanol (10 ml), and 3-benzyloxybenzylamine (0.41 g, 1.9 mmol) was added. The mixture was stirred at room temperature for 2 hours. After the reaction was completed, the reaction solution was concentrated under reduced pressure. The concentrated residue was subjected to chromatography on a silica gel column (WAKO GEL C-200, 30 g). Elution with chloroform-methanol (100:1) was conducted, the eluted fractions were concentrated under reduced pressure, and the concentrated residue thus obtained was crystallized from methanol-diethyl ether to give the title compound (0.48 g, 1.4 mmol, yield: 88%) as colorless crystals.

Physico-chemical properties of N-cyano-N'-(3-benzyloxybenzyl)-3-pyridinecarboximidamide

MP: 122.0°-122.2° C.;

IR spectrum: ($cm^{-1}$, KBr) 2170, 1590;

NMR spectrum: (500 MHz, $CDCl_3$) δ (ppm) 8.66-8.62 (2H), 7.98 (1H, dt, J=2.0, 7.9Hz), 7.44-7.26 (6H), 6.96-6.86 (4H), 5.06 (2H, s), 4.61 (2H, d, J=5.8Hz);

| Elementary Analysis: | C | H | N |
|---|---|---|---|
| Calculated: | 73.67 | 5.30 | 16.36 |
| Found: | 73.54 | 5.19 | 16.11 (%) |
| | ($C_{21}H_{18}N_4O$) | | |

Example 1)-27

Preparation of N-cyano-N'-(2-phenylethyl)-3-pyridinecarboximidamide (method i)

Isopropyl N-cyano-3-pyridinecarboximidate (0.50 g, 2.6 mmol) was dissolved in methanol (10 ml), and 2-phenylethylamine (0.35 g, 2.9 mmol) was added. The mixture was stirred at room temperature for 40 minutes. After the reaction was completed, the reaction solution was concentrated under reduced pressure, and the concentrated residue thus obtained was crystallized from methanol-diethyl ether to give the title compound (0.45 g, 1.8 mmol, yield: 68%) as colorless needles.

Physico-chemical properties of N-cyano-N'-(2-phenylethyl)-3-pyridinecarboximidamide

MP: 149.5°-150.0° C.;

IR spectrum: ($cm^{-1}$, KBr) 3220, 3120, 2180, 1590, 1550, 710;

NMR spectrum: (100 MHz, $CDCl_3$—$CD_3OD$) δ (ppm) 8.70 (1H, dd, J=2.0, 5.1Hz), 8.61 (1H, dd, J=1.0, 2.4Hz), 8.00 (1H, ddd, J=2.0, 2.4, 8.2Hz), 7.50 (1H, ddd, J=1.0, 5.1, 8.2Hz), 7.26 (5H, br s), 3 74 (2H, t, J=7.8Hz), 2.98 (2H, t, J=7.8Hz);

| Elementary Analysis: | C | H | N |
|---|---|---|---|
| Calculated: | 71.98 | 5.64 | 22.38 |
| Found: | 71.70 | 5.68 | 22.30 (%) |
| | ($C_{15}H_{14}N_4$) | | |

Example 1)-28

Preparation of N-cyano-N'-[2-(2-methoxyphenyl)ethyl]-3-pyridinecarboximidamide (method i)

Isopropyl N-cyano-3-pyridinecarboximidate (0.50 g, 2.6 mmol) was dissolved in methanol (10 ml), and 2-(2-methoxyphenyl)ethylamine (0.44 g, 2.9 mmol) was added. The mixture was stirred at room temperature for 6 hours. After the reaction was completed, the reaction solution was concentrated under reduced pressure, and the residue thus obtained was subjected to chromatography on a silica gel column (WAKO GEL C-200, 30 g) eluting with chloroform-methanol (100:1). The eluted fractions were concentrated under reduced pressure, and the concentrated residue thus obtained was crystallized from chloroformhexane to give the title compound (0.50 g, 1.8 mmol, yield: 68%) as colorless crystals.

Physico-chemical properties of N-cyano-N'-[2-(2-methoxyphenyl)ethyl]-3-pyridinecarboximidamide

MP: 123.5° C.;

IR spectrum: ($cm^{-1}$, KBr) 2170, 1580, 1550;

NMR spectrum: (500 MHz, $CDCl_3$) δ (ppm) 8.76 (1H, d, J=4.4Hz), 8.63 (1H, s), 8.03 (1H, d, J=9.6Hz), 7.44 (1H, dd, J=4.4, 9.6Hz), 7.28 (1H, t, J=8.7Hz), 7.19 (1H, d, J=8.7Hz), 6.98 (1H, t, J=8.7Hz), 6.92 (1H, d, J=8.7Hz), 6.70 (1H, br s), 3.82 (3H, s), 3.75 (2H, m), 3.03 (2H, t, J=7.1Hz);

| Elementary Analysis: | C | H | N |
|---|---|---|---|
| Calculated: | 68.55 | 5.75 | 19.99 |
| Found: | 68.72 | 5.71 | 19.91 (%) |
| | ($C_{16}H_{16}N_4O$) | | |

Example 1)-29

Preparation of N-cyano-N'-[2-(2-chlorophenyl)ethyl]-3-pyridinecarboximidamide (method i)

Isopropyl N-cyano-3-pyridinecarboximidate (0.50 g, 2.6 mmol) was dissolved in methanol (10 ml), and 2-(2-chlorophenyl)ethylamine (0.45 g, 2.9 mmol) was added. The mixture was stirred at room temperature for 7 hours. After the reaction was completed, the reaction solution was concentrated under reduced pressure. The residual concentrate was subjected to chromatography on a silica gel column (WAKO GEL C-200, 30 g) eluting with chloroform-methanol (100:1). The eluted fractions were concentrated under reduced pressure, and the concentrated residue thus obtained was crystallized from methanolhexane to give the title compound (0.56 g, 2.0 mmol, yield: 75%) as colorless crystals.

Physico-chemical properties of N-cyano-N'-[2-(2-chlorophenyl)ethyl]-3-pyridinecarboximidamide

MP: 138.5°-140.0° C.;

IR spectrum: ($cm^{-1}$, KBr) 2180, 1590;

NMR spectrum: (100 MHz, $CDCl_3$—$CD_3OD$) δ (ppm) 8.77 (1H, dd, J=1.7, 4.8Hz), 8.68 (1H, d, J=2.0Hz), 8.12 (1H, m), 7.60-7.25 (5H), 3.76 (2H, t, J=7.6Hz), 3.14 (1H, t, J=7.6Hz);

| Elementary Analysis: | C | H | N |
|---|---|---|---|
| Calculated: | 63.27 | 4.60 | 19.68 |
| Found: | 63.17 | 4.64 | 19.45 (%) |
| | ($C_{15}H_{13}N_4Cl$) | | |

Example 1)-30

Preparation of N-cyano-N'-[2-(4-chlorophenyl)ethyl]-3-pyridinecarboximidamide (method i)

Isopropyl N-cyano-3-pyridinecarboximidate (0.60 g, 3.2 mmol) was dissolved in methanol (10 ml), and 2-(4-chlorophenyl)ethylamine (0.55 g, 3.5 mmol) was added. The mixture was stirred at room temperature for 2.5 hours. After the reaction was completed, the reaction solution was concentrated under reduced pressure. The residual concentrate was subjected to chromatography on a silica gel column (WAKO GEL C-200, 50 g) eluting with chloroform-methanol (100:1). The eluted fractions were concentrated under reduced pressure, and the concentrated residue thus obtained was further crystallized from methanol-diethyl ether to give the title compound (0.71 g, 2.5 mmol, yield: 79%) as colorless powder.

Physico-chemical properties of N-cyano-N'-[2-(4-chlorophenyl)ethyl]-3-pyridinecarboximidamide

MP: 121.8°-122.0° C.;

IR spectrum: ($cm^{-1}$, KBr) 3240, 3100, 2180, 1590, 1550, 710;

NMR spectrum: (100 MHz, $CDCl_3$) δ (ppm) 8.8-8.5 (2H), 7.97 (1H, d, J=9.9Hz), 7.5-7.1 (5H), 6.70 (1H, br s), 3.78 (2H, q, J=6.8Hz), 2.99 (2H, t, J=6.8Hz);

| Elementary Analysis: | C | H | N |
|---|---|---|---|
| Calculated: | 63.27 | 4.60 | 19.68 |
| Found: | 63.14 | 4.68 | 19.61 (%) |
| | ($C_{15}H_{13}N_4Cl$) | | |

Example 1)-31

Preparation of N-cyano-N'-[2-(4-benzylaminophenyl)ethyl]-3-pyridinecarboximidamide (method i)

a) Isopropyl N-cyano-3-pyridinecarboximidate (1.0 g, 5.3 mmol) was dissolved in methanol (15 ml), and 2-(4-aminophenyl)ethylamine (0.80 g, 5.8 mmol) was added. The mixture was stirred at room temperature for 1 hour. After the reaction was completed, the reaction solution was concentrated under reduced pressure. The residual concentrate was crystallized from methanol-diethyl ether pyridinecarboximidamide (0.88 g, 3.3 mmol, yield: 63%) as colorless needles.

Physico-chemical properties of N-cyano-N'-[2-(4-aminophenyl)ethyl]-3-pyridinecarboximidamide

MP: 154.5°-155.2° C.;

IR spectrum: ($cm^{-1}$, KBr) 2160, 1580, 1540;

NMR spectrum: (500 MHz, $CDCl_3$-$CD_3OD$) δ (ppm) 8.70 (1H, dd, J=1.8, 5.4Hz), 8.62 (1H, d, J=1.8Hz), 8.01 (1H, dt, J=1.8, 8.6Hz), 7.51 (1H, dd, J=5.4, 8.6Hz), 7.03 (2H, d, J=8.4Hz), 6.70 (2H, d, J=8.4Hz), 3.67 (2H, t, J=7.4Hz), 2.87 (2H, t, J=7.4Hz);

| Elementary Analysis: | C | H | N |
|---|---|---|---|
| Calculated: | 67.91 | 5.70 | 26.40 |
| Found: | 67.80 | 5.66 | 26.17 (%) |
| | ($C_{15}H_{15}N_5$) | | |

b) N-cyano-N'-[2-(4-aminophenyl)ethyl]-3-pyridinecarboximidamide (0.20 g, 0.75 mmol) was dissolved in methanol (15 ml), and benzaldehyde (0.12 g, 1.13 mmol) and sodium cyanoborohydride (0.10 g, 1.59 mmol) were added. The mixture was stirred at room temperature for 2 hours. After the reaction was completed, the reaction solution was concentrated under reduced pressure. The residue thus obtained was extracted with chloroform (50 ml×3). The chloroform layer was washed with water (100 ml), dried over anhydrous sodium sulfate and concentrated under reduced pressure. The residual concentrate was subjected to chromatography on a silica gel column (WAKO GEL C-200, 50 g) eluting with chloroform-methanol (100:1). The eluted fractions were concentrated under reduced pressure and crystallized from methanol-diethyl ether to give the title compound (0.12 g, 0.34 mmol, yield: 75%) as colorless needles.

Physico-chemical properties of N-cyano-N'-[2 (4-benzylaminophenyl)ethyl]-3-pyridinecarboximidamide

MP: 131.5°-132.0° C.;

IR spectrum: ($cm^{-1}$, KBr) 2180, 1590, 1550;

NMR spectrum: (500 MHz, $CDCl_3$—$CD_3OD$) δ (ppm) 8.70 (1H, dd, J=2.0, 5.2Hz), 8.62 (1H, d, J=2.0Hz), 8.00 (1H, dt, J=2.0, 8.0Hz), 7.49 (1H, dd, J=5.2, 8.0Hz), 7.38-7.25 (5H), 7.04 (2H, d, J=8.2Hz), 6.63 (2H, d, J=8.2Hz), 4.32 (2H, s), 3.66 (2H, t, J=7.4Hz), 2.86 (2H, t, J=7.4Hz);

| Elementary Analysis: | C | H | N |
|---|---|---|---|
| Calculated: | 74.34 | 5.96 | 19.70 |
| Found: | 74.21 | 6.11 | 19.48 (%) |
| | ($C_{22}H_{21}N_5$) | | |

Example 1)-32

Preparation of N-cyano-N'-[2-(4-nitrophenyl)-2-nitroxyethyl]-3-pyridinecarboximidamide (method i)

Isopropyl N-cyano-3-pyridinecarboximidate (0.22 g, 1.2 mmol) was dissolved in methanol (10 ml), and 2-(4-nitrophenyl)-2-nitroxyethylamine nitrate (0.40 g, 1.4 mmol) and sodium methoxide (0.14 g, 2.6 mmol) were added. The mixture was stirred at room temperature for 17 hours. After the reaction was completed, the reaction solution was concentrated under reduced pressure. The residual concentrate was extracted with chloroform (100 ml×3). The chloroform layer was washed with water (150 ml), dried over anhydrous sodium sulfate and concentrated under reduced pressure. The residual concentrate was subjected to chromatography on a silica gel column (WAKO GEL C-200, 30 g) eluting with chloroform-methanol (50:1). The eluted fractions were concentrated under reduced pressure and crystallized from methanol-diethyl ether to give the title compound (0.13 g, 0.36 mmol, yield: 31%) as colorless crystals.

Physico-chemical properties of N-cyano-N'-[2-(4-nitrophenyl)-2-nitroxyethyl]-3-pyridinecarboximidamide

MP: 86.5°-89.0° C.;

IR spectrum: ($cm^{-1}$, KBr) 2180, 1640, 1590, 1520, 1380, 1350;

NMR spectrum: (500 MHz, $CDCl_3$—$CD_3OD$) δ (ppm) 8.33 (2H, d, J=8.7Hz), 8.14 (1H, dd, J=4.0, 8.7Hz), 7.69 (2H, d, J=8.7Hz), 6.32 (1H, d, J=3.5, 9.3Hz), 3.76 (2H, m);

| Elementary Analysis: | C | H | N |
|---|---|---|---|
| Calculated: | 50.57 | 3.39 | 23.59 |
| Found: | 50.50 | 3.49 | 23.33 (%) |
| | ($C_{15}H_{12}N_6O_5$) | | |

Example 1)-33

Preparation of N-cyano-N'-(3-phenylpropyl)-3-pyridinecarboximidamide (method i)

Isopropyl N-cyano-3-pyridinecarboximidate (0.60 g, 3.2 mmol) was dissolved in methanol (10 ml), and 3-phenylpropylamine (0.47 g, 3.5 mmol) was added. The mixture was stirred at room temperature for 50 minutes. After the reaction was completed, the reaction solution was concentrated under reduced pressure. The residual concentrate thus obtained was subjected to chromatography on a silica gel column (WAKO GEL C-200, 30 g) eluting with chloroform-methanol (100:1). The eluted fractions were concentrated under reduced pressure and crystallized from methanol-diethyl ether to give the title compound (0.67 g, 2.5 mmol, yield: 80%) as colorless needles.

Physico-chemical properties of N-cyano-N'-(3-phenylpropyl)-3-pyridinecarboximidamide

MP: 98.5°-99.1° C.;

IR spectrum: ($cm^{-1}$, KBr) 3240, 2180, 1590, 1550, 1440, 710;

NMR spectrum: (100 MHz, $CDCl_3$) δ (ppm) 8.7-8 4 (2H), 7.80 (1H, m), 7.4-7.0 (7H), 3.49 (2H, q, J=7.4Hz), 2.70 (2H, t, J=7.4Hz), 1.98 (2H, quint, J=7.4Hz);

| Elementary Analysis: | C | H | N |
|---|---|---|---|
| Calculated: | 72.70 | 6.10 | 21.20 |
| Found: | 72.58 | 6.21 | 21.17 (%) |
| | ($C_{16}H_{16}N_4$) | | |

Example 1)-34

Preparation of N-cyano-N'-diphenyl methyl-3-pyridinecarboximidamide hydrochloride (method i)

Isopropyl N-cyano-3-pyridinecarboximidate (0.50 g, 2.6 mmol) was dissolved in methanol (10 ml), and aminodiphenylmethane (0.54 g, 2.9 mmol) was added. The mixture was stirred at room temperature for 1 hour. After the reaction was completed, the reaction solution was concentrated under reduced pressure. The residual concentrate thus obtained was subjected to chromatography on a silica gel column (WAKO GEL C-200, 40 g) eluting with chloroform-methanol (100:1). The eluted fractions were concentrated under reduced pressure to give N-cyano-N'-diphenylmethyl-3-pyridinecarboximidamide (0.48 g, 1.5 mmol, yield: 58%) as colorless syrup. Next, to this syrup was added a solution of 5% hydrogen chloride in methanol (2 ml) to form a solution. The solution was further crystallized from methanol-diethyl ether to give N-cyano-N'-diphenylmethyl-3-pyridinecarboximidamide hydrochloride as colorless powder.

Physico-chemical properties of N-cyano-N'-diphenylmethyl-3-pyridinecarboximidamide hydrochloride

MP: 164.0°-165.2° C.;

IR spectrum: ($cm^{-1}$, KBr) 3020, 2180, 1580, 700;

NMR spectrum: (100 MHz, $CDCl_3$—$CD_3OD$) δ (ppm) 8.95 (2H, m), 8.58 (1H, m), 8.00 (1H, m), 7.4-7.2 (12H), 6.50 (1H, s);

| Elementary Analysis: | C | H | N |
|---|---|---|---|
| Calculated: | 68.86 | 4.91 | 16.23 |
| Found: | 68.61 | 5.04 | 16.15 (%) |
| | ($C_{20}H_{16}N_4$.HCl) | | |

Example 1)-35

Preparation of N-cyano-N'-(1,2-diphenylethyl)-3-pyridinecarboximidamide hydrochloride (method i)

Isopropyl N-cyano-3-pyridinecarboximidate (0.60 g, 3.2 mmol) was dissolved in methanol (10 ml), and 1,2-diphenylethylamine (0.69 g, 3.5 mmol) was added. The mixture was stirred at room temperature for 45 minutes. After the reaction was completed, the reaction solution was concentrated under reduced pressure. The residual concentrate thus obtained was subjected to chromatography on a silica gel column (WAKO GEL C-200, 50 g) eluting with chloroform-methanol (100:1). The eluted fractions were concentrated under reduced pressure to give N-cyano-N'-(1,2-diphenylethyl)-3-pyridinecarboximidamide (0.60 g, 1.8 mmol, yield: 58%) as colorless syrup. Next, to this syrup was added a 5% hydrogen chloride solution in methanol (2.5 ml). The solution was crystallized from a methanol-diethyl ether to give N-cyano-N'-(1,2-diphenylethyl)-3-pyridinecarboximidamide hydrochloride as colorless powder.

Physico-chemical properties of N-cyano-N'-(1,2-diphenylethyl)-3-pyridinecarboximidamide hydrochloride

MP: 140.5°-143.0° C.;

IR spectrum: ($cm^{-1}$, KBr) 2180, 1570, 700;

NMR spectrum: (100 MHz, $CDCl_3$—$CD_3OD$) δ (ppm) 8.90 (1H, d, J=5.8Hz), 8.72 (1H, s), 8.48 (1H, d, J=9.6Hz), 8.10 (1H, dd, J=5.8, 9.6Hz), 7.6-7.2 (10H), 5.46 (1H, t, J=8.6Hz), 3.29 (2H, d, J=8.6Hz);

| Elementary Analysis: | C | H | N |
|---|---|---|---|
| Calculated: | 69.51 | 5.28 | 15.44 |
| Found: | 69.32 | 5.25 | 15.43 (%) |
| | ($C_{21}H_{18}N_4$.HCl) | | |

Example 1)-36

Preparation of N-cyano-N'-(2,2-diphenylethyl)-3-pyridinecarboximidamide hydrochloride (method i)

Isopropyl N-cyano-3-pyridinecarboximidate (0.50 g, 2.6 mmol) was dissolved in methanol (10 ml), and 2,2-diphenylethylamine (0.58 g, 2.9 mmol) was added. The mixture was stirred at room temperature for 2 hours. After the reaction was completed, the reaction solution was concentrated under reduced pressure. The residual concentrate thus obtained was subjected to chromatography on a silica gel column (WAKO GEL C 200, 30 g) eluting with chloroform-methanol (100:1). The eluted fractions were concentrated under reduced pressure to give N-cyano-N'-(2,2-diphenylethyl)-3-pyridinecarboximidamide (0.61 g, 1.9 mmol, yield: 71%) as colorless syrup. Next, to this syrup was added a 5% hydrogen chloride solution in methanol (2.5 ml). The solution was crystallized from methanol-diethyl ether to give N-cyano-N'-(2,2-diphenylethyl)-3-pyridinecarboximidamide hydrochloride as colorless powder.

Physico-chemical properties of N-cyano-N'-(2,2-diphenylethyl)-3-pyridinecarboximidamide hydrochloride

MP: 139.5°-142.0° C.;

IR spectrum: ($cm^{-1}$, KBr) 3040, 2170, 1610, 1580, 700;

NMR spectrum: (100 MHz, $CDCl_3$—$CD_3OD$) δ (ppm) 8.94 (1H, d, J=6.2Hz), 8.70 (1H, s), 8.41 (1H, d, J=8.6Hz), 8.08 (1H, dd, J=6.2, 8.6Hz), 4.60 (1H, t, J=8.9Hz), 4.19 (2H, d, J=8.9Hz);

| Elementary Analysis: | C | H | N |
|---|---|---|---|
| Calculated: | 69.51 | 5.28 | 15.44 |
| Found: | 69.19 | 5.46 | 15.20 (%) |
| | ($C_{21}H_{18}N_4$.HCl) | | |

Example 1)-37

Preparation of N-cyano-N'-(3,3-diphenylpropyl)-3-pyridinecarboximidamide (method i)

Isopropyl N-cyano-3-pyridinecarboximidate (0.60 g, 3.2 mmol) was dissolved in methanol (10 ml), and 3,3-diphenylpropylamine (0.74 g, 3.5 mmol) was added. The mixture was stirred at room temperature for 1 hour. After the reaction was completed, the reaction solution was concentrated under reduced pressure. The residual concentrate thus obtained was subjected to chromatography on a silica gel column (WAKO GEL C-200, 50 g) eluting with chloroform-methanol (100:1). The eluted fractions were concentrated under reduced pressure and crystallized from methanol-diethyl ether to give the title compound (0.68 g, 2.0 mmol, yield: 63%) as colorless powder.

Physico-chemical properties of N-cyano-N'-(3,3-diphenylpropyl)-3-pyridinecarboximidamide

MP: 150.9°-151.3° C.;

IR spectrum: ($cm^{-1}$, KBr) 2180, 1590, 1550, 700;

NMR spectrum: (100 MHz, $CDCl_3$) δ (ppm) 8.68 (1H, m), 8.50 (1H, s), 7.82 (1H, d, J=7.5Hz), 7.4-7.0 (11H), 6.54 (1H, br s), 4.00 (1H, t, J=8.6Hz), 3.51 (2H, q, J=8.6Hz), 2.43 (2H, q, J=8.6Hz);

| Elementary Analysis: | C | H | N |
|---|---|---|---|
| Calculated: | 77.62 | 5.92 | 16.46 |
| Found: | 77.60 | 5.92 | 16.43 (%) |
| | ($C_{22}H_{20}N_4$) | | |

Example 1)-38

Preparation of N-cyano-N'-(2-benzyloxy-2-phenylethyl)-3-pyridinecarboximidamide hydrochloride (method i)

Isopropyl N-cyano-3-pyridinecarboximidate (0.20 g, 1.1 mmol) was dissolved in methanol (5 ml), and 2-benzyloxy-2-phenylethylamine (0.26 g, 1.1 mmol) was added. The mixture was stirred at room temperature for 3 hours. After the reaction was completed, the reaction solution was concentrated under reduced pressure. The residual concentrate thus obtained was subjected to chromatography on a silica gel column (WAKO GEL C-200, 20 g) eluting with chloroform-methanol (100:1). The eluted fractions were concentrated under reduced pressure to give N-cyano-N'-(2-benzyloxy-2-phenylethyl)-3-pyridinecarboximidamide (0.24 g, 0.7 mmol, yield: 64%) as colorless syrup. Next, to this syrup was added a 5% hydrogen chloride in methanol (2 ml). The solution was crystallized from methanol-diethyl ether to give N-cyano-N'-(2-benzyloxy-2-phenylethyl)-3-pyridinecarboximidamide hydrochloride as colorless powder.

Physico-chemical properties of N-cyano-N'-(2-benzyloxy-2-phenylethyl]-3-pyridinecarboximidamide hydrochloride

MP: 163.0°-165.5° C.;

IR spectrum: ($cm^{-1}$, KBr) 2550, 2200, 1710, 1680;

NMR spectrum: (100 MHz, CDC13) δ (ppm) 9.00 (2H), 8.60 (1H, d, J=8.3Hz), 8.19 (1H, m), 7.60-7.20 (11H), 4.82 (1H, m), 4.42 (2H, m), 3.79 (2H, d, J=6.3Hz);

| | Elementary Analysis: | | |
|---|---|---|---|
| | C | H | N |
| Calculated: | 67.26 | 5.13 | 14.26 |
| Found: | 67.07 | 4.99 | 13.97 (%) |
| | ($C_{22}H_{20}N_4O.HCl$) | | |

Example 1)-39

Preparation of N-cyano-N'-[2-(3 ,4-dibenzyloxyphenyl)ethyl]-3-pyridinecarboximidamide hydrochloride (method i)

Isopropyl N-cyano-3-pyridinecarboximidate (0.25 g, 1.3 mmol) was dissolved in methanol (10 ml), and 3,4-(dibenzyloxy)phenethylamine hydrochloride (0.54 g, 1.5 mmol) and triethylamine (0.15 g, 1.5 mmol) were added. The mixture was stirred at room temperature for 45 minutes. After the reaction was completed, the reaction solution was concentrated under reduced pressure. The residual concentrate thus obtained was extracted with ethyl acetate (100 ml×3). The ethyl acetate layer was washed with water (100 ml), dried over anhydrous sodium sulfate and concentrated under reduced pressure. The residual concentrate was subjected to chromatography on a silica gel column (WAKO GEL C-200, 50 g) eluting with chloroform-methanol (100:1). The eluted fractions were concentrated under reduced pressure to give N-cyano-N'-[2-(3,4-dibenzyloxyphenyl)ethyl]-3-pyridinecarboximidamide (0.13 g, 0.3 mmol, yield: 21%) as colorless syrup. Next, to this syrup was added a 5% hydrogen chloride in methanol (2 ml). The solution was crystallized from methanol-diethyl ether to give N-cyano-N'-[2-(3,4-dibenzyloxyphenyl)ethyl]-3-pyridinecarboximidamide hydrochloride as colorless powder.

Physico-chemical properties of N-cyano-N'-[2-(3,4-dibenzyloxyphenyl)ethyl]-3-pyridinecarboximidamide hydrochloride

MP: 84.8°-85.5° C.;

IR spectrum: ($cm^{-1}$, KBr) 3400, 2180, 1610, 1590, 1260, 700;

NMR spectrum: (100 MHz, $CDCl_3$—$CD_3OD$) δ (ppm) 8.90 (2H), 8.60 (1H, m) 8.06 (1H, m), 7.5 7.3 (10H), 7.0-6.7 (3H), 5.16 (4H, m), 3.75 (2H, t, J=7.2Hz), 2.94 (2H, t, J=7.2Hz);

| | Elementary Analysis: | | |
|---|---|---|---|
| | C | H | N |
| Calculated: | 69.80 | 5.45 | 11.23 |
| Found: | 70.01 | 5.48 | 11.25 (%) |
| | ($C_{29}H_{26}N_4O_2.HCl$) | | |

Example 1)-40

Preparation of N-cyano-N'-3-(2,6-dimethoxypyridine)-3-pyridinecarboximidamide (method i)

Isopropyl N-cyano-3-pyridinecarboximidate (0.50 g, 2.6 mmol) was dissolved in methanol (10 ml), and 3-amino-2,6-dimethoxypyridine (0.45 g, 2.9 mmol) was added. The mixture was stirred at room temperature for 2 hours. After the reaction was completed, the reaction solution was concentrated under reduced pressure and crystallized from methanol-diethyl ether to give the title compound (0.35 g, 1.2 mmol, yield: 47%) as colorless needles.

Physico-chemical properties of N-cyano-N'-3-(2,6-dimethoxypyridine)-3-pyridinecarboximidamide

MP: 162.5°-163.5° C.;

IR spectrum: ($cm^{-1}$, KBr) 2180, 1580, 1550, 1490, 1470, 1390, 1330;

NMR spectrum: (100 MHz, $CDCl_3$—$CD_3OD$) δ (ppm) 9.0-8 7 (2H, m), 8.3-7.9 (2H, m), 7.57 (1H, dd, J=4.8, 7.9Hz), 6.40 (1H, d, J=8.9Hz), 4.02 (3H, s), 3.96 (3H, s);

| | Elementary Analysis: | | |
|---|---|---|---|
| | C | H | N |
| Calculated: | 59.36 | 4.63 | 24.72 |

-continued

| | Elementary Analysis: | | |
|---|---|---|---|
| | C | H | N |
| Found: | 59.06 | 4.68 | 24.48 (%) |
| | ($C_{14}H_{13}N_5O_2$) | | |

Example 1)-41

Preparation of N-cyano-N'-(2-nitroxyethyl)-4-pyridinecarboximidamide (method i)

a) 4 cyanopyridine (10.0 g, 96.1 mmol) was dissolved in isopropanol (50 ml), and sodium hydride (0.23 g, 9.6 mmol) from which oily matters had been removed by washing with ether was added. The mixture was stirred at room temperature for 6 hours. After the reaction was completed, the reaction solution was neutralized by adding acetic acid (0.64 g, 10.7 mmol) and concentrated under reduced pressure. To the residual concentrate was added diethyl ether (50 ml). Insolubles were removed by filtration, and the filtrate was concentrated under reduced pressure. To this concentrate was added hexane (80 ml), and deposited unreacted 4-cyanopyridine was removed by filtration. The filtrate was concentrated under reduced pressure to give crude isopropyl 4-pyridinecarboximidate (11.0 g) as a pale yellow oil.

Next, cyanamide (5.63 g, 133.9 mmol) and a phosphate buffer solution (pH 5.4, 60 ml) of $Na_2HPO_4$ (9.51 g, 67.0 mmol) and $NaH_2PO_4.2H_2O$ (41.8 g, 267.9 mmol) were added to the oil, and the mixture was stirred at room temperature for 8 hours. After the reaction was completed, the reaction solution was extracted with dichloromethane (100 ml×3), and the dichloromethane layer was dried over anhydrous sodium sulfate and concentrated under reduced pressure. The residual concentrate thus obtained was subjected to chromatography on a silica gel column (WAKO GEL C-200, 200 g). Eluting with hexane-diethyl ether (1:2) gave isopropyl N-cyano-4-pyridinecarboximidate (11.2 g, 59.2 mmol, yield: 62%) as pale yellow oil.

Physico-chemical properties of isopropyl N-cyano-4-pyridinecarboximidate

IR spectrum: ($cm^{-1}$, neat) 3250, 3000, 2250, 2200, 1620, 1590, 1380, 1310, 1100;

NMR spectrum: (100 MHz, $CD_3OD$) δ (ppm) 30 8.9–8.7, 8.0–7.7 (4H), 5.42 (1H, m, J=6.1Hz), 1.50 (6H, d, J=6.1Hz).

b) Isopropyl N-cyano-4-pyridinecarboximidate (0.50 g, 2.6 mmol) was dissolved in methanol (10 ml), and 2-nitroxyethylamine nitrate (0.57 g, 2.9 mmol) and sodium methoxide (0.18 g, 2.9 mmol) were added. The mixture was stirred at room temperature for 10 minutes. After the reaction was completed, the reaction solution was concentrated under reduced pressure. The residue thus obtained was extracted with dichloromethane (50 ml×3). The dichloromethane layer was dried over anhydrous sodium sulfate and concentrated under reduced pressure. The residual concentrate was crystallized from dichloromethane-diethyl ether to give the title compound (0.37 g, 1.6 mmol, yield: 61%) as colorless needles.

Physico-chemical properties of N-cyano-N'-(2-nitroxyethyl)-4-pyridinecarboximidamide

MP: 102.5°–103.0° C.;

IR spectrum: ($cm^{-1}$, KBr) 2180, 1640, 1580, 1540, 1290, 1280;

NMR spectrum: (100 MHz, CDC13) δ (ppm) 8.72 (2H, s), 7.48 (2H, s), 4.70 (2H, s), 3.80 (2H, s);

| | Elementary Analysis: | | |
|---|---|---|---|
| | C | H | N |
| Calculated: | 45.96 | 3.86 | 29.78 |
| Found: | 45.68 | 3.64 | 29.99 (%) |
| | ($C_9H_9N_5O_3$) | | |

Example 1)-42

Preparation of N-cyano-N'-(3-nitroxypropyl)-4-pyridinecarboximidamide (method i)

Isopropyl N-cyano-4-pyridinecarboximidate (0.50 g, 2.6 mmol) was dissolved in methanol (10 ml), and 3-nitroxypropylamine nitrate (0.53 g, 2.9 mmol) and sodium methoxide (0.22 g, 4.1 mmol) were added. The mixture was stirred at room temperature for 18 hours. After the reaction was completed, the reaction solution was concentrated under reduced pressure. The residual concentrate was extracted with chloroform (50 ml×3). The chloroform layer was washed with water (100 ml), dried over anhydrous sodium sulfate and concentrated under reduced pressure. The residual concentrate was subjected to chromatography on a silica gel column (WAKO GEL C-200, 50 g) eluting with chloroform-methanol (60:1). The eluted fractions were concentrated under reduced pressure and crystallized from methanol-diethyl ether to give the title compound (0.27 g, 1.08 mmol, yield: 41%) as colorless crystals.

Physico-chemical properties of N-cyano-N'-(3-nitroxypropyl)-4-pyridinecarboximidamide

MP: 112.5°–112.8° C.;

IR spectrum: ($cm^{-1}$, KBr) 2180, 1600, 1280;

NMR spectrum: (500 MHz, $CDCl_3$—$CD_3OD$) δ (ppm) 8.75 (2H, dd, J=1.6, 4.4Hz), 7.54 (2H, dd, J=1.6, 4.4Hz), 4.57 (2H, t, J=6.0Hz), 3.59 (2H, t, J=6.0Hz), 2.13 (2H, quint, J=6.0Hz);

| | Elementary Analysis: | | |
|---|---|---|---|
| | C | H | N |
| Calculated: | 48.19 | 4.45 | 28.10 |
| Found: | 48.01 | 4.33 | 27.91 (%) |
| | ($C_{10}H_{11}N_5O_3$) | | |

Example 1)-43

Preparation of N cyano-N'-phenyl-4-pyridinecarboximidamide (method i)

Isopropyl N-cyano-4-pyridinecarboximidate (0.50 g, 2.6 mmol) was dissolved in methanol (5 ml), and aniline (0.27 g, 2.9 mmol) dissolved in methanol (5 ml) was added. The mixture was stirred at room temperature for 20 minutes. After the reaction was completed, the reaction solution was concentrated under reduced pressure. The residual concentrate was subjected to chromatography on a silica gel column (WAKO GEL C-200, 40 g). Elution with chloroform-methanol (100:1) gave the object compound, which was further crystallized from methanol-diethyl ether to give N-cyano-N'-phenyl-4-pyridinecarboximidamide (0.32 g, 1.4 mmol, yield: 54%) as colorless needles.

Physico-chemical properties of N-cyano-N'-phenyl-4-pyridinecarboximidamide

MP: 220°-222° C.;

IR spectrum: (cm$^{-1}$, KBr) 3060, 2180, 1610, 1580, 1530, 1450;

NMR spectrum: (100 MHz, $CDCl_3$—$CD_3OD$) δ (ppm) 8.80 (2H, brs), 7.8-7.5 (4H, m), 7.42 (2H, brs), 7.27 (1H, brs);

| | Elementary Analysis: C | H | N |
|---|---|---|---|
| Calculated: | 70.26 | 4.54 | 25.21 |
| Found: | 70.50 | 4.54 | 25.14 (%) |
| | ($C_{13}H_{10}N_4$) | | |

Example 1)-44

Preparation of N-cyano-N'-(3,4-dichlorobenzyl)-4-pyridinecarboximidamide (method i)

Isopropyl N-cyano-4-pyridinecarboximidate (0.50 g, 2.6 mmol) was dissolved in methanol (10 ml), and 3,4-dichlorobenzylamine (0.52 g, 3.0 mmol) was added. The mixture was stirred at room temperature for 3 hours. After the reaction was completed, the reaction solution was concentrated under reduced pressure. The residual concentrate was crystallized from methanol-diethyl ether to give the title compound (0.42 g, 1.4 mmol, yield: 52%) as colorless crystals.

Physico-chemical properties of N-cyano-N'-(3,4-dichlorobenzyl)-4-pyridinecarboximidamide

MP: 164.8°-165.2° C.;

IR spectrum: (cm$^{-1}$, KBr) 2190, 1590;

NMR spectrum: (500 MHz, $CDCl_3$—$CD_3OD$) δ (ppm) 8.74 (2H, dd, J=1.8, 5.8Hz), 7.52 (2H, dd, J=1.8, 5.8Hz), 7.46 (1H, d, J=2.2Hz), 7.45 (1H, d, J=8.2Hz), 7.23 (1H, dd, J=2.2, 8.2Hz), 4.59 (2H, s);

| | Elementary Analysis: C | H | N |
|---|---|---|---|
| Calculated: | 55.10 | 3.30 | 18.36 |
| Found: | 55.02 | 3.19 | 18.23 (%) |
| | ($C_{14}H_{10}N_4Cl_2$) | | |

Example 1)-45

Preparation of N-cyano-N'-(4-methylthiobenzyl)-4-pyridinecarboximidamide (method i)

Isopropyl N-cyano 4-pyridinecarboximidate (0.40 g, 2.1 mmol) was dissolved in methanol (15 ml), and 4-methylthiobenzylamine hydrochloride (0.60 g, 3.2 mmol) and triethylamine (0.43 g, 4.2 mmol) were added. The mixture was stirred at room temperature for 1 hour. After the reaction was completed, the reaction solution was then concentrated under reduced pressure. The residual concentrate was extracted with ethyl acetate (50 ml×3). The ethyl acetate layer was washed with water (100 ml), dried over anhydrous sodium sulfate and concentrated under reduced pressure. The residual concentrate was crystallized from methanol-diethyl ether to give the title compound (0.29 g, 1.0 mmol, yield: 49%) as colorless crystals.

Physico-chemical properties of N-cyano N'-(4-methylthiobenzyl)-4-pyridinecarboximidamide

MP: 165.5°-166.8° C.;

IR spectrum: (cm$^{-1}$, KBr) 2180, 1580;

NMR spectrum: (500 MHz, $CDCl_3$—$CD_3OD$) δ (ppm) 8.72 (2H, dd, J=2.0, 4.4Hz), 7.52 (2H, dd, J=2.0, 4.4Hz), 7.30 (2H, d, J=8.2Hz), 7.26 (2H, d, J=8.2Hz), 4.59 (2H, s), 2.50 (3H, s);

| | Elementary Analysis: C | H | N |
|---|---|---|---|
| Calculated: | 63.81 | 5.00 | 19.84 |
| Found: | 63.69 | 5.19 | 19.66 (%) |
| | ($C_{15}H_{14}N_4S$) | | |

Example 1)-46

Preparation of N-cyano-N'-(3-benzyloxybenzyl)-4-pyridinecarboximidamide (method i)

Isopropyl N-cyano-4-pyridinecarboximidate (0.30 g, 1.6 mmol) was dissolved in methanol (10 ml), and 3-benzyloxybenzylamine (0.42 g, 2.0 mmol) was added. The mixture was stirred at room temperature for 2 hours. After the reaction was completed, the reaction solution was then concentrated under reduced pressure. The residual concentrate was crystallized from methanol-diethyl ether to give the title compound (0.26 g, 0.8 mmol, yield: 48%) as colorless crystals.

Physico-chemical properties of N-cyano-N'-(3-benzyloxybenzyl)-4-pyridinecarboximidamide

MP: 123.8°-124.0° C.;

IR spectrum: (cm$^{-1}$, KBr) 2190, 1580;

NMR spectrum: (500 MHz, CDC13) δ (ppm) 8.69 (2H, dd, J=1.4, 5.0Hz), 7.50-7.25 (8H), 7.00-6.90 (3H), 6.80 (1H, brs), 5.09 (2H, s), 4.60 (2H, d, J=6.0Hz);

| | Elementary Analysis: C | H | N |
|---|---|---|---|
| Calculated: | 73.67 | 5.30 | 16.36 |
| Found: | 73.55 | 5.40 | 16.31 (%) |
| | ($C_{21}H_{18}N_4O$) | | |

Example 1)-47

Preparation of N-cyano-N'-[2-(4-chlorophenyl)ethyl]-4-pyridinecarboximidamide (method i)

Isopropyl N-cyano-4-pyridinecarboximidate (0.5 g, 2.6 mmol) was dissolved in methanol (5 ml), and 2-(4 chlorophenyl)ethylamine (0.46 g, 3.0 mmol) having been diluted with methanol (5 ml) was added. The mixture was stirred at room temperature for 40 minutes. After the reaction was completed, the reaction solution was then concentrated under reduced pressure. The residual concentrate was further crystallized from methanol-diethyl ether to give the title compound (0.44 g, 1.5 mmol, yield: 58%) as colorless needles.

Physico-chemical properties of N-cyano-N'-[2-(4-chlorophenyl)ethyl]-4-pyridinecarboximidamide

MP: 164.0°-165.2° C.;

IR spectrum: (cm$^{-1}$, KBr) 2180, 1590, 1540, 1500;

NMR spectrum: (100 MHz, $CDCl_3$) δ (ppm) 8.68 (2H, m), 7.4-7.1 (6H), 6.56 (1H, brs), 3.74 (2H, q, J=6.8Hz), 2.97 (2H, t, J=6.8Hz)

| | Elementary Analysis: | | |
|---|---|---|---|
| | C | H | N |
| Calculated: | 63.27 | 4.60 | 19.68 |
| Found: | 63.02 | 4.66 | 19.56 (%) |
| | ($C_{15}H_{13}N_4Cl$) | | |

Example 1) 48

Preparation of N-cyano-N'-[2-(2-methoxyphenyl)ethyl]-4-pyridinecarboximidamide (method i)

Isopropyl N-cyano-4-pyridinecarboximidate (0.50 g, 2.6 mmol) was dissolved in methanol (10 ml), and 2-(2-methoxyphenyl)ethylamine (0.44 g, 2.9 mmol) was added. The mixture was stirred at room temperature for 1 hour. After the reaction was completed, the reaction solution was concentrated under reduced pressure. The residual concentrate was subjected to chromatography on a silica gel column (WAKO GEL C-200, 40 g) eluting with chloroform-methanol (100:1). The eluted fractions were concentrated under reduced pressure and crystallized from chloroform-diethyl ether to give the title compound (0.45 g, 1.6 mmol, yield: 61%) as colorless crystals.

Physico-chemical properties of N-cyano-N'-[2-(2-methoxyphenyl)ethyl]-4-pyridinecarboximidamide

MP: 141.2°-141.5° C.;

IR spectrum: ($cm^{-1}$, KBr) 2190, 1580;

NMR spectrum: (500 MHz, CDC13) δ (ppm) 8.78 (2H, d, J=5.4Hz), 7.39 (2H, d, J=5.4Hz), 7.28 (1H, t, J=7.1Hz), 7.18 (1H, d, J=7.1Hz), 6.97 (1H, t, J=7.1Hz), 6.91 (1H, d, J=7.1Hz), 6.66 (1H, brs), 3.80 (3H, s), 3.72 (2H, m), 3.01 (2H, t, J=7.1Hz);

| | Elementary Analysis: | | |
|---|---|---|---|
| | C | H | N |
| Calculated: | 68.55 | 5.75 | 19.99 |
| Found: | 68.46 | 5.49 | 19.71 (%) |
| | ($C_{16}H_{16}N_4O$) | | |

Example 1)-49

Preparation of N-cyano-N'-(2-phenylthioethyl)-4-pyridinecarboximidamide (method i)

Isopropyl N-cyano-4-pyridinecarboximidate (0.50 g, 2.6 mmol) was dissolved in methanol (5 ml), and 2-phenylthioethylamine (0.49 g, 3.2 mmol) was added. The mixture was stirred at room temperature for 2 hours. After the reaction was completed, the reaction solution was concentrated under reduced pressure, and the residual concentrate was subjected to chromatography on a silica gel column (WAKO GEL C-200, 10 g) eluting with chloroform-methanol (50:1). The eluted fractions were concentrated under reduced pressure and crystallized from diethyl ether to give the title compound (0.49 g, 1.7

Physico-chemical properties of N-cyano-N'-(2-phenylthioethyl)-4-pyridinecarboximidamide

MP: 114.0°-114.3° C.;

IR spectrum: ($cm^{-1}$, KBr) 2190, 1590;

NMR spectrum: (500 MHz, CDC13) δ (ppm) 8.73 (2H, dd, J=1.5, 4.6Hz), 7.42-7.23 (8H), 3.71 (2H, t, J=6.2Hz), 3.23 (2H, t, J=6.2Hz)

| | Elementary Analysis: | | |
|---|---|---|---|
| | C | H | N |
| Calculated: | 63.81 | 5.00 | 19.84 |
| Found: | 63.80 | 4.89 | 19.71 (%) |
| | ($C_{15}H_{14}N_4S$) | | |

Example 1)-50

Preparation of N-cyano-N'-[2-(4-nitrophenyl) 2-nitroxyethyl]-4-pyridinecarboximidamide (method i)

Isopropyl N-cyano-4-pyridinecarboximidate (0.22 g, 1.2 mmol) was dissolved in methanol (10 ml), and 2-(4-nitrophenyl)-2-nitroxyethylamine nitrate (0.40 g, 1.4 mmol) and sodium methoxide (0.14 g, 2.6 mmol) were added. The mixture was stirred at room temperature for 16 hours. After the reaction was completed, the reaction solution was concentrated under reduced pressure, and the residue was extracted with chloroform (50 ml×3). The chloroform layer was washed with water (100 ml), dried over anhydrous sodium sulfate and concentrated under reduced pressure. The residual concentrate thus obtained was subjected to chromatography on a silica gel column (WAKO GEL C-200, 30 g) eluting with chloroform-methanol (50:1). The eluted fractions were concentrated under reduced pressure and crystallized from methanol-diethyl ether to give the title compound (0.13 g, 0.4 mmol, yield: 31%) as colorless crystals.

Physico-chemical properties of N-cyano-N'-[2-(4-nitrophenyl)-2-nitroxyethyl]-4-pyridinecarboximidamide

MP: 127.5°-129.0° C.;

IR spectrum: ($cm^{-1}$, KBr) 2190, 1640, 1590, 1530, 1350;

NMR spectrum: (500 MHz, $CDCl_3$—$CD_3OD$) δ (ppm) 8.78 (2H, d, J=4.4Hz), 8.33 (2H, d, J=8.4Hz), 7.68 (2H, d, J=8.4Hz), 7.52 (2H, d, J=4.4Hz), 6.31 (1H, dd, J=3.8, 9.4Hz), 3.80 (2H, m);

| | Elementary Analysis: | | |
|---|---|---|---|
| | C | H | N |
| Calculated: | 50.57 | 3.39 | 23.59 |
| Found: | 50.46 | 3.58 | 23.36 (%) |
| | ($C_{15}H_{12}N_6O_5$) | | |

Example 1)-51

Preparation of N-cyano-N'-[1-methyl-2-(4-nitrophenyl)-2-nitroxyethyl]-4-pyridinecarboximidamide (method i)

Isopropyl N-cyano-4-pyridinecarboximidate (0.31 g, 1.6 mmol) was dissolved in methanol (15 ml), and 1-methyl-2-(4-nitrophenyl)-2-nitroxyethylamine nitrate (0.50 g, 1.8 mmol) and sodium methoxide (0.09 g, 1.7 mmol) were added. The mixture was stirred at room temperature for 16 hours. After the reaction was completed, the reaction solution was concentrated under reduced pressure, and the residue was extracted with chloroform (50 ml×3). The chloroform layer was washed with water (100 ml), dried over anhydrous sodium sulfate and concentrated under reduced pressure. The residue thus obtained was subjected to chromatography on a silica gel column (WAKO GEL C-200, 30 g) eluting with chloroform-methanol (60:1). The eluted fractions were concentrated under reduced pressure and crystallized from diethyl ether to give the title compound (0.03 g, 0.08 mmol, yield: 5%) as colorless crystals.

Physico-chemical properties of N-cyano-N'-[1-methyl-2-(4-nitrophenyl)-2-nitroxyethyl]-4-pyridinecarboximidamide

MP: 153.0°-153.1° C.;

IR spectrum: ($cm^{-1}$, KBr) 2200, 1650, 1580, 1530, 1350, 1290;

NMR spectrum: (500 MHz, $CDCl_3$—$CD_3OD$) δ (ppm) 8.77 (2H, d, J=5.9Hz), 8.35 (2H, d, J=8.9Hz), 7.69 (2H, d, J=8.9Hz), 7.49 (2H, d, J=5.9Hz), 1.32 (3H, d, J=9.4Hz);

| | Elementary Analysis: C | H | N |
|---|---|---|---|
| Calculated: | 51.89 | 3.80 | 22.69 |
| Found: | 51.62 | 3.99 | 22.57 (%) |
| | ($C_{16}H_{14}N_6O_5$) | | |

Example 1)-52

Preparation of N-cyano-N'-(2-nitroxyethyl)-3-(6-chloropyridine)carboximidamide (method i)

a) 6-chloro-3-cyanopyridine (3.63 g, 26.2 mmol) was suspended in isopropanol (40 ml), and sodium hydride (0.1 g, 4.2 mmol) from which oily matters had been removed by washing with ether was added. The mixture was stirred at room temperature for 18 hours. After the reaction was completed, the reaction solution was neutralized by adding acetic acid (0.27 g, 4.5 mmol) and then concentrated under reduced pressure. The residual concentrate was diluted with ether (100 ml), and ether insolubles were removed by filtration. The filtrate was concentrated under reduced pressure. The residual concentrate was diluted with hexane (100 ml), and the deposited unreacted 6-chloro-3-cyanopyridine was removed by filtration. The filtrate was concentrated under reduced pressure to give the crude product of isopropyl 3-(6-chloropyridine)carboximidate (1.88 g) as colorless oil. Next, to this oil were added cyanamide (0.80 g, 19.0 mmol) and a phosphate buffer (pH 5.4, 60 ml) of $Na_2HPO_4$ (1.34 g, 9.4 mmol) and $NaH_2PO_4.2H_2O$ (5.90 g, 37.8 mmol), and the mixture was stirred at room temperature for 24 hours. After the reaction was completed, the reaction solution was extracted with dichloromethane (100 ml×4), and the dichloromethane layer was dried over anhydrous sodium sulfate and concentrated under reduced pressure. The residue thus obtained was subjected to chromatography on a silica gel column (WAKO GEL C-200, 70 g, eluting with hexane-dichloromethane-methanol (50:50:1). The eluted fractions were concentrated under reduced pressure to give isopropyl N-cyano-3-(6-chloropyridine)carboximidate (0.83 g, 3.7 mmol, yield: 14%) as colorless syrup.

Physico-chemical properties of isopropyl N-cyano-3-(6-chloropyridine)carboximidate IR spectrum: ($cm^{-1}$, neat) 2200, 1610, 1580, 1310, 1110;

NMR spectrum: (100 MHz, $CDCl_3$—$CD_3OD$) δ (ppm) 9.13 (1H, d, J=3.0Hz), 8.61 (1H, dd, J=3.0, 8.6Hz), 7.52 (1H, d, J=8.6Hz), 5.43 (1H, m, J=6.1Hz), 1.49 (6H, d, J=6.1Hz).

b) Isopropyl N-cyano-3-(6 -chloropyridine)carboximidate (0.20 g, 0.9 mmol) was dissolved in methanol (8 ml), and 2-nitroxyethylamine nitrate (0.23 g, 1.4 mmol) and sodium methoxide (0.1 g, 1.9 mmol) were added. The mixture was stirred at room temperature for 5 hours. After the reaction was completed, the reaction solution was concentrated under reduced pressure. The residue thus obtained was extracted with chloroform (50 ml×3). The chloroform layer was washed with water (100 ml), dried over anhydrous sodium sulfate and concentrated under reduced pressure. The residual concentrate was subjected to chromatography on a silica gel column (WAKO GEL C-200, 25 g) eluting with chloroform-methanol (50:1). The eluted fractions were concentrated under reduced pressure and crystallized from diethyl ether to give the title compound (0.04 g, 0.1 mmol, yield: 17%) as colorless crystals.

Physico-chemical properties of N-cyano-N'-(2-nitroxyethyl)-3-(6-chloropyridine)carboximidamide

MP: 139.0°-140.5° C.;

IR spectrum: ($cm^{-1}$, KBr) 2180, 1630, 1580, 1280;

NMR spectrum: (500 MHz, $CD_3OD$) δ (ppm) 8.62 (1H, d, J=3.0Hz), 8.08 (1H, dd, J=3.0, 9.1Hz), 7.65 (1H, d, J=9.1Hz), 4.75 (2H, t, J=7.1Hz), 3.86 (2H, t, J=7.1Hz);

| | Elementary Analysis: C | H | N |
|---|---|---|---|
| Calculated: | 40.09 | 2.99 | 25.97 |
| Found: | 39.95 | 2.88 | 25.69 (%) |
| | ($C_9H_8N_5O_3Cl$) | | |

Example 1)-53

Preparation of N-cyano-N'-(2-phenylethyl)-3-(6-chloropyridine)carboximidamide (method i)

Isopropyl N-cyano-3-(6-chloropyridine)carboximidate (0.30 g, 1.3 mmol) was dissolved in methanol (8 ml), and 2-phenylethylamine (0.18 g, 1.5 mmol) was added. The mixture was stirred at room temperature for 30 minutes. After the reaction was completed, the reaction solution was concentrated under reduced pressure, and the residue was crystallized from diethyl ether to give the title compound (0.24 g, 0.8 mmol, yield: 63%) as colorless crystals.

Physico-chemical properties of N-cyano-N'-(2-phenylethyl)-3-(6-chloropyridine)carboximidamide

MP: 168.8°-169.0° C.;

IR spectrum: ($cm^{-1}$, KBr) 2180, 1590;

NMR spectrum: (500 MHz, $CD_3OD$) δ (ppm) 8.47 (1H, d, J=3.0Hz), 7.96 (1H, dd, J=3.0, 9.3Hz), 7.61 (1H, d, J=9.3Hz), 7.36-7.20 (5H), 3.72 (2H, t, J=7.2Hz), 2.99 (2H, t, J=7.2Hz)

| | Elementary Analysis: C | H | N |
|---|---|---|---|
| Calculated: | 63.27 | 4.60 | 19.68 |
| Found: | 63.25 | 4.38 | 19.37 (%) |
| | ($C_{15}H_{13}N_4Cl$) | | |

Example 1) 54

Preparation of N-cyano-N'-benzyl-3 -pyridinecarboximidamide (method ii)

a) N-benzylnicotinamide (1.0 g, 4.7 mmol) was dissolved in toluene (90 ml). Lawesson's reagent (2.3 g, 5.7 mmol) was added, and the mixture was heated under reflux in argon stream for 3 hours. After the reaction was completed, the reaction mixture was cooled to room temperature and concentrated under reduced pressure. The concentrate thus obtained was extracted with a 2N aqueous hydrochloric acid solution (200 ml×3), and the aqueous layer was washed with chloroform (500 ml). After washing, the aqueous hydrochloric acid layer was neutralized with NaOH and extracted with chloroform (200 ml×3). The chloroform layer was dried over anhydrous sodium sulfate and concentrated under reduced pressure. The concentrate was further crystallized from chloroform-hexane to give N-benzylnicotinethioamide (0.83 g, 3.6 mmol, yield: 77%) as pale yellow needles.

Physico-chemical properties of N-benzylnicotinethioamide

MP: 136.0°-136.5° C.;

IR spectrum: ($cm^{-1}$, KBr) 3170, 1540, 1420, 1390, 1340, 760, 700;

NMR spectrum: (100 MHz, CDC13) δ (ppm) 8.81 (1H, brs), 8.57 (1H, d, J=4.1Hz), 8.14 (1H, dt, J=2.7, 10.0Hz), 8.00 (1H, brs), 7.40 (5H, s), 7.35 (1H, m), 5.00 (2H, d, J=6.2Hz);

b) N-benzylnicotinethioamide (0.5 g, 2.2 mmol) was dissolved in acetonitrile (20 ml), and phosphorus oxychloride (0.4 g, 2.6 mmol) was added. The mixture was stirred at room temperature for 9 hours. Cyanamide (0.92 g, 21.9 mmol) and triethylamine (0.27 g, 2.6 mmol) were added, and the mixture was heated under reflux in argon stream for 4 hours. After the reaction was completed, the reaction solution was concentrated under reduced pressure. Chloroform (50 ml) was added to the residual concentrate, and insolubles were removed by filtration. The filtrate was concentrated under reduced pressure. The concentrate thus obtained was subjected to chromatography on a silica gel column (WAKO GEL C-200, 30 g). Elution with chloroform-methanol (100:1) gave the title compound, which was further crystallized from methanol-diethyl ether to give N-cyano-N'-benzyl-3-pyridinecarboximidamide (0.085 g, 0.3 mmol, yield: 16%) as colorless needles.

Physico-chemical properties including mp, IR spectrum and

NMR spectrum of the crystal thus obtained well accorded with those obtained in

Example 1)-17.

Example 1)-55

| (Tablet/formulation in one tablet) | |
|---|---|
| Compound of the present invention | 2 mg |
| Lactose | 75.5 |
| Corn starch | 18 |
| Talc | 4 |
| Magnesium stearate | 0.5 |
| Total | 100 mg |

Components set forth above are blended and pressed into a tablet.

Example 1)-56

| (Capsule/formulation in one capsule) | |
|---|---|
| Compound of the present invention | 5 mg |
| Lactose | 94 |
| Magnesium stearate | 1 |
| Total | 100 mg |

Components set forth above are blended and pressed into a capsule.

Example 1)-57

| (Injection/formulation in one vial) | |
|---|---|
| Compound of the present invention | 1 mg |
| Maltose | 25 mg |
| Distilled water for injection | q.v. |
| Total | 2 mg |

Components set forth above are blended, filtrated and then charged into a vial. They are lyophilized in a usual manner and stoppered to make an injection.

2) Compounds Represented by the Formula (I')

Referential Example 2)-1

Vasorelaxing effect on the isolated rat aortae (1) Method

The compounds of the present invention were tested for their physiological activities by measuring the tension of isolated rat aortae isometrically.

Thoracic aortae obtained from male Wistar rats (weighing 250-350 g) were cut into ring segments about 3 mm long. The ring preparation was placed in an organ bath filled with 10 ml of Krebs-Ringer solution which was maintained at 37° C. and gassed with 95% $O_2$-5% $CO_2$.

The preparation in the organ bath was allowed to equilibrate under resting tension 1 g. After equilibration period, the solution in the organ bath was replaced with an isotonic solution containing 40 mM KCl to contract the preparation.

After the contraction induced by KCl had reached plateau, the concentration-response relationship for the test compound was determined by means of cumulative addition.

The relaxation response of the test compounds was expressed as the percent inhibition of the contraction induced by KCl, and the $IC_{50}$ value, which is a concentration required for inhibiting the contraction induced by KCl to an extent of 50%, was calculated by the Probit method from the concentration-response curve.

(2) Results

The $IC_{50}$ values of the test compounds are shown in the following table.

| Test Compound No. | $IC_{50}$ Value (M) |
|---|---|
| (59) | $2.4 \times 10^{-5}$ |
| (60) | $6.1 \times 10^{-6}$ |
| (61) | $5.3 \times 10^{-5}$ |
| (62) | $2.6 \times 10^{-5}$ |
| (63) | $1.8 \times 10^{-5}$ |
| (64) | $8.0 \times 10^{-6}$ |
| (65) | $9.4 \times 10^{-5}$ |
| (66) | $9.6 \times 10^{-6}$ |
| (67) | $1.9 \times 10^{-5}$ |
| (68) | $9.2 \times 10^{-5}$ |
| (69) | $4.0 \times 10^{-5}$ |
| (70) | $4.3 \times 10^{-6}$ |

Referential Example 2)-2

Hypotensive effect on spontaneous hypertensive rats (intravenously)

(1) Method

The hypotensive effects of the compounds of the present invention [test compounds: N-cyano-N'-(2-nitroxyethyl)-2-furancarboximidamide (compound (62)) and N-cyano-N'-(2-nitroxyethyl)-2-thiophenecarboximidamide (compound (66))] were observed in male spontaneous hypertensive rates (SHR).

Rats were anesthetized with urethane-α-chloralose (1 g/kg–25 mg/kg; intraperitoneally). Mean blood pressure was measured by a pressure transducer through a cannula inserted into the carotid artery. The compound was cumulatively administered every 30 minutes through the canulla inserted into the jagular vein. The change in blood pressure was expressed as percent of the blood pressure before the administration of the compound. And the $ED_{20}$ value, which was the dose required for decreasing blood pressure to an extent of 20%, was calculated from the dose-response curve.

(2) Results

The $ED_{20}$ values of the test compounds are shown in the following table.

| Compound No. | $ED_{20}$ (mg/kg, i.v.) |
|---|---|
| (62) | 0.025 |
| (66) | 0.115 |

i.v.: intravenously.

Example 2)-1

Preparation of N-cyano-N'-(2-nitroxyethyl)-3-quinolinecarboximidamide a) 3-cyanoquinoline (1.58 g, 10.2 mmol) was dissolved in methanol (20 ml), and sodium methoxide (0.06 g, 1.1 mmol) was added. The reaction was conducted at room temperature for 22 hours. After the reaction was completed, acetic acid (0.07 g, 1.1 mmol) was added to neutralize the reaction solution, and the solution was concentrated under reduced pressure. Diethyl ether (60 ml) was added to the concentrated residue, and insolubles were removed by filtration. The filtrate was concentrated under reduced pressure to give the crude product of methyl 3-quinolinecarboximidate.

Next, cyanamide (0.84 g, 20 mmol) and a phosphate buffer (pH 5.4, 10 ml) of $Na_2HPO_4$ (1.42 g, 10 mmol) and $NaH_2PO_4.2H_2O$ (6.24 g, 40 mmol) were added, and the mixture was stirred at room temperature for 6 hours. After reaction was completed, insolubles in the reaction mixture were removed by filtration, and the filtrate was extracted with dichloromethane (50 ml×3), and the dichloromethane layer was washed with saturated saline, dried over anhydrous sodium sulfate and then concentrated under reduced pressure. The residue thus obtained was subjected to chromatography on a silica gel column (WAKO GEL C-200, 25 g) eluting with dichloromethane-hexane (3:2). The eluted fractions were concentrated under reduced pressure, crystallized from diethyl ether to give methyl N-cyano-3-quinolinecarboximidate (1.14 g, 5.4 mmol, yield: 53%) as pale brown crystals.

Physico-chemical properties of methyl N-cyano-3-quinolinecarboximidate

MP: 113.5°–113.8° C.;

IR spectrum: ($cm^{-1}$, KBr) 2190, 1610, 1310;

NMR spectrum: (500 MHz, CDC13) δ (ppm) 9.35 (1H, d, J=2.6Hz), 9.17 (1H, d, J=2.6Hz), 8.17 (1H, d, J=8.0Hz), 8.00 (1H, d, J=8.0Hz), 7.90 (1H, dt, J=1.8, 8.0Hz), 7.68 (1H, t, J=8.0Hz), 4.18 (3H, s);

| | Elementary Analysis: C | H | N |
|---|---|---|---|
| Calculated: | 68.24 | 4.29 | 19.89 |
| Found: | 68.01 | 4.23 | 19.67 (%) |
| | ($C_{12}H_9N_3O$) | | |

b) Methyl N-cyano-3-quinolinecarboximidate (0.32 g, 1.5 mmol) was dissolved in methanol (3 ml), 2-nitroxyethylamine nitrate (0.42 g, 2.5 mmol) and sodium methoxide (0.12 g, 2.2 mmol) were added. The mixture was stirred at room temperature for 18 hours. After the reaction was completed, the reaction solution was concentrated under reduced pressure, and the residue thus obtained was subjected to chromatography on a silica gel column (WAKO GEL C-200, 30 g) eluting with dichloromethane-methanol (50:1). The eluted fractions were concentrated under reduced pressure and crystallized from dichloromethane-diethyl ether to give the title compound (0.23 g, 0.80 mmol, yield: 54%) as colorless crystals.

Physico-chemical properties of N-cyano-N'-(2-nitroxyethyl)-3-quinolinecarboximidamide

MP: 126.5°–127.0° C.;

IR spectrum: ($cm^{-1}$, KBr) 2190, 1620, 1580, 1560, 1280;

NMR spectrum: (500 MHz, $CD_3OD$) δ (ppm) 9.05 (1H, s), 8.71 (1H, s), 8.13 (1H, d, J=8.0Hz), 8.10 (1H, d, J=8.0Hz), 7.93 (1H, t, J=7.7Hz), 7.74 (1H, t, J=7.7Hz), 4.80 (2H, t, J=5.7Hz), 3.92 (2H, t, J=5.7Hz);

| | Elementary Analysis: C | H | N |
|---|---|---|---|
| Calculated: | 54.74 | 2.46 | 24.55 |
| Found: | 54.66 | 2.34 | 24.29 (%) |
| | ($C_{13}H_{11}N_5O_3$) | | |

Example 2)-2

Preparation of N-cyano-N'-(2-phenylethyl)-3-quinoline-carboximidamide

Methyl N-cyano-3-quinolinecarboximidate (0.32 g, 1.5 mmol) was dissolved in methanol (3 ml), 2-phenylethylamine (0.20 g, 1.65 mmol) was added. The mixture was stirred at room temperature for 30 minutes. After the reaction was completed, the reaction solution was concentrated under reduced pressure, and the residue thus obtained was crystallized from diethyl ether to give the title compound (0.41 g, 1.36 mmol, yield: 91%) as pale yellow crystals.

Physico-chemical properties of N-cyano-N'-(2-phenylethyl)-3-quinolinecarboximidamide

MP: 165.0°–167.0° C.;

IR spectrum: ($cm^{-1}$, KBr) 2190, 1580, 1560;

NMR spectrum: (500 MHz, $CDCl_3$) δ (ppm) 8.84 (1H, s), 8.47 (1H, s), 8.11 (1H, d, J=8.5Hz), 7.90 (1H, d, J=8.6Hz), 7.84 (1H, t, J=7.3Hz), 7.65 (1H, t, J=8.0Hz), 7.37 (2H, t, J=7.3Hz), 7.32–7.25 (3H), 6.05 (1H, brs), 3.87 (2H, dd, J=6.7, 12.8Hz), 3.06 (2H, t, J=6.7Hz);

| | Elementary Analysis: C | H | N |
|---|---|---|---|
| Calculated: | 75.98 | 5.37 | 18.65 |
| Found: | 75.86 | 5.32 | 18.42 (%) |
| | ($C_{19}H_{16}N_4$) | | |

Example 2)-3

Preparation of N-cyano-N'-(2-nitroxyethyl)pyrazinecarboximidamide a) Cyanopyrazine (5.26 g, 50 mmol) was dissolved in methanol (40 ml), and sodium methoxide (0.27 g, 5.0 mmol) was added. The reaction mixture was stirred at room temperature for 45 minutes. After the reaction was completed, acetic acid (0.33 g, 5.5 mmol) was added to neutralize the reaction solution, and the solution was concentrated under reduced pressure. Dichloromethane (50 ml) and diethyl ether (50 ml) were added to the concentrated residue, and insolubles were removed by filtration. The filtrate was concentrated under reduced pressure to give the crude product of methyl pyrazinecarboximidate (6.87 g) as colorless powder.

Next, cyanamide (3.15 g, 75 mmol) and a phosphate buffer (pH 5.4, 40 ml) of $Na_2HPO_4$ (7.10 g, 50 mmol) and $NaHzPO_4.2H_2O$ (31.22 g, 200 mmol) were added, and the mixture was stirred at room temperature for 48 hours. After the reaction was completed, the reaction solution was extracted with dichloromethane (100 ml×4), and the dichloromethane layer was washed with saturated saline (300 ml), dried over anhydrous sodium sulfate and then concentrated under reduced pressure. The residue thus obtained was crystallized from diethyl ether to give methyl N-cyanopyrazinecarboximidate (4.53 g, 27.9 mmol, yield: 56%) as colorless crystals.

Physico-chemical properties of methyl N-cyanopyrazinecarboximidate

MP: 47.5°–49.0° C.;

IR spectrum: ($cm^{-1}$, KBr) 2190, 1630, 1330;

NMR spectrum: (500 MHz, CDC13) δ (ppm) 9.33 (1H, s), 8.78 (1H, d, J=2.2Hz), 8.74 (1H, brs), 4.07 (3H, s);

| | Elementary Analysis: C | H | N |
|---|---|---|---|
| Calculated: | 51.85 | 3.73 | 34.55 |
| Found: | 51.71 | 3.69 | 34.29 (%) |
| | ($C_7H_6N_4O$) | | |

b) Methyl N-cyanopyrazinecarboximidate (0.49 g, 3.0 mmol) was dissolved in methanol (6 ml), 2-nitroxyethylamine nitrate (1.01 g, 6.0 mmol) and triethylamine (1.01 g, 10.0 mmol) were added. The mixture was stirred at room temperature for 46 hours. After the reaction was completed, the reaction solution was concentrated under reduced pressure, and the residue thus obtained was subjected to chromatography on a silica gel column (WAKO GEL C 200, 30 g) eluting with chloroform-methanol (300:1). The eluted fractions were concentrated under reduced pressure and crystallized from diethyl ether to give the title compound (0.18 g, 0.78 mmol, yield: 26%) as colorless crystals.

Physico-chemical properties of N-cyano-N'-(2-nitroxyethyl)pyrazinecarboximidamide

MP: 102.8°–103.0° C.;

IR spectrum: ($cm^{-1}$, KBr) 2180, 1630, 1620, 1290;

NMR spectrum: (500 MHz, $CDCl_3$) δ (ppm) 9.83 (1H, brs), 8.88 (1H, s), 8.64 (1H, s), 8.28 (1H, brs), 4.78 (2H, t, J=4.9Hz), 4.15 (2H, brs);

| | Elementary Analysis: C | H | N |
|---|---|---|---|
| Calculated: | 40.68 | 3.41 | 35.58 |
| Found: | 40.66 | 3.27 | 35.30 (%) |
| | ($C_8H_8N_6O_3$) | | |

Example 2)-4

Preparation of N-cyano-N'-(2-nitroxyethyl)-2-furancarboximidamide a) 2-Cyanofuran (4.50 g, 48.3 mmol) was dissolved in methanol (25 ml), and sodium methoxide (130 mg, 2.4 mmol) was added under ice-cooling. The mixture was stirred while the temperature is slowly raised up to room temperature for 2 hours. After the reaction was completed, acetic acid (0.16 g, 2.6 mmol) was added to neutralize the reaction solution, and the solution was concentrated under reduced pressure. Diethyl ether (100 ml) was added to the concentrated residue, and insolubles were removed by filtration. The filtrate was concentrated under reduced pressure to give the crude product of methyl 2-furancarboximidate (6.0 g) as a pale yellow oil.

Next, cyanamide (4.06 g, 96.6 mmol) and a phosphate buffer (pH 6.0, 30 ml) of $Na_2HPO_4$ (6.86 g, 48.3 mmol) and $NaH_2PO_4.2H_2O$ (15.08 g, 96.6 mmol) were added, and the mixture was stirred at room temperature for 24 hours. After the reaction was completed, the reaction solution was extracted with dichloromethane (70 ml×4), and the dichloromethane layer was dried over anhydrous sodium sulfate and then concentrated under reduced pressure. The residue thus obtained was crystallized from diisopropyl ether-hexane to give methyl N-cyano-2-furancarboximidate (4.83 g, 32.2 mmol, yield: 67%) as colorless crystals.

Physico-chemical properties of methyl N-cyano-2-furancarboximidate

MP: 58.5°–59.2° C.;

IR spectrum: ($cm^{-1}$, KBr) 2200, 1600, 1480, 1350;

NMR spectrum: (500 MHz, $CDCl_3$) δ (ppm) 7.78 (1H, d, J=3.8Hz), 7.69 (1H, d, J=1.8Hz), 6.64 (1H, dd, J=1.8, 3.8Hz), 4.05 (3H, s);

| | Elementary Analysis: C | H | N |
|---|---|---|---|
| Calculated: | 56.00 | 4.03 | 18.66 |
| Found: | 55.82 | 4.04 | 18.40 (%) |
| | ($C_7H_6N_2O_2$) | | |

b) Methyl N-cyano-2 furancarboximidate (0.32 g, 2.09 mmol) was dissolved in methanol (3 ml), 2-nitroxyethylamine nitrate (0.37 g, 2.19 mmol) and triethylamine (0.22 g, 2.19 mmol) were added. The mixture was stirred at room temperature for 16 hours. After the reaction was completed, the reaction solution was concentrated under reduced pressure, and the residue thus obtained was subjected to chromatography on a silica gel column (WAKO GEL C-200, 25 g) eluting with dichloromethane. The eluted fractions were concentrated under reduced pressure and crystallized from dichloromethane to give the title compound (0.20 g, 0.89 mmol, yield: 45%) as colorless crystals.

Physico-chemical properties of N-cyano-N'-(2-nitroxyethyl)-2-furancarboximidamide

MP: 77.0°-77.8° C.;

IR spectrum: ($cm^{-1}$, KBr) 2180, 1630, 1600, 1570;

NMR spectrum: (500 MHz, $CDCl_3$) δ (ppm) 8.04 (1H, d, J=3.7Hz), 7.57 (1H, d, J=1.2Hz), 6.79 (1H, brs), 6.66 (1H, dd, J=1.2, 3.7Hz), 4.69 (2H, t, J=5.5Hz), 3.87 (2H, dd, J=5.5Hz, 10.4Hz);

| Elementary Analysis: | C | H | N |
|---|---|---|---|
| Calculated: | 42.86 | 3.60 | 24.99 |
| Found: | 42.92 | 3.48 | 24.72 (%) |
| | ($C_8H_8N_4O_4$) | | |

Example 2)-5

Preparation of N-cyano-N'-(2-phenylethyl)-2-furancarboximidamide

Methyl N-cyano-2-furancarboximidate (0.30 g, 2.0 mmol) was dissolved in methanol (2 ml), and 2-phenylethylamine (0.27 g, 2.2 mmol) was added. The mixture was stirred at room temperature for 1 hour. After the reaction was completed, the reaction solution was concentrated under reduced pressure, and the residue thus obtained was crystallized from diethyl ether-hexane to give the title compound (0.46 g, 1.93 mmol, yield: 97%) as colorless crystals.

Physico-chemical properties of N-cyano-N'-(2-phenylethyl)-2-furancarboximidamide

MP: 88° C.;

IR spectrum: ($cm^{-1}$, KBr) 2180, 1600, 1570;

NMR spectrum: (500 MHz, $CDCl_3$) δ (ppm) 8.00 (1H, d, J=3.7Hz), 7.48 (1H, d, J=1.2Hz), 7.4-7.2 (5H), 6.61 (1H, dd, J=1.2, 3.7Hz), 6.43 (1H, brs), 3.75 (2H, dd, J=7.3, 13.4Hz), 2.96 (2H, t, J=7.3Hz);

| Elementary Analysis: | C | H | N |
|---|---|---|---|
| Calculated: | 70.28 | 5.48 | 17.56 |
| Found: | 70.12 | 5.54 | 17.41 (%) |
| | ($C_{14}H_{13}N_3O$) | | |

Example 2)-6

Preparation of N-cyano-N'-(2-nitroxyethyl)-3-furancarboximidamide a) 3-cyanofuran (3.76 g, 40.1 mmol) was dissolved in methanol (30 ml), and sodium methoxide (0.1 g, 1.9 mmol) was added. The mixture was stirred at room temperature for 18 hours. After the reaction was completed, acetic acid (0.14 g, 2.3 mmol) was added to neutralize the reaction solution, and the solution was concentrated under reduced pressure. Diethyl ether was added to the concentrated residue, and insolubles were removed by filtration. The filtrate was concentrated under reduced pressure to give the crude product of methyl 3-furancarboximidate as a pale yellow oil.

Next, cyanamide (3.37 g, 80.2 mmol) and a phosphate buffer (pH 5.4, 50 ml) of $Na_2HPO_4$ (5.69 g, 40.1 mmol) and $NaH_2PO_4.2H_2O$ (25.0 g, 160.2 mmol) were added to the oil, and the mixture was stirred at room temperature for 18 hours. After the reaction was completed, the reaction solution was extracted with chloroform (100 ml×3), and the chloroform layer was dried over anhydrous sodium sulfate and then concentrated under reduced pressure. The residue thus obtained was subjected to chromatography with chloroform. The eluted fractions were concentrated under reduced pressure to give methyl N cyano-3-furancarboximidate (1.09 g, 7.3 mmol, yield: 18%) as a colorless oil.

Physico-chemical properties of methyl N-cyano-3-furancarboximidate

IR spectrum: ($cm^{-1}$, neat) 2190, 1610, 1590;

NMR spectrum: (100 MHz, CDC13) δ (ppm) 8.59 (1H, t, J=1.1Hz), 7.57 (1H, t, J=2.2Hz), 7.06 (1H, dd, J=1.1, 2.2Hz), 4.00 (3H, s).

b) Methyl N-cyano-3-furancarboximidate (0.5 g, 3.3 mmol) was dissolved in methanol (10 ml), and 2 nitroxyethylamine nitrate (0.84 g, 5.0 mmol) and sodium methoxide (0.27 g, 5.0 mmol) were added. The mixture was stirred at room temperature for 26 hours. After the reaction was completed, the reaction solution was concentrated under reduced pressure, and the residue thus obtained was extracted with chloroform (60 ml×3). The chloroform layer was washed with water (100 ml), dried over anhydrous sodium sulfate and concentrated under reduced pressure. The residual concentrate was subjected to chromatography on a silica gel column (WAKO GEL C 200, 20 g) eluting with chloroform-methanol (100:1). The eluted fractions were concentrated under reduced pressure and crystallized from methanol-diethyl ether to give the title compound (0.06 g, 0.27 mmol, yield: 8%) as colorless crystals.

Physico-chemical properties of N-cyano-N'-(2-nitroxyethyl)-3-furancarboximidamide

MP: 107.1°-107.9° C.;

IR spectrum: ($cm^{-1}$, KBr) 2180, 1640, 1600, 1550;

NMR spectrum: (500 MHz, CDC13) δ (ppm) 8.44 (1H, s), 7.53 (1H, s), 6.83 (1H, s), 4.68 (2H, t, J=4.9Hz), 3.80 (2H, t, J=4.9Hz);

| Elementary Analysis: | C | H | N |
|---|---|---|---|
| Calculated: | 42.86 | 3.60 | 24.99 |
| Found: | 42.61 | 3.53 | 24.73 (%) |
| | ($C_8H_8N_4O_4$) | | |

Example 2)-7

Preparation of N-cyano-N'-(2-phenylethyl)-3-furancarboximidamide

Methyl N-cyano-3-furancarboximidate (0.30 g, 2.0 mmol) was dissolved in methanol (10 ml), and 2-phenylethylamine (0.27 g, 2.2 mmol) was added. The mixture was stirred at room temperature for 2 hours. After the reaction was completed, the reaction solution was concentrated under reduced pressure, and the residue thus obtained was crystallized from diethyl ether to give the title compound (0.38 g, 1.59 mmol, yield: 79%) as colorless crystals.

Physico-chemical properties of N-cyano-N'-(2-phenylethyl)-3-furancarboximidamide

MP: 132.5°-133.1° C.;

IR spectrum: ($cm^{-1}$, KBr) 2170, 1610, 1560;

NMR spectrum: (100 MHz, CDC13) δ (ppm) 8.28 (1H, s), 7.45 (1H, t, J=1.9Hz), 7.4–7.1 (5H), 6.69 (1H, s), 6.54 (1H, brs), 3.68 (2H, q, J=6.6Hz), 2.95 (2H, t, 6.6Hz);

| | Elementary Analysis: | | |
|---|---|---|---|
| | C | H | N |
| Calculated: | 70.28 | 5.48 | 17.56 |
| Found: | 70.22 | 5.41 | 17.37 (%) |
| | ($C_{14}H_{13}N_3O$) | | |

Example 2)-8

Preparation of N-cyano-N'-(2-nitroxyethyl)-2-thiophenecarboximidamide a) 2-cyanothiophene (5.46 g, 50 mmol) was dissolved in methanol (25 ml), and sodium methoxide (0.27 g, 5 mmol) was added. The mixture was stirred at room temperature for 18 hours. After the reaction was completed, acetic acid (0.33 g, 5.5 mmol) was added to neutralize the reaction solution, and the solution was concentrated under reduced pressure. Diethyl ether (40 ml) was added to the concentrated residue, and insolubles were removed by filtration. The filtrate was concentrated under reduced pressure to give the crude product of methyl 2-thiophenecarboximidate (6.35 g) as a yellow oil.

Next, cyanamide (2.52 g, 60 mmol) and a phosphate buffer (pH 6.0, 20 ml) of $Na_2HPO_4$ (4.26 g, 30 mmol) and $NaH_2PO_4.2H_2O$ (9.36 g, 60 mmol) were added to the oil, and the mixture was stirred at room temperature for 14 hours. After the reaction was completed, the reaction solution was extracted with dichloromethane (50 ml×4), and the dichloromethane layer was dried over anhydrous sodium sulfate and then concentrated under reduced pressure. The residue thus obtained was crystallized from dichloromethane-hexane to give methyl N-cyano-2-thiophenecarboximidate (4.48 g, 27.0 mmol, yield: 54%) as colorless crystals.

Physico-chemical properties of methyl N-cyano-2-thiophenecarboximidate

MP: 66.9°–67.1° C.;

IR spectrum: ($cm^{-1}$, KBr) 2200, 1580;

NMR spectrum: (500 MHz, $CDCl_3$) δ (ppm) 8.64 (1H, d, J=4.8Hz), 7.77 (1H, d 7.27 (1H, t, J=4.8Hz), 4.10 (3H, s);

| | Elementary Analysis: | | |
|---|---|---|---|
| | C | H | N |
| Calculated: | 50.59 | 3.64 | 16.86 |
| Found: | 50.46 | 3.52 | 16.61 (%) |
| | ($C_7H_6N_2OS$) | | |

b) Methyl N-cyano-2-thiophenecarboximidate (0.32 g, 1.9 mmol) was dissolved in methanol (3 ml), and 2-nitroxyethylamine nitrate (0.34 g, 2.0 mmol) and triethylamine (0.20 g, 2.0 mmol) were added. The mixture was stirred at room temperature for 17 hours. After the reaction was completed, the reaction solution was concentrated under reduced pressure, and the residue thus obtained was subjected to chromatography on a silica gel column (WAKO GEL C-200, 25 g) eluting with ethyl acetate. The eluted fractions were concentrated under reduced pressure and crystallized from ethyl acetate-hexane to give the title compound (0.18 g, 0.77 mmol, yield: 40%) as colorless crystals.

Physico-chemical properties of N-cyano-N'-(2-nitroxyethyl)-2-thiophenecarboximidamide

MP: 101.5°–102.0° C.;

IR spectrum: ($cm^{-1}$, KBr) 2180, 1630, 1570, 1280;

NMR spectrum: (500 MHz, $CDCl_3$) δ (ppm) 7.96 (1H, d, J=3.7Hz), 7.61 (1H, d, J=3.7Hz), 7.19 (1H, t, J=3.7Hz), 4.70 (2H, t, J=4.9Hz), 3.82 (2H, t, J=4.9Hz);

| | Elementary Analysis: | | |
|---|---|---|---|
| | C | H | N |
| Calculated: | 40.00 | 3.36 | 23.32 |
| Found: | 39.88 | 3.42 | 23.22 (%) |
| | ($C_8H_8N_4O_3S$) | | |

Example 2)-9

Preparation of N-cyano-N'-(2-phenylethyl)-2-thiophenecarboximidamide

Methyl N-cyano-2-thiophenecarboximidate (0.33 g, 2.0 mmol) was dissolved in methanol (2 ml), and 2-phenylethylamine (0.27 g, 2.2 mmol) was added. The mixture was stirred at room temperature for 1 hour. After the reaction was completed, the reaction solution was concentrated under reduced pressure, and the residue thus obtained was crystallized from diethyl ether-hexane to give the title compound (0.50 g, 1.97 mmol, yield: 98%) as colorless crystals.

Physico-chemical properties of N-cyano-N'-(2-phenylethyl)-2-thiophenecarboximidamide

MP: 106.8°–107.5° C.;

IR spectrum: ($cm^{-1}$, KBr) 2200, 1580;

NMR spectrum: (500 MHz, $CDCl_3$) δ (ppm) 7.89 (1H, s), 7.51 (1H, d, J=4.9Hz), 7.4–7.2 (5H), 7.14 (1H, t, J=4.9Hz), 5.98 (1H, brs), 3.76 (2H, dd, J=6.7, 12.8Hz), 2.97 (2H, t, J=6.7Hz);

| | Elementary Analysis: | | |
|---|---|---|---|
| | C | H | N |
| Calculated: | 65.85 | 5.13 | 16.46 |
| Found: | 65.67 | 5.11 | 16.36 (%) |
| | ($C_{14}H_{13}N_3S$) | | |

Example 2)-10

Preparation of N-cyano-N'-(2-phenylethyl) 3-thiophenecarboximidamide a) 3-cyanothiophene (0.66 g, 6.0 mmol) was dissolved in methanol (6 ml), and sodium methoxide (0.03 g, 0.6 mmol) was added. The mixture was stirred at room temperature for 28 hours. After the reaction was completed, acetic acid (0.03 g, 0.6 mmol) was added to neutralize the reaction solution, and the solution was concentrated under reduced pressure. Diethyl ether (50 ml) was added to the concentrated residue, and insolubles were removed by filtration. The filtrate was concentrated under reduced pressure to give the crude product of methyl 3-thiophenecarboximidate.

Next, cyanamide (0.5 g, 12 mmol) and a phosphate buffer (pH 6.0, 10 ml) of $Na_2HPO_4$ (0.86 g, 6 mmol) and $NaH_2P04\ 2H_2O$ (1.89 g, 12 mmol) were added to the oil, and the mixture was stirred at room temperature for 74 hours. After the reaction was completed, the reaction solution was extracted with dichloromethane (10 ml×4), and the dichloromethane layer was washed with water (50 ml), dried over anhydrous sodium sulfate and then concentrated under reduced pressure. The residue thus obtained was subjected to chromatography on a silica gel column (WAKO GEL C-200, 30 g) eluting with chloroform. The eluted fractions were concentrated under reduced pressure to give methyl N-cyano-3-thiophenecarboximidate (0.70 g, 4.2 mmol, yield: 70%) as a colorless oil.

Physico-chemical properties of methyl N-cyano-3-thiophenecarboximidate

IR spectrum: (cm$^{-1}$, neat) 2200, 1590, 1300;

NMR spectrum: (500 MHz, CDCl3) δ (ppm) 8.69 (1H, dd, J=2.0, 3.4Hz), 7.82 (1H, dd, J=2.0, 5.6Hz), 7.41 (1H, dd, J=3.4, 5.6Hz), 4.03 (3H, s).

b) Methyl N-cyano-3-thiophenecarboximidate (0.33 g, 2.0 mmol) was dissolved in methanol (2 ml), and 2-phenylethylamine (0.27 g, 2.2 mmol) was added. The mixture was stirred at room temperature for 40 minutes. After the reaction was completed, the reaction solution was concentrated under reduced pressure, and the residue thus obtained was crystallized from diethyl ether to give the title compound (0.48 g, 1.89 mmol, yield: 95%) as colorless crystals.

Physico-chemical properties of N-cyano-N'-(2-phenylethyl)-3-thiophenecarboximidamide

MP: 156.9°–157.7° C.;

IR spectrum: (cm$^{-1}$, KBr) 2170, 1550;

NMR spectrum: (500 MHz, CDCl3) δ (ppm) 7.96 (1H, s), 7.45–7.20 (7H), 6.20 (1H, brs), 3.73 (2H, dd, J=6.7, 13.4Hz), 2.97 (2H, t, J=6.7Hz);

| | Elementary Analysis: | | |
|---|---|---|---|
| | C | H | N |
| Calculated: | 65.85 | 5.13 | 16.46 |
| Found: | 65.77 | 5.01 | 16.29 (%) |
| | (C14H13N3S) | | |

Example 2)-11

Preparation of N-cyano-N'-(2-phenylethyl)-4-cyanobenzene-carboximidamide a) 1,4-dicyanobenzene (6.41 g, 50 mmol) was suspended in methanol (100 ml), and sodium methoxide (0.27 g, 5.0 mmol) was added. The mixture was stirred at room temperature for 22 hours. After the reaction was completed, acetic acid (0.31 g, 5.1 mmol) was added to neutralize the reaction solution, and the solution was concentrated under reduced pressure. Dichloromethane (50 ml) and diethyl ether (50 ml) were added to the concentrated residue, and insolubles were removed by filtration. The filtrate was concentrated under reduced pressure to give the crude product of methyl 4-cyanobenzenecarboximidate (5.77 g) as colorless powder.

Next, cyanamide (3.03 g, 72 mmol) and a phosphate buffer (pH 6.0, 20 ml) of Na2HPO4 (5.11 g, 36 mmol) and NaH2PO4.2H2O (11.23 g, 72 mmol) were added to the powder, and the mixture was stirred at room temperature for 23 hours. After the reaction was completed, the reaction solution was concentrated under reduced pressure. Chloroform (200 ml) and methanol (200 ml) were added to the residue, and insolubles were removed by filtration through celite. The filtrate was concentrated. The concentrate was crystallized by adding diethyl ether (100 ml). Deposited crystals were collected by filtration and washed with diethyl ether. The filtrate and the wash liquid were collected together and concentrated under reduced pressure to give methyl N-cyano-4-cyanobenzenecarboximidate (3.63 g, 19.6 mmol, yield: 39%) as colorless powder.

Physico-chemical properties of methyl N-cyano-4-cyanobenzenecarboximidate

MP: 94.5°–95.0° C.;

IR spectrum: (cm$^{-1}$, KBr) 2200, 1600, 1350;

NMR spectrum: (500 MHz, CDCl3) δ (ppm) 8.18 (2H, d, J=8.6Hz), 7.83 (2H, d, J=8.6Hz), 4.13 (3H, s);

| | Elementary Analysis: | | |
|---|---|---|---|
| | C | H | N |
| Calculated: | 64.86 | 3.81 | 22.69 |
| Found: | 64.81 | 3.77 | 22.41 (%) |
| | (C10H7N3O) | | |

b) Methyl N-cyano-4-cyanobenzenecarboximidate (0.37 g, 2.0 mmol) was suspended in methanol (4 ml), and 2-phenylethylamine (0.25 g, 2.1 mmol) was added. The mixture was stirred at room temperature for 1 hour. After the reaction was completed, methanol (6 ml) and diethyl ether (10 ml) were added to the reaction solution, and deposited crystals were collected by filtration to give the title compound (0.51 g, 1.87 mmol, yield: 94%) as colorless crystals.

Physico-chemical properties of N-cyano-N'-(2-phenylethyl)-4-cyanobenzenecarboximidamide

MP: 261.0°–261.8° C.;

IR spectrum: (cm$^{-1}$, KBr) 2170, 1550;

NMR spectrum: (500 MHz, CD3OD) δ (ppm) 7.84 (2H, d, J=8.5Hz), 7.64 (2H, d, J=8.5Hz), 7.36–7.22 (5H), 3.73 (2H, t, J=7.3Hz), 3.00 (2H, t, J=7.3Hz);

| | Elementary Analysis: | | |
|---|---|---|---|
| | C | H | N |
| Calculated: | 74.43 | 5.14 | 20.42 |
| Found: | 74.13 | 5.35 | 20.21 (%) |
| | (C17H14N4) | | |

Example 2)-12

Preparation of 3-cyano-2-methyl-(2-nitroxyethyl)isothiourea a) 2-Nitroxyethylamine nitrate (0.56 g, 3.3 mmol) was dissolved in methanol (2 ml), and sodium methoxide (0.18 g, 3.3 mmol) was added. Dimethyl-N-cyanodithioiminocarbonate (0.44 g, 3.0 mmol) dissolved in methanol (4 ml) was added further to the solution. The mixture was stirred at room temperature for 24 hours. After the reaction was completed, the reaction solution was concentrated under reduced pressure, and the residue obtained was crystallized from diethyl ether to give colorless powder. The powder thus obtained was washed with water and recrystallized from methanol to give the title compound (0.26 g, 1.3 mmol, yield: 43%) as colorless crystals.

Physico-chemical properties of 3-cyano-2-methyl-1-(2-nitroxyethyl)isothiourea

MP: 135°–135.5° C.;

IR spectrum: (cm$^{-1}$, KBr) 2170, 1640, 1560, 1280;

NMR spectrum: (500 MHz, CD3OD) δ (ppm) 4.63 (2H, s), 3.74 (2H, s), 2.60 (3H, s);

| | Elementary Analysis: | | |
|---|---|---|---|
| | C | H | N |
| Calculated: | 29.41 | 3.95 | 27.44 |
| Found: | 29.33 | 3.77 | 27.15 (%) |
| | ($C_5H_8N_4O_3S$) | | |

Figure 1:
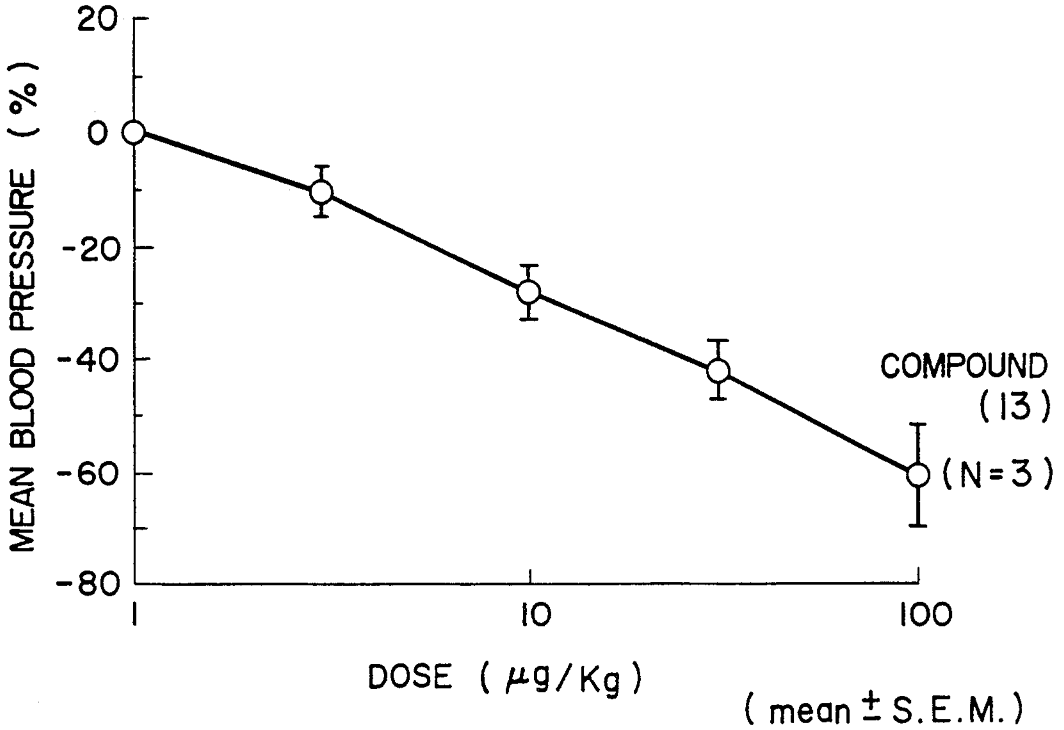
FIG. 1 is a graph which illustrates the change in blood pressure in a beagle upon the intravenous administration of the compound of the present invention represented by the formula (I) [compound (13)].
Figure 2:
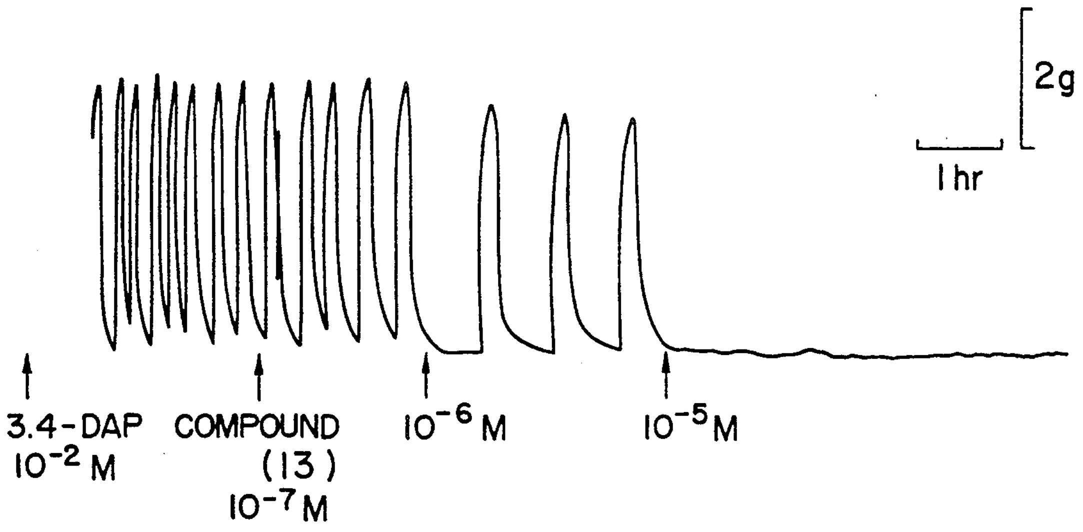
FIG. 2 is a graph which illustrates the inhibitory effect of the compound of the present invention represented by the formula (I) [compound (13)] on the rhythmic contraction of a coronary artery of a dog induced by 3.4-DAP.
Figure 3:
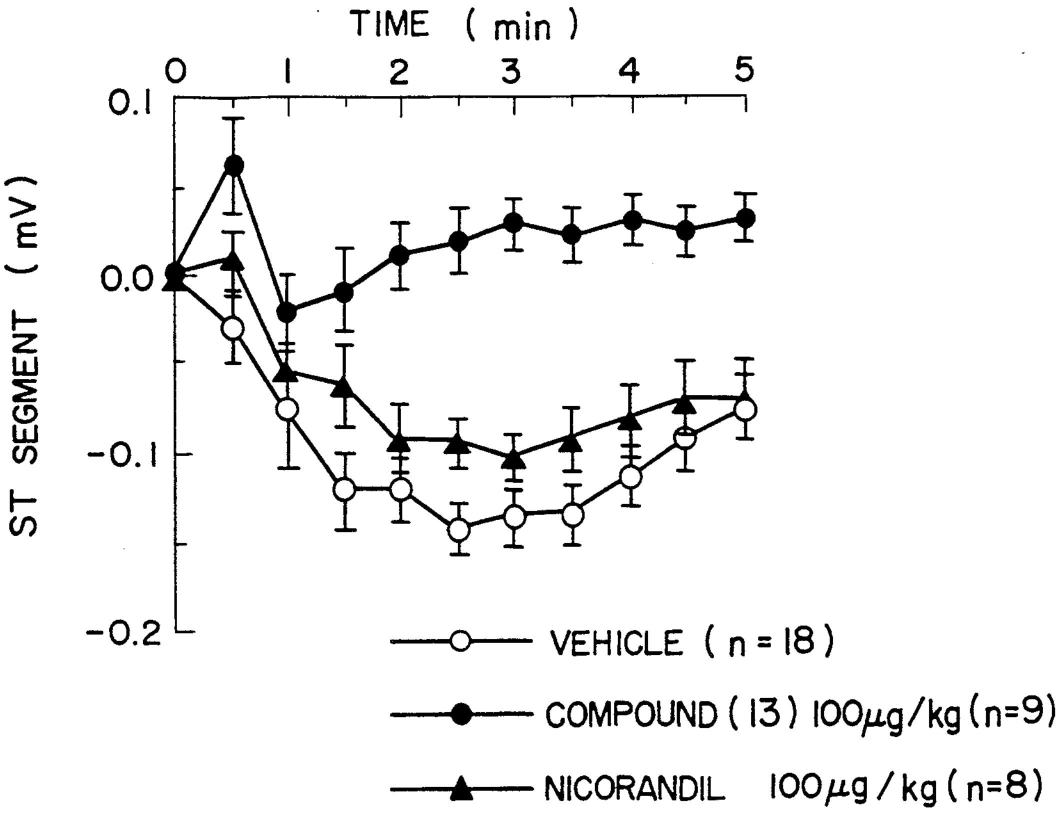
FIG. 3 is a graph which illustrates the effects of the compound of the present invention represented by the formula (I) [compound (13)] and nicorandil on an angina pectoris model induced by vasopressin.
Figure 4:
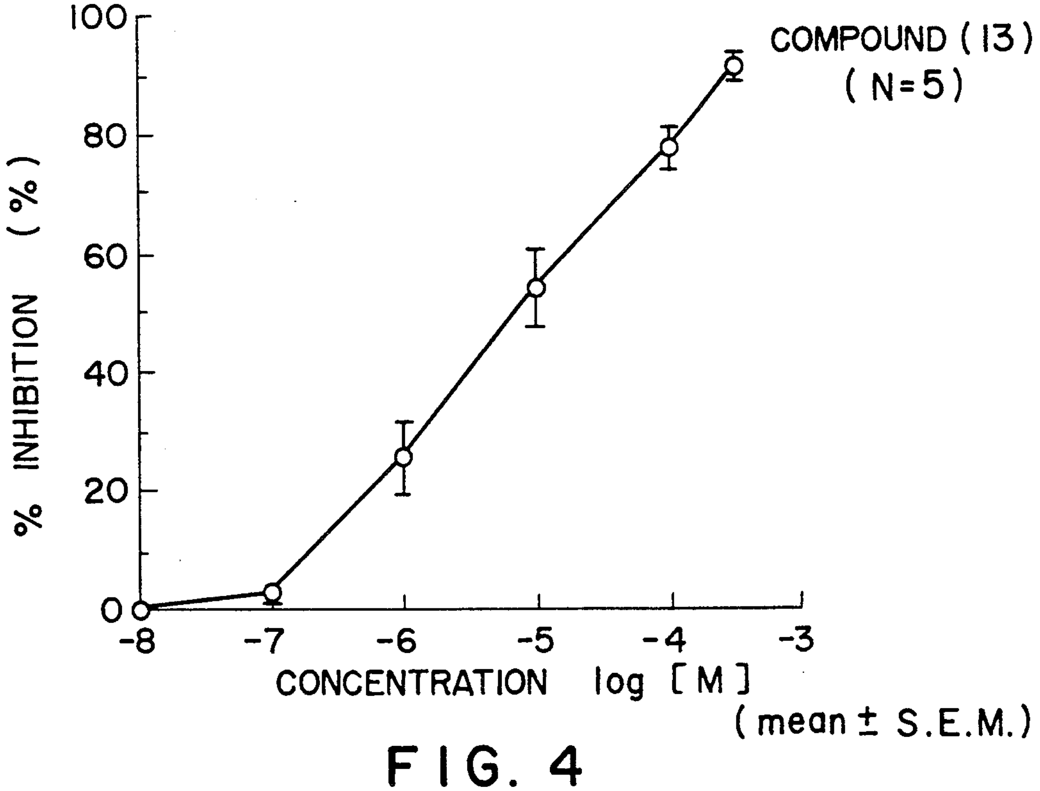
FIG. 4 is a graph which illustrates the relaxation effect of the compound of the present invention represented by the formula (I) [compound (13)] on the basilar artery of a beagle.
Figure 5:
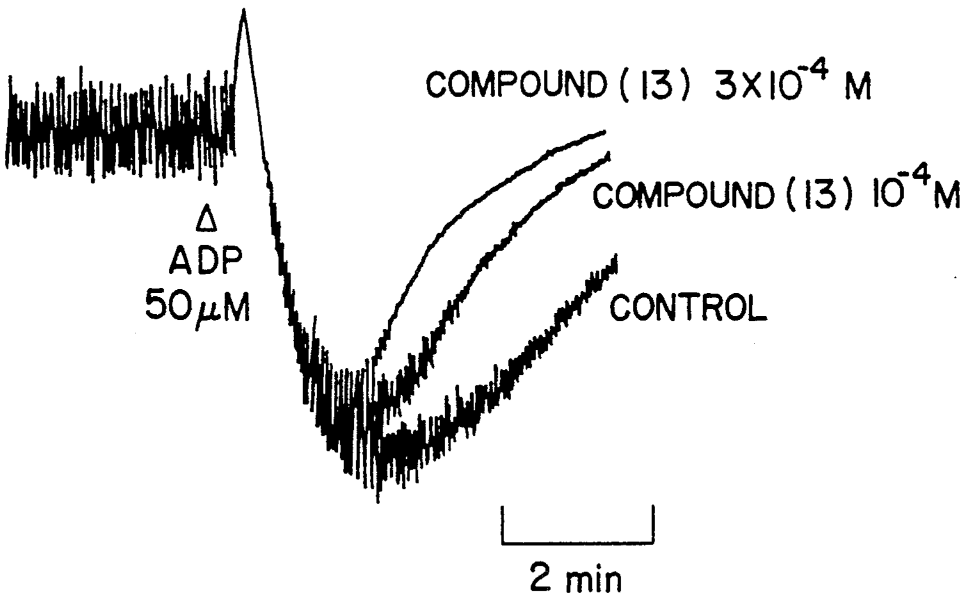
FIG. 5 is a graph which illustrates the inhibitory effect of the compound of the present invention represented by the formula (I) [compound (13)] on platelet aggregation.
Figure 6:
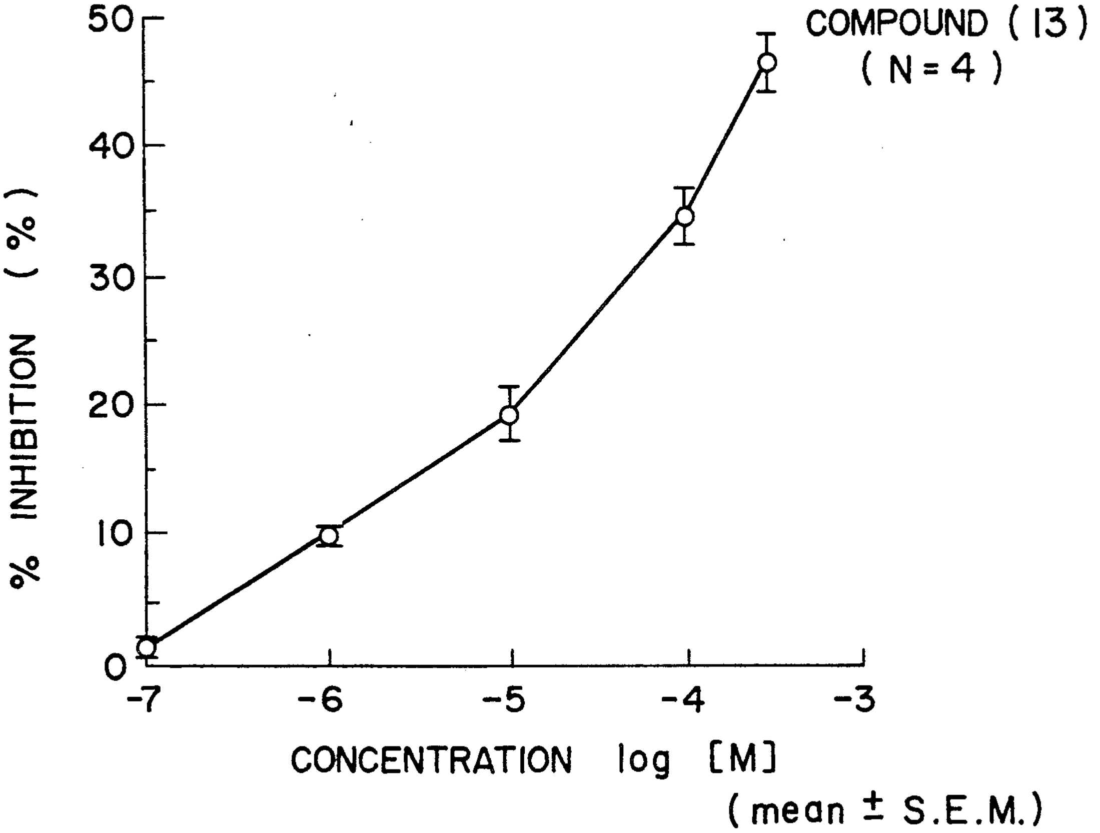
FIG. 6 is a graph which illustrates the relaxation effect of the compound of the present invention represented by the formula (I) [compound (13)] on the smooth muscle of a trachea.

We claim:

1. An N-cyanopyridinecarboximidate compound as an intermediate represented by the following formula (II):

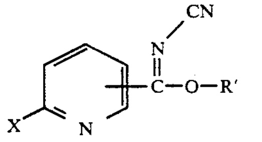

(II)

wherein X represents a hydrogen atom or a chlorine atom, and R′ represents an alkyl group with 1-5 carbon atoms.

2. A carboximidamide derivative represented by the following formula (A) or an acid adduct salt thereof:

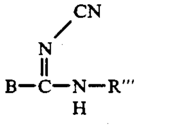

(A)

wherein when B is

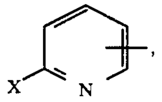

X represents a hydrogen atom or a chlorine atom, R‴ represents an alkyl group with 5-8 carbon atoms or an alkyl group with 2-3 carbon atoms having a nitroxyl group, and when B is

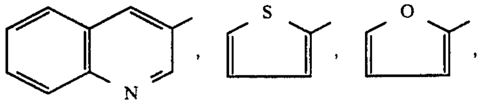

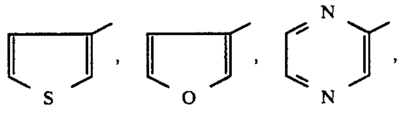

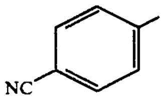

or $H_3C—S—$, R‴ represents

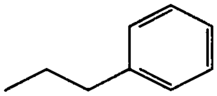

or

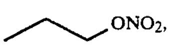

provided that where B is

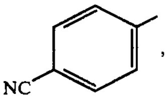

,

R‴ is not

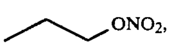

where B is $H_3C—S—$,

R‴ is not

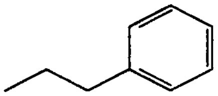

and where

B is

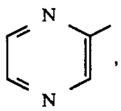

, R‴ is not

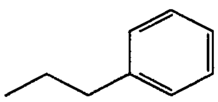

3. A pyridinecarboximidamide derivative represented by the following formula (I) or an acid adduct salt thereof:

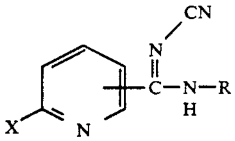

(I)

wherein X represents a hydrogen atom or a chlorine atom, R represents an alkyl group with 5-8 carbon atoms or an alkyl group with 2-3 carbon atoms having a nitroxyl group.

4. A pyridinecarboximidamide derivative or an acid adduct salt thereof according to claim 3, wherein X in formula (I) is a hydrogen atom.

5. A pyridinecarboximidamide derivative or an acid adduct salt thereof according to claim 3, wherein X in formula (I) is a chlorine atom and R in formula (I) is an alkyl group with 2-3 carbon atoms having a nitroxyl group.

6. A pyridinecarboximidamide derivative or an acid adduct salt thereof according to claim 4, wherein R in formula (I) is selected from the group consisting of an alkyl with 5 or 6 carbon atoms, nitroxylethyl and nitroxypropyl.

7. A pyridinecarboximidamide derivative or an acid adduct salt thereof according to claim 5, wherein R in formula (I) is nitroxylethyl.

8. A pyridinecarboximidamide derivative or an acid adduct salt thereof according to claim 3, which is selected from the group consisting of the following compounds:

N-cyano-N'-(2-nitroxyethyl)-2-pyridinecarboximidamide;

N-cyano-N'-(2,2-dimethylpropyl-2-pyridinecarboximidamide;

N-cyano-N'-(1,2,2-trimethylpropyl-2-pyridinecarboximidamide;

N-cyano-N'-(2-nitroxyethyl)-3-pyridinecarboximidamide;

N-cyano-N'-(3-nitroxypropyl)-3-pyridinecarboximidamide;

N-cyano-N'-(3,3-dimethylbutyl)-3-pyridinecarboximidamide;

N-cyano-N'-(2-nitroxyethyl-4-pyridinecarboximidamide;

N-cyano-N'-(3-nitroxypropyl)-4-pyridinecarboximidamide; and

N-cyano-N'-(2-nitroxyethyl)-3-(6-chloropyridine)carboximidamide.

9. A carboximidamide derivative represented by the following formula (I') or an acid adduct salt thereof.

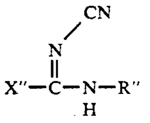 (I')

wherein X'' represents

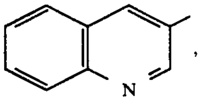, 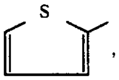, 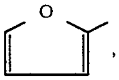,

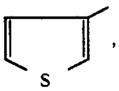, 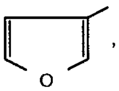, 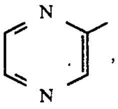, 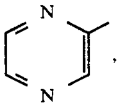,

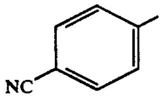 or H₃C—S—, and R'' represents

-continued

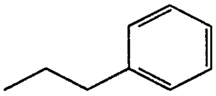 or 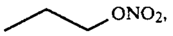, provided where X'' is 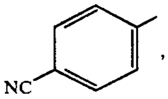, R'' is not 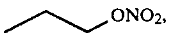, where X'' is $H_3C$—S—, R'' is not 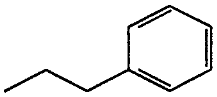 and where X'' is 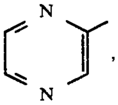, R'' is not 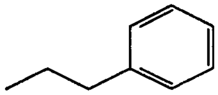

10. A carboximidamide derivative according to claim 9, which is selected from the group consisting of the following compounds:

N-cyano-N'-(2-nitroxyethyl)-3-quinolinecarboximidamide;

N-cyano-N'-(2-phenylethyl)-3-quinolinecarboximidamide;

N-cyano-N'-(2-nitroxyethyl)pyrazinecarboximidamide;

N-cyano-N'-(2-nitroxyethyl)-2-furancarboximidamide;

N-cyano-N'-(2-phenylethyl)-2-furancarboximidamide;

N-cyano-N'-(2-nitroxyethyl)-3-furancarboximidamide;

N-cyano-N'-(2-phenylethyl)-3-furancarboximidamide;

N-cyano-N'-(2-nitroxyethyl)-2-thiophenecarboximidamide;

N-cyano-N'-(2-phenylethyl)-2-thiophenecarboximidamide;

N-cyano-N'-(2-phenylethyl)-2-thiophenecarboximidamide;

N-cyano-N'-(2-phenylethyl)-4-cyanobenzenecarboximidamide; and

3-Cyano-2-methyl-1-(2-nitroxyethyl)isothiourea.

11. An N-cyanopyridinecarboximidate compound according to claim 1, wherein R' in formula (II) is an alkyl group with 1-3 carbon atoms.

12. An N-cyanopyridinecarboximidate compound according to claim 1, which is selected from the group consisting of the following compounds:

Methyl N-cyano-2-pyridinecarboximidate;

Isopropyl N-cyano-b 2-pyridinecarboximidate;

Isopropyl N-cyano-b 3-pyridinecarboximidate;

Isopropyl N-cyano-b 4-pyridinecarboximidate; and

Isopropyl N-cyano-b 3-(6-chloropyridine)carboximidate.

* * * * *